US010011018B2

(12) United States Patent
McGrogan et al.

(10) Patent No.: US 10,011,018 B2
(45) Date of Patent: Jul. 3, 2018

(54) ENTRY GUIDE MANIPULATOR WITH A ROLL SYSTEM AND AN INSTRUMENT MANIPULATOR POSITIONING SYSTEM

(71) Applicant: Intuitive Surgical Operations, Inc., Sunnyvale, CA (US)

(72) Inventors: Anthony K. McGrogan, San Jose, CA (US); Thomas G. Cooper, Menlo Park, CA (US); Kent M. Anderson, Mountain View, CA (US); Jeffrey D. Brown, Palo Alto, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 350 days.

(21) Appl. No.: 14/824,217

(22) Filed: Aug. 12, 2015

(65) Prior Publication Data
US 2016/0045271 A1    Feb. 18, 2016

Related U.S. Application Data

(60) Provisional application No. 62/038,096, filed on Aug. 15, 2014, provisional application No. 62/038,106, filed on Aug. 15, 2014.

(51) Int. Cl.
*B25J 15/00* (2006.01)
*A61B 19/00* (2006.01)
(Continued)

(52) U.S. Cl.
CPC .......... *B25J 15/0028* (2013.01); *A61B 19/22* (2013.01); *A61B 19/2203* (2013.01);
(Continued)

(58) Field of Classification Search
CPC .................................................. A61B 19/2203
(Continued)

(56) References Cited

U.S. PATENT DOCUMENTS 3,640,140 A    2/1972 Gulick et al.
5,876,325 A    3/1999 Mizuno et al.
(Continued)

FOREIGN PATENT DOCUMENTS

EP         2138105 B1      2/2012
WO    WO-2006124390 A2   11/2006
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

(Continued)

*Primary Examiner* — David S Luo

(57) ABSTRACT

A surgical system uses a single entry port in a wide variety of surgeries. To insert multiple surgical instruments into a patient through a single entry port requires that the shaft of at least one of the surgical instruments be bent between the base of the surgical instrument and the point where the shaft contacts a channel in an entry guide. Each surgical instrument is positioned by an instrument manipulator positioning system so that when the shaft is inserted in a channel of the entry guide, any bending of the shaft does not damage the surgical instrument and does not inhibit proper operation of the surgical instrument.

18 Claims, 34 Drawing Sheets

(51) Int. Cl.
*A61B 34/30* (2016.01)
*A61B 90/50* (2016.01)

(52) U.S. Cl.
CPC .............. *A61B 34/30* (2016.02); *A61B 90/50* (2016.02); *A61B 2019/2211* (2013.01); *A61B 2019/2234* (2013.01); *Y10S 901/36* (2013.01); *Y10S 901/38* (2013.01); *Y10S 901/39* (2013.01)

(58) Field of Classification Search
USPC .................................................. 318/560, 34
See application file for complete search history.

(56) References Cited

U.S. PATENT DOCUMENTS

| | | | |
|---|---|---|---|
| 6,007,550 | A | 12/1999 | Wang et al. |
| 6,120,433 | A | 9/2000 | Mizuno et al. |
| 6,451,027 | B1 | 9/2002 | Cooper et al. |
| 6,459,926 | B1 | 10/2002 | Nowlin et al. |
| 6,468,265 | B1 | 10/2002 | Evans et al. |
| 6,587,750 | B2 | 7/2003 | Gerbi et al. |
| 6,594,552 | B1 | 7/2003 | Nowlin et al. |
| 6,663,641 | B1 * | 12/2003 | Kovac ................ A61B 17/062 606/144 |
| 6,671,581 | B2 | 12/2003 | Niemeyer |
| 6,817,794 | B2 | 11/2004 | Kakutani |
| 6,866,671 | B2 | 3/2005 | Tierney et al. |
| 6,949,043 | B2 * | 9/2005 | Rhodes ................ E05F 11/488 475/170 |
| 7,648,513 | B2 | 1/2010 | Green et al. |
| 7,666,191 | B2 | 2/2010 | Orban, III et al. |
| 7,699,855 | B2 | 4/2010 | Anderson et al. |
| 7,942,868 | B2 | 5/2011 | Cooper |
| 7,963,913 | B2 | 6/2011 | Devengenzo et al. |
| 8,083,667 | B2 | 12/2011 | Cooper et al. |
| 8,562,592 | B2 * | 10/2013 | Conlon ................ A61B 17/29 600/141 |
| 9,333,042 | B2 * | 5/2016 | Diolaiti ................ A61B 90/37 |
| 2003/0036478 | A1 | 2/2003 | Seki et al. |
| 2003/0050649 | A1 | 3/2003 | Brock et al. |
| 2003/0083673 | A1 | 5/2003 | Tierney et al. |
| 2007/0032906 | A1 | 2/2007 | Sutherland et al. |
| 2007/0137371 | A1 | 6/2007 | Devengenzo et al. |
| 2008/0065105 | A1 | 3/2008 | Larkin et al. |
| 2011/0201883 | A1 | 8/2011 | Cooper et al. |
| 2011/0277775 | A1 | 11/2011 | Holop et al. |
| 2011/0277776 | A1 | 11/2011 | McGrogan et al. |
| 2011/0282351 | A1 | 11/2011 | Cooper et al. |
| 2013/0066335 | A1 | 3/2013 | Baerwinkel et al. |
| 2013/0296886 | A1 | 11/2013 | Green et al. |
| 2013/0304084 | A1 | 11/2013 | Beira et al. |

FOREIGN PATENT DOCUMENTS

| | | |
|---|---|---|
| WO | WO-2011143020 A1 | 11/2011 |
| WO | WO-2011143022 A1 | 11/2011 |
| WO | WO-2015023730 A1 | 2/2015 |

OTHER PUBLICATIONS

International Search Report and Written Opinion for Application No. PCT/US2015/044757, dated Nov. 11, 2015, 10 pages.
Extended European Search Report for Application No. EP15831381.7, dated Feb. 15, 2018, 12 pages.

* cited by examiner

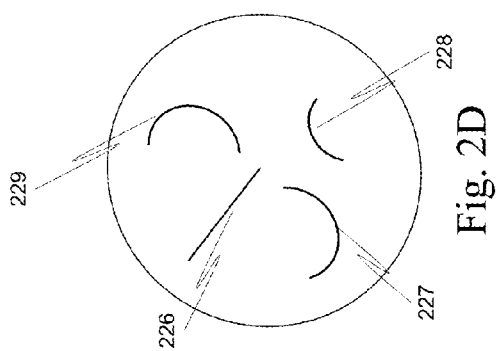
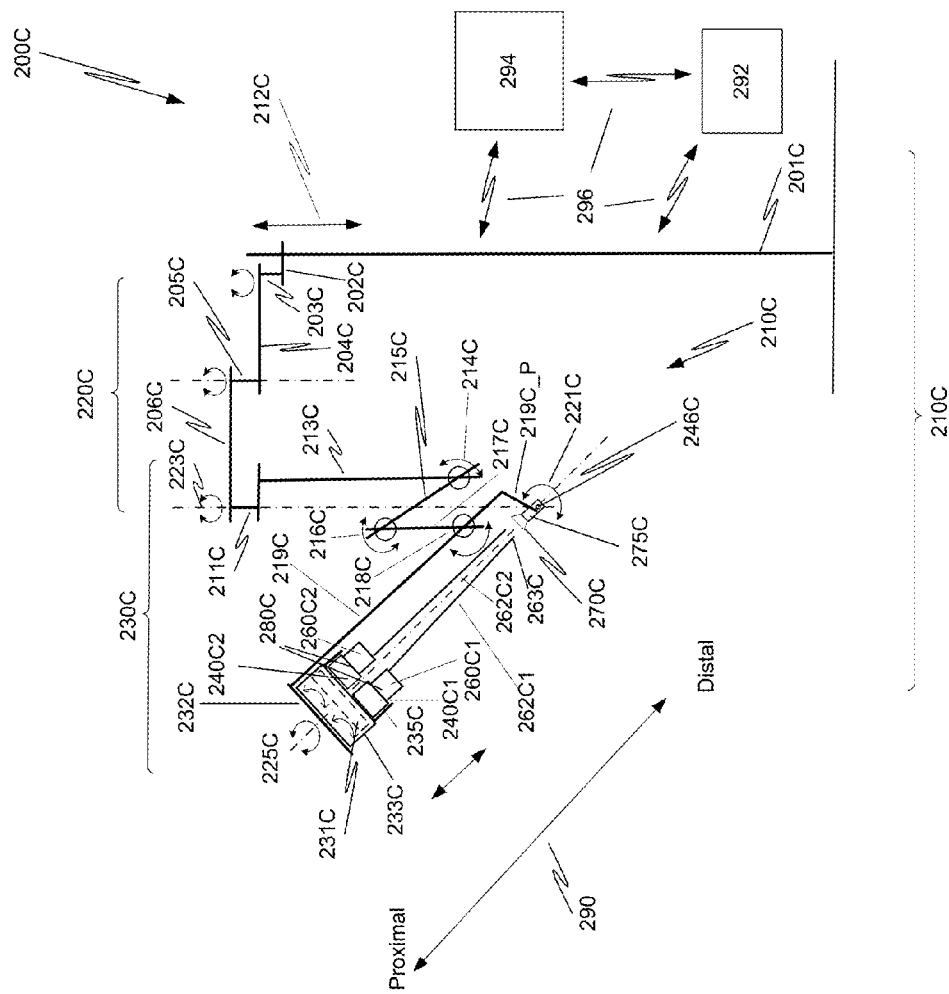
Fig. 2D
Fig. 2C

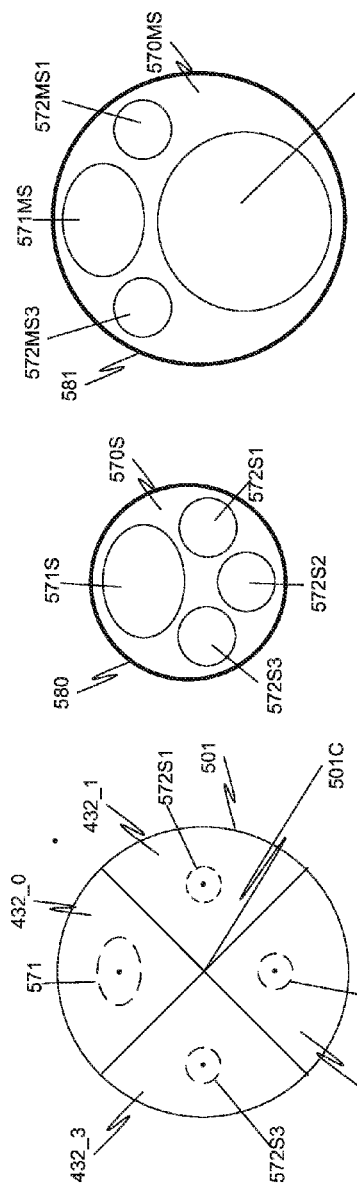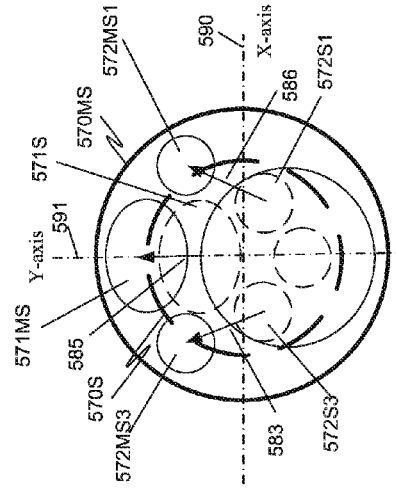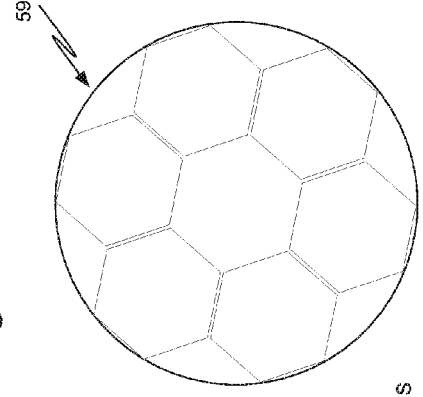

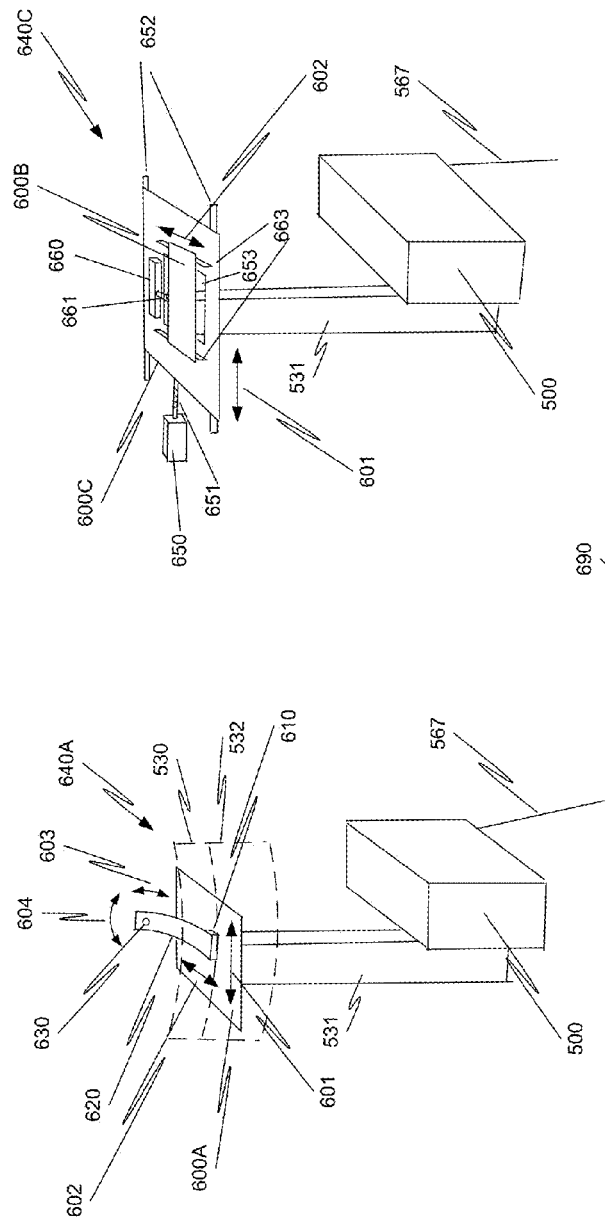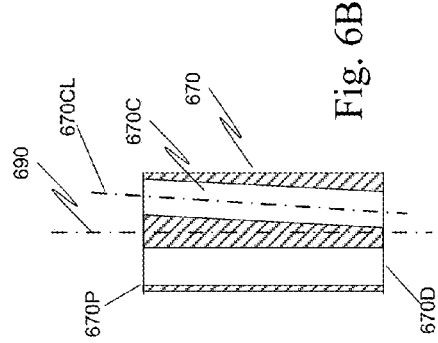
Fig. 6C
Fig. 6B
Fig. 6A

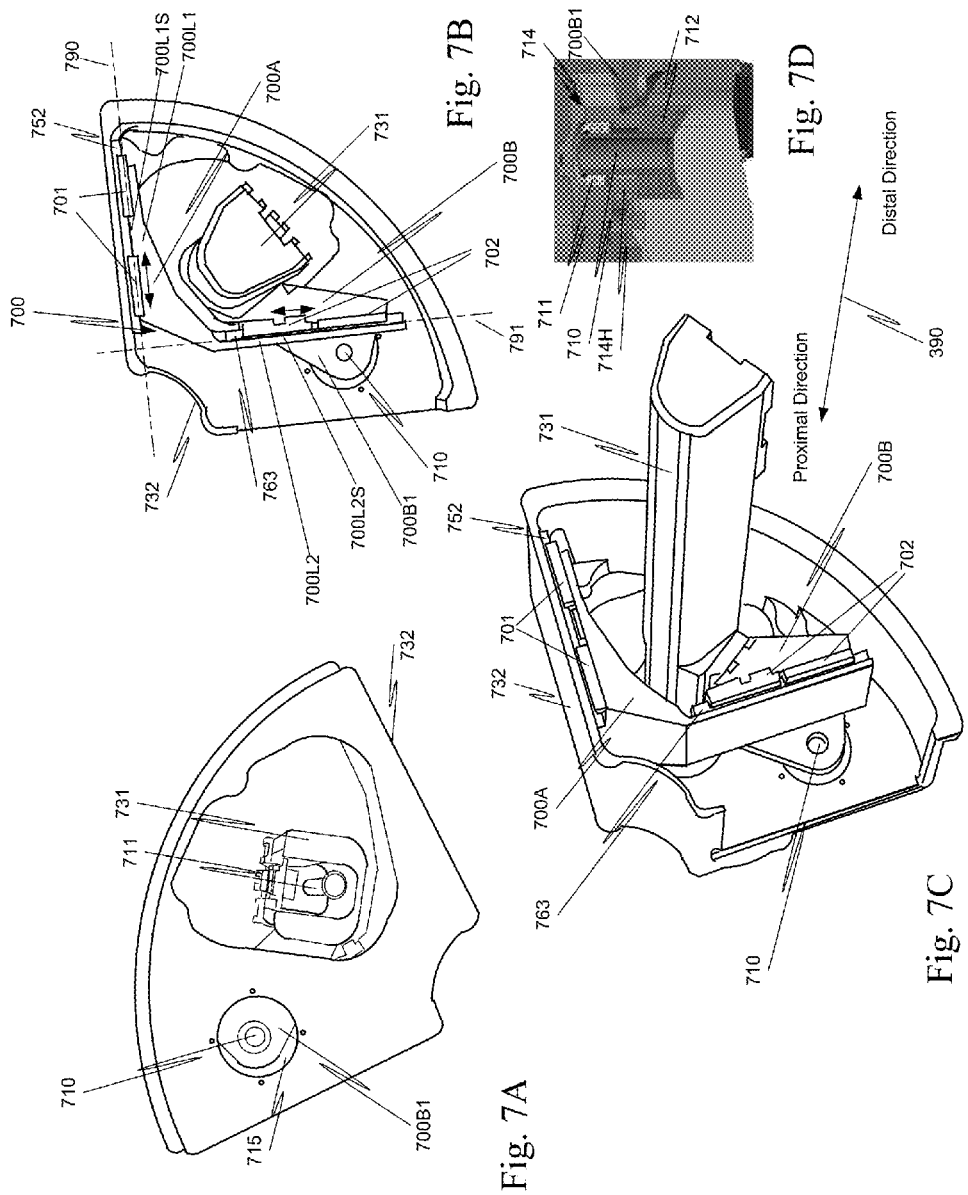

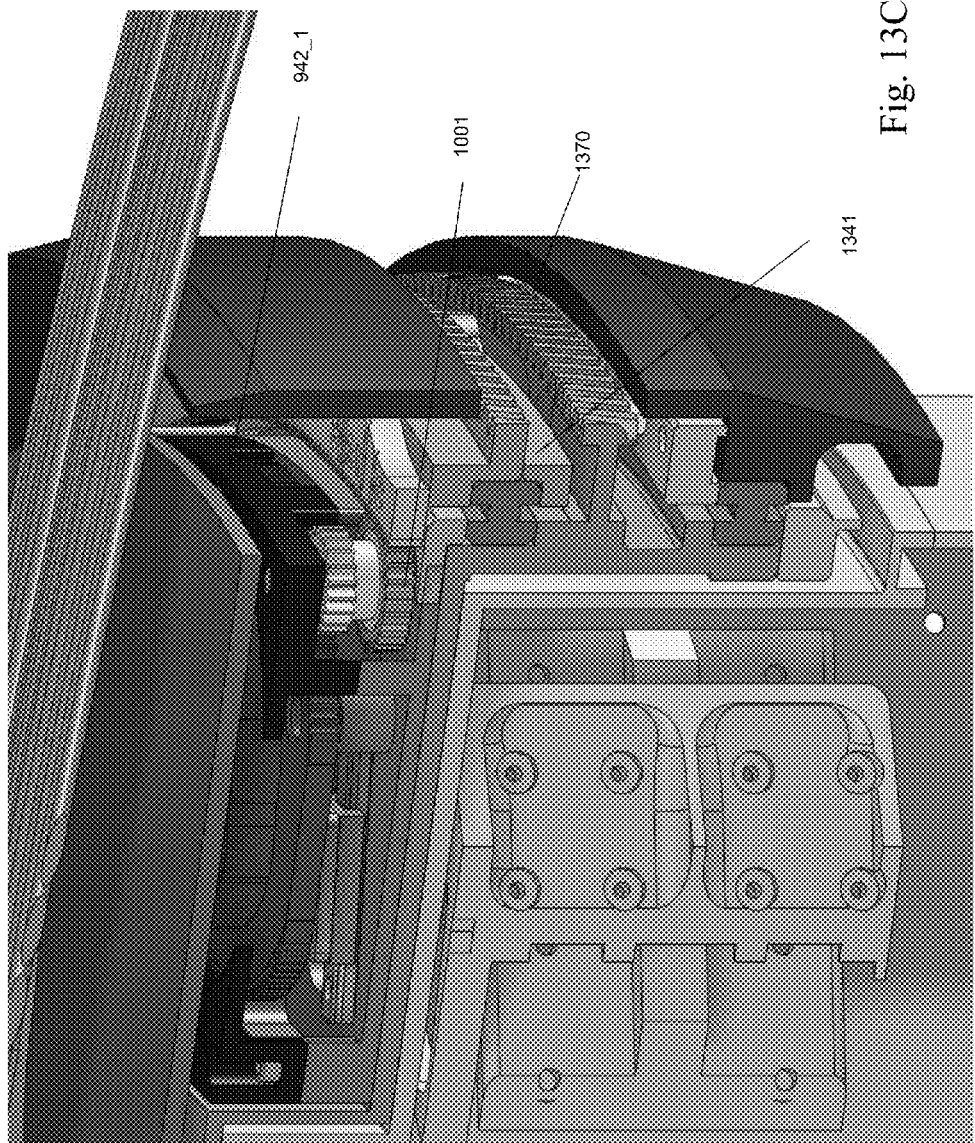

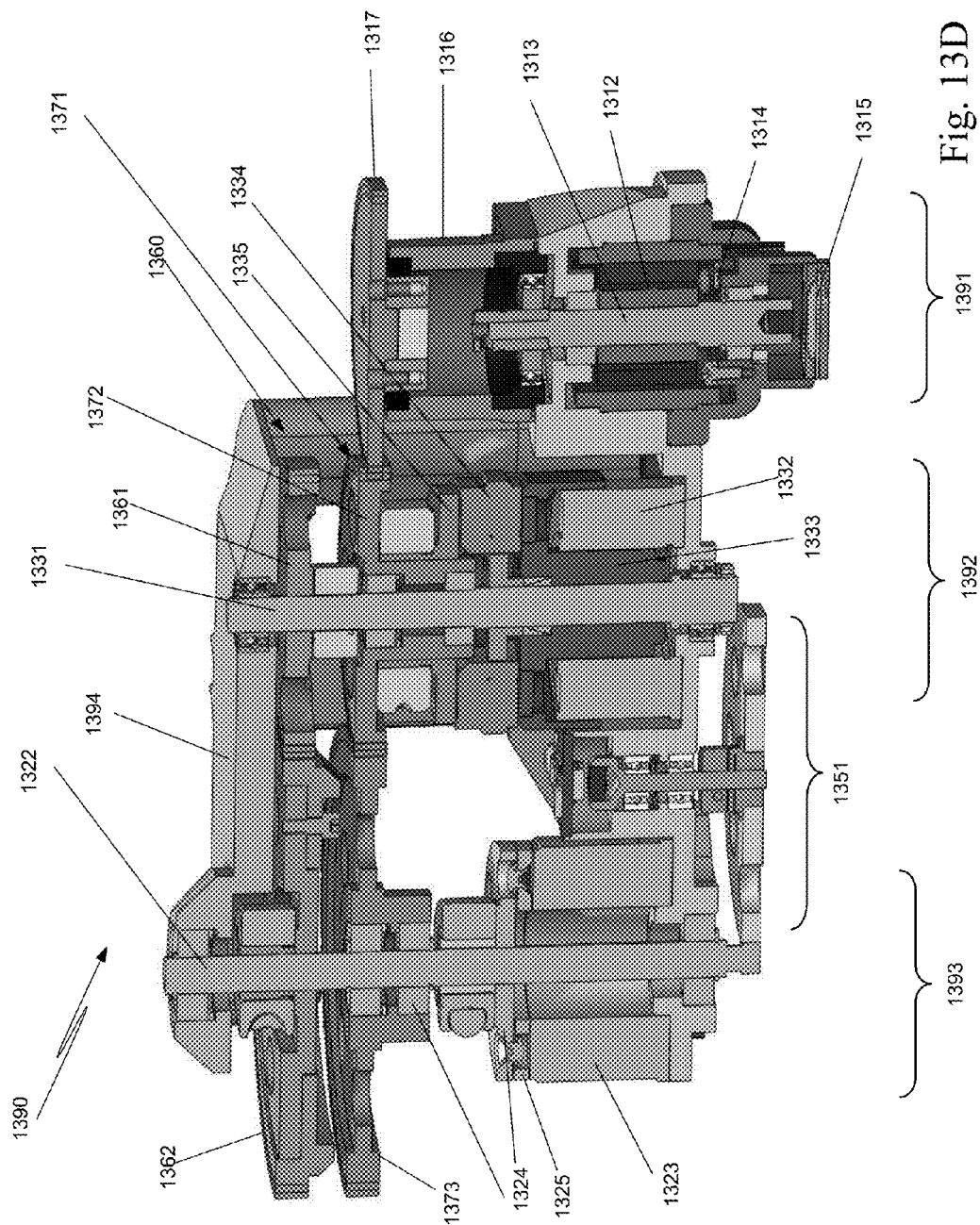

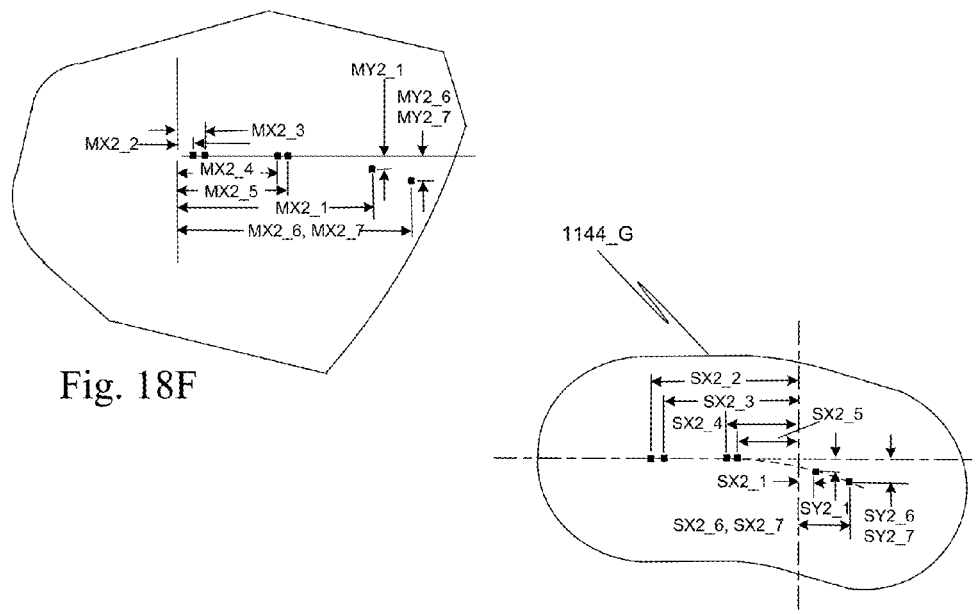
Fig. 18F
Fig. 18G
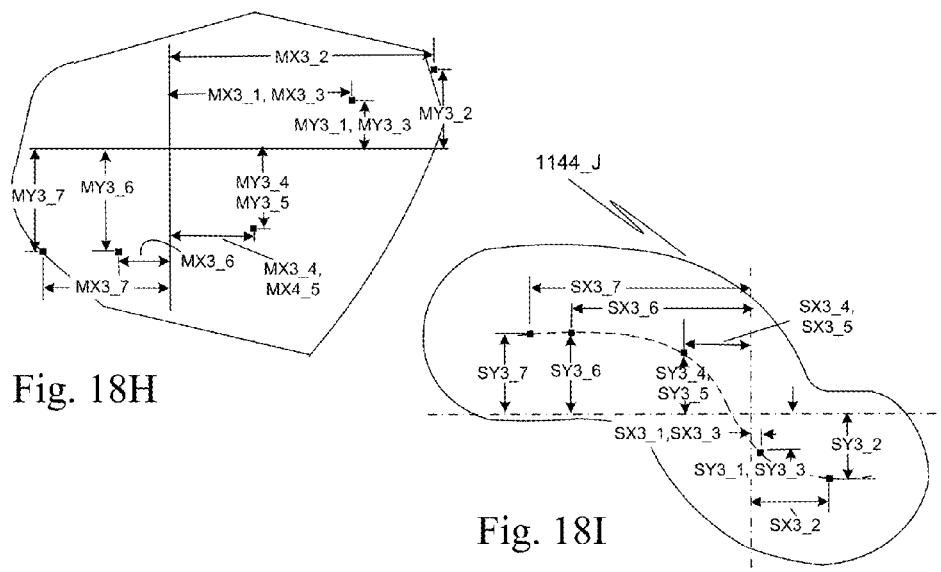
Fig. 18H
Fig. 18I

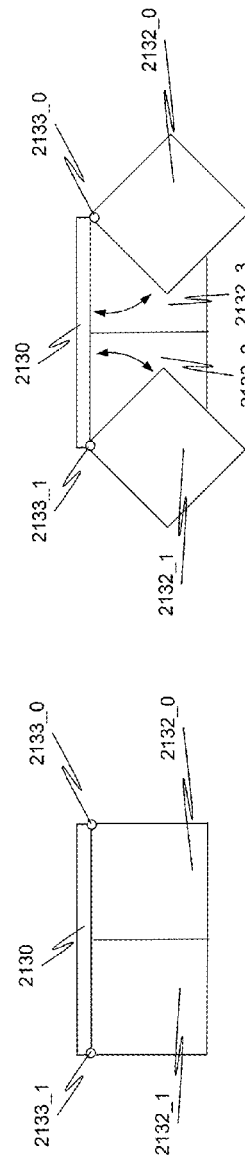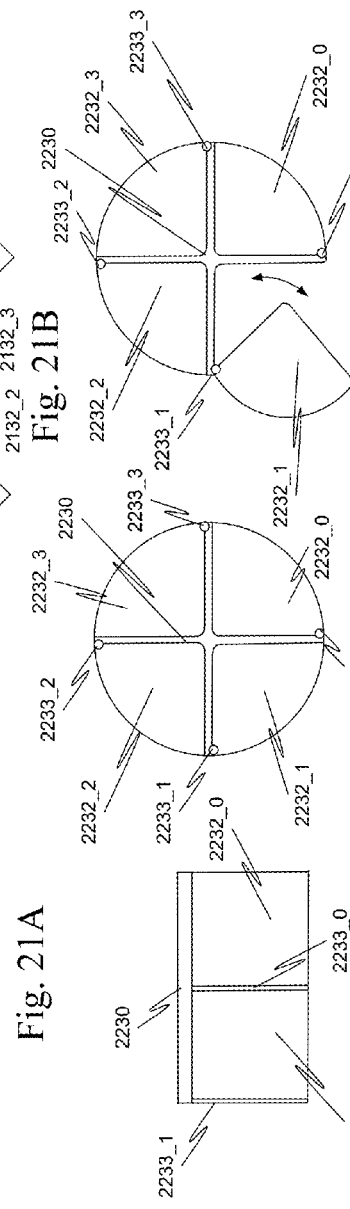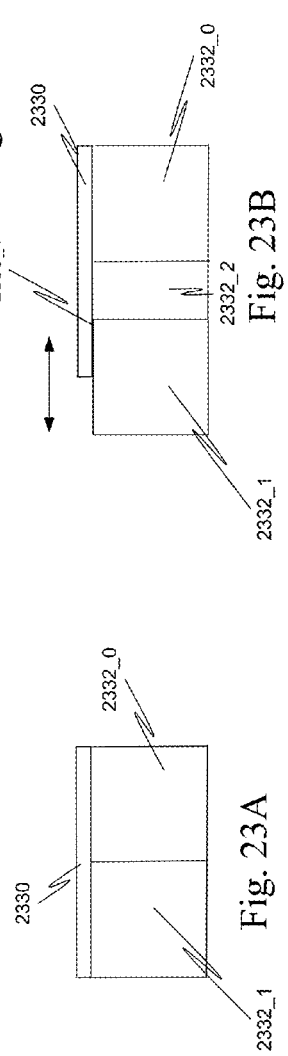

ENTRY GUIDE MANIPULATOR WITH A ROLL SYSTEM AND AN INSTRUMENT MANIPULATOR POSITIONING SYSTEM

RELATED APPLICATIONS

This application claims priority to and the benefit of:
U.S. Patent Application No. 62/038,096, (filed Aug. 15, 2014, disclosing "A Surgical System With Variable Entry Guide Configurations," by Anthony K. McGrogan et al.); and
U.S. Patent Application No. 62/038,106, (filed Aug. 15, 2014, disclosing "An Entry Guide Manipulator With A Roll System and An Instrument Manipulator Positioning System," by Anthony K. McGrogan et al.), each of which is incorporated herein by reference in its entirety.

BACKGROUND

Field of Invention

The present invention relates generally to surgical instruments, and more particularly to positioning of surgical instruments.

Description of Related Art

Surgical systems, such as those employed for minimally invasive medical procedures, can include large and complex equipment to precisely control and drive relatively small tools or instruments. FIG. 1A illustrates an example of a known teleoperated controlled system 100. System 100, which may, for example, be part of a da Vinci® Surgical System commercialized by Intuitive Surgical, Inc., includes a patient-side cart 110 having multiple arms 130. Each arm 130 has a docking port 140 that generally includes a drive system with a mechanical interface for mounting and providing mechanical power for operation of an instrument 150. Arms 130 can be used during a medical procedure to move and position respective medical instruments 150 for the procedure.

FIG. 1B shows a bottom view of a known instrument 150. Instrument 150 generally includes a transmission or backend mechanism 152, a main tube 154 extending from the backend mechanism 152, and a functional tip 156 at the distal end of main tube 154. Tip 156 generally includes a medical tool such as scissors, forceps, or a cauterizing instrument that can be used during a medical procedure. Drive cables or tendons 155 are connected to tip 156 and extend through main tube 154 to backend mechanism 152. Backend mechanism 152 typically provides a mechanical coupling between the drive tendons 155 of instrument 150 and motorized axes of the mechanical interface of a docking port 140. In particular, gears or disks 153 engage features on the mechanical interface of a docking port 140. Instruments 150 of system 100 can be interchanged by removing one instrument 150 from docking port 140 and then installing another instrument 150 in place of the instrument removed.

SUMMARY

A surgical system includes a single entry port, which may be used in a wide variety of different surgical procedures. The variety of surgical procedures uses various combinations of instruments that enter a patient through the single entry port. The instruments, in one aspect, are grouped into sets of instruments based on the shaft characteristics of the instruments, e.g., standard surgical instruments (graspers, retractors, scissors, cautery, and the like), advanced surgical instruments (staplers, vessel sealers, and the like) that may have a cross section larger than standard surgical instruments or unique cross sections, and camera instruments (visible, infrared, ultrasound, and the like) that also may have a cross section larger than standard surgical instruments or unique cross sections. These instruments can be manually controlled, controlled with computer assistance (fully or cooperatively controlled), or teleoperatively controlled.

The different surgeries that can be performed using at least one entry port may be performed on different regions of the body. For example, one surgery may be performed through the mouth of a patient; another surgery may be performed between the ribs of a patient; and other surgeries may be performed through other natural or incision orifices of a patient. Not only is the surgical system configured to use a variety of instruments, but also the surgical system is configured to use a variety of different entry guides, which guide the instruments into the patient toward the surgical site. At least a portion of each instrument is inserted through a corresponding channel in an entry guide. Typically, a different entry guide is used for each different type of surgery. The entry guide selected for a particular surgical procedure may maintain an insufflation seal, if necessary, and entry guide supports the shafts of the instruments at the entry point into the body of the patient.

To insert multiple instruments into a patient through a single entry port may require one or more of the shafts of the instruments to bend between where the shaft is connected to the housing of the instrument and the point where the shaft contacts a channel of the entry guide. This bend may be permanently pre-formed in a rigid instrument, such as a camera instrument, or may happen non-permanently when inserting the shaft of an instrument into a channel of the entry guide. If the shaft of the instrument is bent too much, the shaft of the instrument may be damaged and/or the instrument may not perform properly during the surgery.

An entry guide manipulator controls the position and orientation of an entry guide. The entry guide includes two or more channels. Each channel receives a surgical instrument and guides the surgical instrument toward the surgical site. Thus, two or more instruments are guided toward the surgical site via a single opening (port) in the body. An entry guide channel may be configured to receive an individual instrument type, such as a camera with an oval cross section. Or, an entry guide channel may be configured to receive many instrument types, such as therapeutic instruments with round cross sections. Various combinations of entry guide channel configurations may be used. The entry guide manipulator also controls the position and orientation of the instruments that extend through the entry guide channels. Thus, in one aspect, each entire instrument is positioned by the entry guide manipulator so that when the instrument's shaft is inserted in the channel of the entry guide, any bending of the shaft is not permanent and does not inhibit proper operation of the instrument such as for insertion/withdrawal or roll (if applicable). This positioning assures that any bending does not damage the instrument, and that any bending does not affect the correct operation of the instrument. Various entry guide channel arrangements may be used, each arrangement being associated with a different single entry port area in a patient. For example, an entry guide may have a circular cross section with its channels arranged generally equally spaced within the cross section. As a second example, an entry guide may have an oblong cross section with its channels arranged generally in a line. Therefore, in one aspect, for each entry guide with a different channel configuration, each instrument is positioned so that stresses induced by any bend in the shaft remain within a predetermined stress profile for the individual instrument, i.e., the stress on the shaft is controlled such that the shaft does not yield and permanently change shape. Additionally, the stress is maintained so that as the shaft rolls in the entry guide or is inserted and withdrawn through the entry guide, the cycling stress does not fatigue and break the shaft. This cycling stress load is a consideration associated with instrument life. And so, an individual instrument type is placed at a first location for entry into a corresponding channel in a first entry guide configuration, and the individual instrument type is placed at a different, second location for entry into a corresponding channel in a second entry guide configuration.

In one aspect, the entry guide manipulator simultaneously positions instrument mount interfaces for the instruments with respect to the channels in an entry guide so that when the shafts of the instruments are inserted into channels in the entry guide, any bending of the instrument shafts does not damage the instruments and does not inhibit operation of the instruments. If an instrument shaft is bent to the point that the shaft does not return to its original shape when withdrawn from the entry guide, the instrument is considered damaged. The entry guide manipulator is configured to make these position adjustments for each entry guide in a family of entry guides, and in one aspect, the position adjustments for the entire instrument is made with little or no user input.

In addition, the instrument manipulator positioning system eliminates the need for surgical procedure-specific instruments. In other words, the instrument manipulator positioning system allows use of a common set of instruments with a variety of entry guides by moving the instrument shafts as appropriate for use of each of the entry guides.

A surgical system includes an entry guide. In one aspect, the entry guide has a first channel and a second channel. The surgical system also includes a first instrument with a first shaft, and a second instrument with a second shaft. A manipulator in the system is coupled to the first and second instruments.

The manipulator includes an instrument manipulator positioning system. The instrument manipulator positioning system is configured to move a first instrument mount interface for the first instrument and to move a second instrument mount interface for the second instrument so that a first shaft of a first instrument is positioned for insertion into the first channel of the entry guide, and so that a second shaft of a second instrument is positioned for insertion into the second channel of the entry guide. Thus, the movement of the two interfaces by the instrument manipulator positioning system effectively aligns the two shafts with the corresponding channels in the entry guide. In one aspect, the first and second instrument mount interfaces are moved before the first and second instruments are mounted on the respective interfaces. While two instruments are used as an example, in one aspect, the instrument manipulator positioning system can position any combination of a desired number of instruments so that shafts of the instruments can be inserted into corresponding channels in an entry guide.

As used herein, "align" does not require that a lengthwise axis of a channel and a lengthwise axis of the shaft be coincident. Rather, "align" means that the shaft is in position for entry into the channel without damage, and that the entry may require a non-permanent bend in the shaft. In some instances, however, the lengthwise axis of one or more instrument shafts and one or more corresponding entry guide channels are truly coincident, and so no shaft bending occurs. Thus in a first positioning state of two or more instruments, the instruments are positioned so that their shafts each enter, without bending, corresponding channels of a first entry guide arranged in a first configuration, and in a second positioning state of the two or more instruments, the instruments are positioned so that their shafts each enter, without bending, corresponding channels of a second entry guide arranged in a second configuration. Optionally, in the second positioning state of the two or more instruments, the instruments are positioned so that one or more of the instrument shafts bend as the shafts enter a corresponding channel of the second entry guide arranged in the second configuration. Thus, for various positioning states of the instruments with reference to corresponding entry guide configurations, various combinations of shaft bending or non-bending are made as needed, based on the instrument shafts and the entry guide channel configurations.

In one aspect, the instrument manipulator positioning system includes an adjustment gear that is coupled to each of the first instrument mount interface for the first instrument and the second instrument mount interface for the second instrument. In one aspect, movement of the adjustment gear simultaneously moves the first and second instrument mount interfaces into the positions where insertion of the shafts into the first and second channels is possible without damaging the instruments, e.g., the shafts of the first and second instruments are sufficiently aligned with the first and second channels, respectively, when the first and second instruments are mounted on the first and second instrument mount interfaces, respectively. In a further aspect, the instrument manipulator positioning system also includes a manually operated knob coupled to the adjustment gear. A user turns the knob which in turn causes the adjustment gear to rotate and move the instruments coupled to the adjustment gear. Again, the use of two instrument mount interfaces is an example and is not intended to be limiting. In general, the adjustment gear can be coupled to a number of instrument mount interfaces necessary to move instruments into a proper position for use with an entry guide of interest, e.g., four instrument mount interfaces.

In yet another aspect, a user manually moves each instrument mount interface of a plurality of instrument mount interfaces, as needed, in a direction perpendicular to a lengthwise axis of an entry guide to a proper location. A pin may be used to lock each instrument mount interface in the desired location. In some situations, not all of the plurality of instrument mount interfaces may need to be moved. The proper location for a particular instrument mount interface can be determined by a location of a through hole in a disk of the instrument manipulator positioning system, for example. Alternatively, the proper location can be determined by allowing the instrument mount interface to move to a location which minimizes any bend in the shaft of the instrument mounted to the instrument mount interface after the shaft is inserted into the entry guide with the lengthwise axis of the entry guide being vertical.

In yet another aspect, the instrument manipulator positioning system includes a first plurality of motors and a second plurality of motors. Each plurality of motors is coupled to a different instrument mount interface. Each plurality of motors positions the corresponding instrument mount interface for the instrument so that when the instrument is mounted on the instrument mount interface, the shaft of the instrument is aligned with a channel in an entry guide, e.g., the shaft can be positioned in the channel.

In still another aspect, the instrument manipulator positioning system further includes a first gearbox coupled to the first instrument, and a second gearbox coupled to the second instrument. A gear is coupled to the first and second gearboxes. As the gear is moved, the movement of the gear causes the first and second gearboxes to simultaneously move the first and second instrument mount interfaces into the positions where insertion of the shafts into the first and second channels is possible without damaging the instruments. In one aspect the gear is a roll gear, and another aspect the gear is an adjustment gear.

In one aspect, the first gearbox includes a gear having a side surface. A pin is coupled to the side surface of the gear. In one aspect, the pin has one degree of freedom. The pin is coupled to the instrument mount interface so that as the pin moves, the first instrument mount interface moves, and consequently a distal end of the shaft is effectively moved in the same arc as the pin. Here, "effectively moved" means that even though the entire instrument may not be mounted to the instrument mount interface when the instrument mount interface moves, when the entire instrument is mounted to the instrument mount interface, the location of the shaft relative to the entry guide has been moved compared to the location of the shaft relative to the entry guide if the instrument had been mounted before the instrument mount interface was moved.

In another aspect, the second gearbox includes a gear having a side surface. A pin is coupled to the side surface of the gear. The side surface of the gear of the second gearbox includes a cam. The pin rides on the cam. In one aspect, the pin has one degree of freedom, and in another aspect, the pin has two degrees of freedom. The pin is coupled to the second instrument mount interface so that as the pin moves, the second instrument mount interface moves, and consequently a distal end of the shaft of the second instrument is effectively moved with the same motion as the pin.

In yet another aspect, the entry guide includes first identification information and the first instrument includes second identification information. The apparatus includes a control system configured to receive the first identification information and to receive the second identification information. The control system configures the apparatus based on the first identification information, in one aspect.

An apparatus includes a first entry guide having a first channel configuration and a second entry guide having a second channel configuration. The first channel configuration is different from the second channel configuration.

The apparatus also includes a surgical system. Only one of the first entry guide and the second entry guide is mounted in the surgical system during a surgical procedure.

The surgical system includes an instrument having a shaft. An instrument manipulator positioning system is coupled to the instrument. Based on the channel configuration of the entry guide mounted in the surgical system, the instrument manipulator positioning system moves the instrument to a predetermined location to align the shaft with a channel of the entry guide, e.g., positions the shaft to enable insertion of the shaft into the channel of the entry guide. The predetermined location maintains bending stress on the shaft within a predetermined stress profile, in one aspect.

Since multiple entry guides with different channel configurations can be used in the surgical system, the instrument manipulator positioning system of the entry guide manipulator is configured to move a plurality of instrument mount interfaces to enable insertion of shafts of a first plurality of instruments into a first entry guide having a first channel configuration. The instrument manipulator positioning system is also configured to move the plurality of instrument mount interfaces to enable insertion of shafts of a second plurality of instruments into a second entry guide having a second channel configuration. The second channel configuration is different from the first channel configuration. The first plurality of instruments can be either the same as or different from the second plurality of instruments.

In one aspect, a method includes an instrument manipulator positioning system simultaneously moving a first instrument manipulator and a second instrument manipulator so that if a first instrument is mounted to the first instrument manipulator, a shaft of the first instrument is aligned with a first channel in a first entry guide, and so that if a second instrument is mounted to the second instrument manipulator, a shaft of the second instrument is aligned with a second channel of the first entry guide. The method also includes the instrument manipulator positioning system simultaneously moving the first instrument manipulator and the second instrument manipulator so that if a third instrument is mounted to the first instrument manipulator, a shaft of the third surgical instrument is aligned with a first channel in a second entry guide, and so that if a fourth instrument is mounted to the second instrument manipulator a shaft of the fourth instrument is aligned with a second channel of the second entry guide. A channel configuration of the first entry guide is different from a channel configuration of the second entry guide, and the first entry guide and the second single guide are used at different times.

In another aspect, a method includes moving an entry guide having a lengthwise axis so that the lengthwise axis is vertical. Then, a shaft of a surgical device assembly is inserted into a channel of the entry guide, and the entire surgical device assembly is allowed to move to a position of least energy. Finally, the surgical device assembly is locked to a disk.

In one aspect, the first entry guide has a circular cross section, and the second entry guide has a non-circular cross section. One or both of the first and second entry guides can include a manual instrument channel.

The apparatus also includes a first camera instrument having a first shaft with a first bend at a first location. The first camera instrument is mounted in the surgical system when the first entry guide is mounted in surgical system. A second camera instrument has a second shaft with a second bend at second location. The second camera instrument is mounted in the surgical system when the second entry guide is mounted in the surgical system. The first location is different from the second location.

In one aspect, a kit of entry guides includes a plurality of entry guides. Each entry guide includes a plurality of channels. A channel configuration of each entry guide is different from a channel configuration in each of the other entry guides in the plurality of entry guides. Each entry guide in the plurality is separately mountable in a same surgical system.

In one aspect, a first guide in the plurality includes a camera channel and a plurality of surgical instrument channels. A second entry guide in the plurality includes a camera channel and a manual instrument channel.

In another aspect, a first entry guide in the plurality includes a camera channel and a plurality of surgical instrument channels. A second entry guide in the plurality includes a camera channel and an advanced surgical instrument channel.

In still another aspect, a first entry guide includes a circular cross section. A second entry guide includes a non-circular cross section.

In still yet another aspect, a first entry guide in the plurality includes a camera channel and a plurality of surgical instrument channels. A second entry guide in the plurality has an oblong-shaped cross section. The oblong shape has a major axis. The second entry guide includes a camera channel having a first lengthwise axis, a first surgical instrument channel having a second lengthwise axis, and a second surgical instrument channel comprising a third lengthwise axis. A lengthwise axis extends from a proximal end of a channel to a distal end of the channel. The first, second, and third lengthwise axes intersect the major axis of the oblong cross section of the second entry guide.

In still a further aspect, a first entry guide in the plurality includes a camera channel and a plurality of surgical instrument channels. A second entry guide in the plurality includes a camera channel. The camera channel has an oblong-shaped cross section. The oblong-shaped cross section has a major axis and a minor axis. The second entry guide also includes a first surgical instrument channel having a first lengthwise axis, a second surgical instrument channel having a second lengthwise axis, and a third surgical instrument channel having a third lengthwise axis. The first lengthwise axis and the second lengthwise axis intersect a first line extending from the major axis. The first line includes the major axis. The third lengthwise axis intersects a second line extending from the minor axis. The second line includes the minor axis. The major axis is perpendicular to the minor axis, and so the first line is perpendicular to the second line.

The surgical system includes a manipulator system. The manipulator system includes a roll system couplable to first and second surgical device assemblies. The roll system is configured to roll the entire first and second surgical device assemblies as a group. The manipulator system also includes an instrument manipulator positioning system coupled to the roll system and couplable to the first and second surgical device assemblies. The instrument manipulator positioning system is configured to position first and second instrument interface assemblies for the first and second surgical device assemblies to enable insertion of shafts of the first and second surgical device assemblies into different channels of an entry guide.

The instrument manipulator positioning system includes an adjustment gear, and the roll system includes a roll ring gear. The manipulator system also includes a drive assembly. The drive assembly is coupled to the roll ring gear and coupled to the adjustment ring gear. The drive assembly is configured to differentially rotate the adjustment gear and the roll ring gear to cause the instrument manipulator positioning system to move the first and second instrument interface mounts for the surgical device assemblies to enable insertion of shafts of the surgical device assemblies into respective channels of an entry guide.

In one aspect, the drive assembly is configured to hold the roll ring gear stationary and is configured to turn the adjustment gear while the roll ring gear is held stationary. In another aspect, the drive assembly is configured to hold the adjustment gear stationary and is configured to turn the roll ring gear while the adjustment gear is held stationary.

BRIEF DESCRIPTION OF THE DRAWINGS

FIG. 2C is a schematic side view that illustrates aspects of a surgical system that includes an entry guide manipulator with an instrument manipulator positioning system.

FIG. 2D illustrates trajectories implemented in the instrument manipulator positioning system of FIG. 2C.

FIG. 5A is a schematic representation of four base assemblies mounted on the entry guide manipulator.

FIG. 5B is a cross sectional view of a first entry guide that is referred to as a standard entry guide.

FIG. 5C is a cross sectional view of a second entry guide.

FIG. 5D shows the first entry guide overlaid on the second entry guide.

FIG. 5E illustrates the result of the instrument manipulator positioning system in the entry guide manipulator moving the positioning element that is coupled to a surgical instrument.

FIG. 5F illustrates a plurality of, base assemblies having a hexagonal shape that could be mounted on and moved by the entry guide manipulator.

FIG. 6A is an illustration of one implementation of an instrument manipulator positioning system in the entry guide manipulator.

FIG. 6B is a cross-sectional view of an entry guide with at least one canted channel.

FIG. 6C is an illustration of another implementation of an instrument manipulator positioning system in the entry guide manipulator.

FIGS. 7A to 7C are a top, bottom, and oblique views respectively of one aspect of a portion of a base assembly that includes a floating platform.

FIG. 7D is a cut-away illustration of one aspect of a positioning element receptacle assembly.

FIG. 18F illustrates the seven locations for the instrument manipulator associated with the gearbox of FIGS. 11E to 11H.

FIG. 18G illustrates the seven locations of the output pin in the slot of FIG. 11G.

FIG. 18H illustrates the seven locations for the instrument manipulator associated with the gearbox of FIGS. 11I to 11J.

FIG. 18I illustrates the seven locations of the output pin in the slot of FIG. 11J.

FIGS. 21A and 21B are side views illustrating a first example of a way to attach base assemblies to a portion of the entry guide manipulator.

FIG. 22A is a side view illustrating a second example of a way to attach base assemblies to a portion of the entry guide manipulator.

FIGS. 22B and 22C are top views of the second example of FIG. 22A.

FIGS. 23A and 23B are side views illustrating a third example of a way to attach base assemblies to a portion of the entry guide manipulator.

Figure 1A:
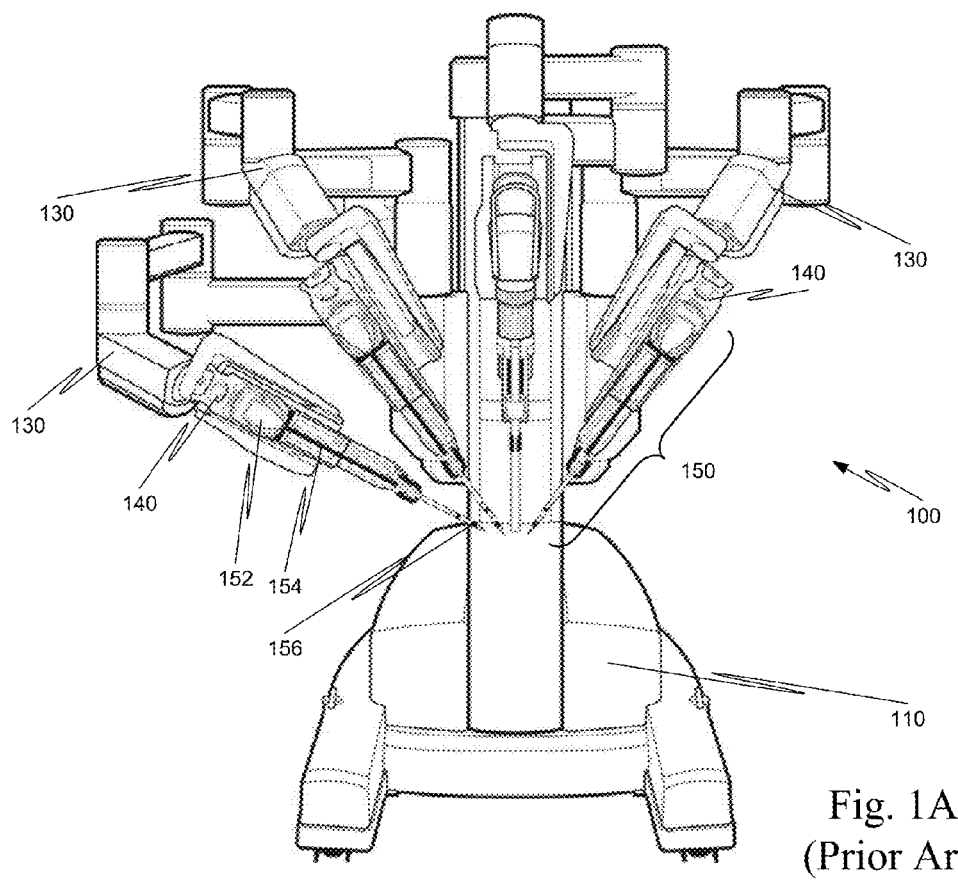
FIG. 1A is an illustration of a portion of a prior art surgical system.
Figure 1B:
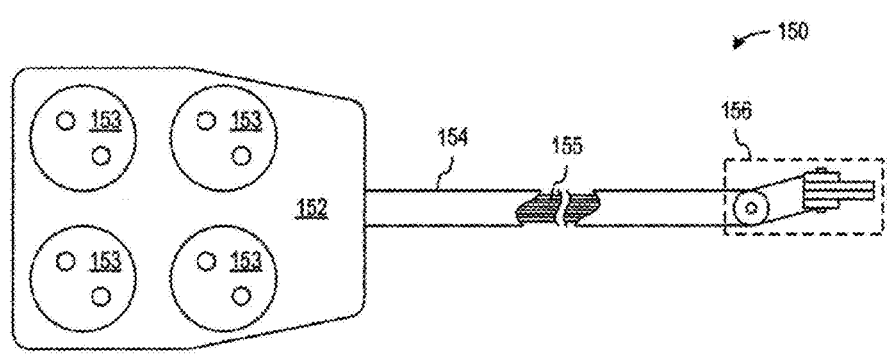
FIG. 1B is an illustration of a prior art surgical device assembly.

In the drawings, for single digit figure numbers, the first digit in the reference numeral of an element is the number of the figure in which that element first appears. For double-digit figure numbers, the first two digits in the reference numeral of an element is the number of the figure in which that element first appears.

DETAILED DESCRIPTION

A surgical system, e.g., a teleoperated, computer-assisted surgical system, with a single entry port is used in a wide variety of different surgeries. The variety of surgical procedures uses various combinations of instruments that enter a patient through the single entry port. The instruments, in one aspect, are grouped into sets of instruments based on the shaft characteristics of the instruments, e.g., standard surgical instruments, advanced surgical instruments, and camera instruments. These instruments can be manually controlled, controlled with computer assistance (fully or cooperatively controlled), or teleoperatively controlled.

The different surgeries that can be performed using the single entry port may be performed on different regions of the body. For example, one surgery may be performed through the mouth of a patient; another surgery may be performed between the ribs of a patient; and other surgeries may be performed through other orifices of a patient or through an incision in the patient. Not only is the surgical system configured to use a variety of instruments, but also the surgical system is configured to use a variety of different entry guides. Typically, a different entry guide is used for each different type of surgery. The entry guide selected for a particular surgical procedure may maintain an insufflation seal, if necessary, and the entry guide supports the shafts of the instruments at the entry point into the body of the patient.

A single entry port means that a single incision in a patient or a single bodily orifice of the patient is used to perform the surgical procedure. While a single entry port surgical system is used as an example, this example is not intended to limit the aspects described below to surgical systems that utilize a single entry port. The aspects described below can be used in any surgical system that inserts multiple instruments into a patient through a single entry guide. For example, if a surgical system utilizes two or more entry ports into a patient, and an entry guide having a plurality of channels is used in any of or all of the two or more entry ports, the aspects described below are directly applicable to such a surgical system.

Figure 2A:
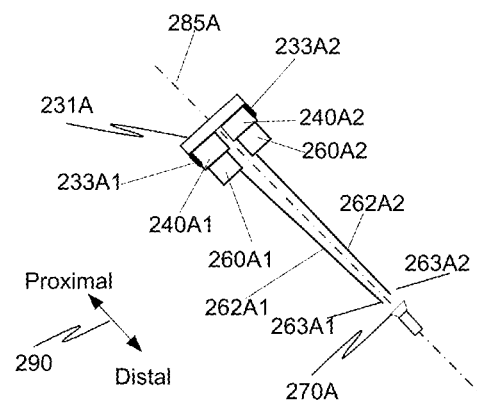
FIG. 2A is a schematic illustration of an instrument manipulator positioning system and a plurality of surgical device assemblies coupled to the instrument manipulator positioning system.

FIG. 2A is a schematic illustration of a plurality of surgical device assemblies in a surgical system. A first surgical device assembly includes a first instrument manipulator 240A1 and a first instrument 260A1. First instrument 260A1 is mounted to first instrument manipulator 240A1. First instrument 260A1 includes a shaft 262A1 that extends in a distal direction from a body of first instrument 260A1. The surgical device assembly including first instrument 260A1 is coupled to an instrument manipulator positioning system 231A by a first longitudinal motion mechanism 233A1. Longitudinal motion mechanism 233A1 moves the first surgical device assembly in a proximal direction and in a distal direction. A second surgical device assembly includes a second instrument manipulator 240A2 and a second instrument 260A2. Second instrument 260A2 is mounted to second instrument manipulator 240A2. Second instrument 260A2 includes a shaft 262A2 that extends in a distal direction from a body of second instrument 260A2. The second surgical device assembly including second instrument 260A2 is coupled to instrument manipulator positioning system 231A2 by a second longitudinal motion mechanism 233A2. Longitudinal motion mechanism 233A2 moves the second surgical device assembly in a proximal direction and in a distal direction.

To insert multiple instruments 260A1, 260A2 into a patient through a single entry port may require one or more of shafts 262A1, 262A2 of instruments 260A1, 260A2 to bend between where the shaft is connected to the body of the instrument and the point where the shaft contacts a channel of the entry guide 270A. If the shaft of the instrument is bent too much, the shaft of the instrument may be damaged and/or the instrument may not perform properly during the surgery.

Thus, in one aspect, each entire instrument 260A1, 260A2 (FIG. 2A) is positioned by an instrument manipulator positioning system 231A, which in some aspects is part of an entry guide manipulator, so that when each shaft 262A1, 262A2 is inserted in a corresponding channel of entry guide 270A, any bending of the shaft is not permanent and does not inhibit proper operation of the instrument. This assures that any bending does not damage the instrument and that any bending does not affect the correct operation of the instrument.

In one aspect, for each entry guide with a different channel configuration, instrument manipulator positioning system 231A moves at least one instrument mount interface 240A1_IMI for an instrument 260A1 so that stresses induced by any bend in shaft 262A1 remains within a predetermined stress profile, e.g., the stress on shaft 262A1 is controlled such that shaft 262A1 does not yield and permanently change shape. Additionally, the stress is maintained so that as shaft 262A1 rolls in entry guide 270A, the cycling stress does not fatigue and break shaft 262A1. This cycling stress load can be a consideration associated with instrument life.

In one aspect, each instrument mount interface is configured to couple an instrument to an instrument manipulator and to support that instrument while coupled. For example, a first instrument mount interface 240A1_IMI supports instrument 260A1 and couples instrument 260A1 to instrument manipulator 240A1, and a second instrument mount interface 240A2_IMI supports instrument 260A2 and couples instrument 260A2 to instrument manipulator 240A2.

For a first entry guide having a first channel configuration, instrument manipulator positioning system 231A has a first state, and for a second entry guide having a second channel configuration, instrument manipulator positioning system 231A has a second state. The first channel configuration is different from the second channel configuration.

In the first state, instrument manipulator positioning system 231A moves instrument mount interface 240A1_IMI, by moving longitudinal motion mechanism 233A1 and consequently instrument manipulator 240A1, so that when instrument 260A1 is mounted on instrument mount interface 240A1_IMI, a distal end 263A1 of shaft 262A1 is aligned with a corresponding channel in the first channel configuration.

In the second state, instrument manipulator positioning system 231A moves instrument mount interface 240A1_IMI so that when instrument 260A1 is mounted on instrument mount interface 240A1_IMI, a distal end 263A1 of shaft 262A1 is aligned with a corresponding channel in the second channel configuration. If in either the first state or the second state, the shaft is bent upon passing through entry guide 270A, the shaft is aligned with the corresponding channel in the entry guide prior to passing though entry guide 270A so that any bending does not damage the instrument and does not inhibit proper operation of the instrument. Here, the corresponding channel in the channel configuration is the channel through which the shaft passes.

Figure 2B:
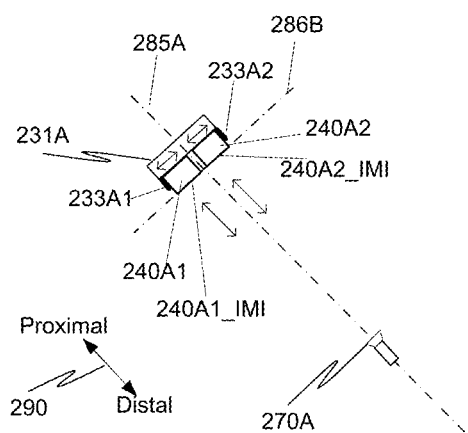
FIG. 2B is a schematic illustration of an instrument manipulator positioning system and a plurality of instrument manipulators before instruments have been coupled to the plurality of instrument manipulators.

Thus, in the first state, at least a portion of instrument mount interface 240A1_IMI is at a first location in a plane 286B (FIG. 2B). Plane 286B is perpendicular to a longitudinal axis 285A of entry guide 270A. In the second state, the portion of instrument mount interface 240A1_IMI is moved to a second location in plane 286B, where the second location is different from the first location. Note that when the portion of instrument mount interface 240A1_IMI moves in plane 286B, a portion of instrument manipulator 240A1 also moves in a plane that is parallel to plane 286B.

Numerous examples are presented below of aspects of instrument manipulator positioning system 231A that move one or more instrument mount interfaces in a plane that is perpendicular to the longitudinal axis of the entry guide. The movement, in one aspect, is in one dimension of plane 286B and in other aspects, the movement is in two dimensions of plane 286B. Each aspect described below of an instrument manipulator positioning system has at least one of the two states described here, and each aspect illustrates a different way to implement the or each of the two states. In addition, instrument manipulator positioning system 231A can be implemented having manual control of the movement of the instrument mount interfaces or having automatic control of the movement of the instrument mount interfaces.

In one aspect, instrument manipulator positioning system 231A simultaneously moves instrument interface mounts 240A1_IMI, 240A2_IMI for instruments 260A1, 260A2 with respect to the channels in entry guide 270A, if necessary, so that when shafts 262A1, 262A2 of instruments 260A1, 260A2 are passed through channels of entry guide 270, any bending of instrument shafts 262A1, 262A2 does not damage the instruments and does not inhibit operation of instruments 260A1, 260A2. As explained above, in some instance, a shaft of an instrument may pass through a channel of the entry guide without any bending. If an instrument shaft is bent to the point that the shaft does not return to its original shape when withdrawn from entry guide 270, the instrument is considered damaged. In this aspect, instrument manipulator positioning system 231A is configured to move each instrument mount interface as required for each entry guide in a family of entry guides, and in one aspect, the adjustment is made with little or no user input.

In one aspect, instrument manipulator positioning system 231A moves instrument mount interfaces 240A1_IMI 240A2_IMI, as needed, before instruments 260A1, 260A2 are mounted on instrument manipulator positioning system 231A. In one aspect, instrument manipulator positioning system 231A is one integral system. In another aspect, there is an individual instrument manipulator positioning system 231A for each instrument. Irrespective of the implementation of system 231A, the operation is as described herein.

As described above, instrument manipulator positioning system 231A is configured to move a first instrument mount interface 240A1_IMI for first instrument 260A1 and to move second instrument mount interface 240A1_IMI for the second instrument 260A2 in a plane 286B so that first shaft 262A1 is positioned for insertion into a first channel of entry guide 270A, and so that second shaft 262A2 is positioned for insertion into a second channel of entry guide 270A. The first and second channels are different channels. Thus, the movement of the two interfaces by instrument manipulator positioning system 231A effectively aligns the two shafts, e.g., aligns the distal end of the two shafts, with the corresponding channels in entry guide 270A.

As used herein, "align" does not require that a lengthwise axis of a channel and a lengthwise axis of the shaft be coincident. Rather, "align" means that the shaft is in position for entry into the channel without damage and that the entry may require a non-permanent bend in the shaft. In some instances, however, the lengthwise axis of one or more instrument shafts and one or more corresponding entry guide channels are truly coincident, and so no shaft bending occurs. Thus, in a first positioning state of two or more instruments, the instruments are positioned so that their shafts each enter, without bending, corresponding channels of a first entry guide arranged in a first configuration, and in a second positioning state of the two or more instruments, the instruments are positioned so that their shafts each enter, without bending, corresponding channels of a second entry guide arranged in a second configuration. Optionally, in the second positioning state of the two or more instruments, the instruments are positioned so that one or more of the instrument shafts bend as the shafts enter a corresponding channel of the second entry guide arranged in the second configuration. Thus, for various positioning states of the instruments with reference to corresponding entry guide configurations, various combinations of shaft bending or non-bending are made as needed, based on the instrument shafts and the entry guide channel configurations.

In one aspect described below, instrument manipulator positioning system 231A includes an adjustment gear that is coupled to each of the first instrument mount interface for the first instrument and the second mount interface for the second instrument. In one aspect, movement of the adjustment gear simultaneously moves the first and second instrument mount interfaces into the positions where insertion of the shafts into the first and second channels is possible without damaging the instruments, e.g., the shafts of the first and second instruments are aligned with the first and second channels, respectively when the first and second instruments are mounted on the first and second instrument mount interfaces, respectively. In a further aspect, instrument manipulator positioning system 231A also includes a manually operated knob coupled to the adjustment gear. A user turns the knob which in turn causes the adjustment gear to rotate and move the surgical instruments coupled to the adjustment gear. Alternatively, a user manually moves each instrument mount interface to the proper location and uses a pin to lock the instrument mount interface in that location, for example the instrument manipulator is locked to a disk in instrument manipulator positioning system 231A.

In one aspect, instrument manipulator positioning system 231A, sometimes referred to as system 231A, includes a plurality of movable platforms, one for each of a plurality of instruments that are coupled to system 231A. In one aspect, each moveable platform is connected to a longitudinal motion mechanism, e.g., a first moveable platform is coupled to longitudinal motion mechanism 233A1 and a second movable platform is coupled to longitudinal motion mechanism 233A2. Various examples of movable platforms are presented below.

Each longitudinal motion mechanism is connected to an instrument manipulator assembly, e.g., longitudinal motion mechanism 233A1 is connected to instrument manipulator assembly 240A1, and longitudinal motion mechanism 233A2 is connected to instrument manipulator assembly 240A2. Each longitudinal motion mechanism moves the connected instrument manipulator assembly in a proximal direction and in a distal direction, e.g. in a first direction and a second direction along an extended lengthwise axis 285A of entry guide 270A.

Each instrument manipulator assembly includes an instrument manipulator interface on a distal face of the instrument manipulator assembly, in one aspect. Each instrument manipulator assembly also includes a plurality of motors that drive elements of an instrument attached to the instrument manipulator interface.

In one aspect, instrument manipulator positioning system 231A includes a lateral motion mechanism. The lateral motion mechanism is coupled to each of the movable platforms, i.e., coupled to each of the plurality of instrument manipulator assemblies, e.g., instrument manipulator assembly 240A1 and instrument manipulator assembly 240A2. The lateral motion mechanism moves the plurality of instrument manipulator assemblies in plane 286B, i.e., the lateral motion mechanism moves an instrument manipulator assembly in a plane that is perpendicular to the direction of motion, as represented by arrow 290, provided by a longitudinal motion mechanism. Various examples of the lateral motion mechanism are described below. Thus, a lateral motion mechanism causes an instrument mount interface to be moved laterally, i.e., in a direction perpendicular to extended lengthwise axis 285A, sometimes referred to as lengthwise axis 285A, of entry guide 270A. In one aspect, the lateral motion is motion in a plane perpendicular to extended lengthwise axis 285A.

FIG. 2C is a schematic side view that illustrates aspects of a surgical system 200C that uses aspects of instruments, surgical device assemblies, and manipulation and control systems described herein. The three main components are an endoscopic imaging system 292, a surgeon's console 294 (master), and a patient side support system 210C (slave), all interconnected by wired (electrical or optical) or wireless connections 296. One or more electronic data processors may be variously located in these main components to provide system functionality. Examples are disclosed in U.S. patent application Ser. No. 11/762,165, which is incorporated by reference herein.

Patient side support system 210C includes an entry guide manipulator 230C. At least one surgical device assembly is coupled to entry guide manipulator 230C. Each surgical device assembly includes either a surgical instrument or a camera instrument. For example, in FIG. 2C, one surgical device assembly includes an instrument 260C1 with a shaft 262C2 that extends through entry guide 270C during a surgical procedure.

Entry guide manipulator 230C includes, as described more completely below, an instrument manipulator positioning system 231C, sometimes referred to as positioning system 231C or system 231C. Positioning system 231C moves a portion of each of the instrument mount interfaces in a plane so that when each of the instruments is coupled to entry guide manipulator 230C using the instrument mount interfaces, each of the shafts of the instruments is aligned for insertion into one of the channels in entry guide 270C. Typically, entry guide 270C includes a plurality of channels. Thus, instrument manipulator positioning system 231C effectively moves the shafts of the instruments by moving each instrument in a plurality of instruments, as needed, to align each of the shafts for entry into a channel in a particular entry guide channel configuration.

Thus, in one aspect, an instrument mount interface is moved so that when an instrument is attached to that instrument mount interface, a shaft of the instrument is properly aligned with a channel in an entry guide used in the surgical procedure. In another aspect, the instrument is mounted on the instrument mount interface, and then the instrument mount interface is moved. The movement of the instrument mount interfaces moves the entire instrument so that the shaft of the instrument is properly aligned with the channel in the entry guide used in the surgical procedure. Consequently, the movement of the instrument mount interface is the same irrespective of whether the instrument is mounted before or after the movement of the instrument mount interface.

In one aspect, positioning elements of instrument manipulator positioning system 231C, e.g., positioning elements of a lateral motion mechanism of system 231C, move in a plane to simultaneously move the instrument mount interfaces and consequently move each instrument to the appropriate location for entry of that instrument's shaft into entry guide 270C. The path of the movement in the plane, sometimes called a trajectory, can be, for example, an arc, a straight line, a meandering combination of arcs, or some combination of curved paths and lines. Thus, the trajectory can have either one degree of freedom or two degrees of freedom. The plane is perpendicular to the lengthwise axis of entry guide 270C, in one aspect. Thus, in this aspect, each of the trajectories is in a plane perpendicular to the lengthwise axis, sometimes referred to as the longitudinal axis, of entry guide 270C See FIG. 2D for examples of typical trajectories 226, 227, 228, and 229.

As a positioning element moves along a trajectory, the instrument mount interface is moved along the same trajectory, and effectively a distal tip of a shaft of an instrument coupled to the instrument mount interface moves along the same trajectory. Thus, motion of the positioning element causes the shaft to be moved to a location where the shaft is aligned with a channel in entry guide 270C. In this position, the shaft can enter and pass through the channel in entry guide 270C without damaging the instrument and without inhibiting operation of the instrument. The particular paths implemented in instrument manipulator positioning system 231C depend at least in part on the types of surgical device assemblies that can be mounted on system 231C and/or the configuration of channels in entry guide 270C.

As explained more completely below, different entry guides are used in different surgical procedures. An entry guide that enters the body through the ribs typically has a different shape than an entry guide that enters the body through an incision in the abdomen. The different shapes of the entry guides require different layouts of the channels that extend through the entry guides, i.e., different channel configurations.

Also, the shapes and/or sizes of the shafts of the instruments may be different for different instruments. An entry guide is used that accommodates the shapes and sizes of the shafts of the instruments used in a particular surgical procedure. The trajectories, such as those illustrated in FIG. 2D, are designed to accommodate a set of entry guides that can be used with patient side support system 210C.

When an entry guide, such as entry guide 270C, is mounted on entry guide manipulator 230C, and an instrument, e.g., instrument 260C1, is mounted on entry guide manipulator 230C, a control system determines whether shaft 262C1 of instrument 260C1 can be, or has been, aligned by instrument manipulator positioning system 231C with a channel in entry guide 270C. If instrument manipulator positioning system 231C cannot properly align shaft 262C1, an alarm is activated and the system rejects instrument 260C1.

Instrument manipulator positioning system 231C can properly align shaft 262C1 if system 231C can move the instrument mount interface and consequently the entire surgical device assembly to a location so that when shaft 262C1 passes through the corresponding channel in entry guide 270C, instrument 260C1 is not damaged. Typically, instrument 260C1 not being damaged means that shaft 262C1 is not bent to the point that the shaft is damaged, e.g., permanently bent, and/or that operation of elements passing though shaft 262C1 is not hindered during operation of instrument 260C1.

In one aspect, at least one of the surgical device assemblies in plurality of surgical device assemblies 280C includes a shaft with a portion that is rigid, but this rigid portion can be resiliently bent between entry guide 270C and the proximal end of the shaft. Arrow 290 defines the distal and proximal directions. In one aspect, each surgical device assembly in plurality of surgical device assemblies 280C is positioned by instrument manipulator positioning system 231C to maintain the bending stress or stresses on the instrument shaft within a predetermined stress profile. This assures that the instrument shaft and thus the instrument is not damaged by the bending, e.g., the stress on the shaft is controlled such that the shaft does not yield and permanently change shape. Additionally, the stress is maintained so that as the shaft rolls in entry guide 270C, the cycling stress does not fatigue and break the shaft.

The ability to individually position an instrument, and hence its shaft, with respect to a channel in an entry guide by moving an instrument mount interface provides versatility to patient side support system 210C. For example, this ability allows entry guides with different channel configurations to be used in system 210C. In addition, the instrument manipulator positioning system eliminates the need for surgical procedure specific instruments. In other words, the instrument manipulator positioning system allows use of a common set of instruments with a variety of entry guides by moving the instrument shafts around, as described herein.

Prior to considering entry guide manipulator 230C with instrument manipulator positioning system 231C in further detail, other aspects of system 200C are described. Imaging system 292 performs image processing functions on, e.g., captured endoscopic imaging data of the surgical site and/or preoperative or real time image data from other imaging systems external to the patient. Imaging system 292 outputs processed image data (e.g., images of the surgical site, as well as relevant control and patient information) to a surgeon at surgeon's console 294. In some aspects, the processed image data is output to an optional external monitor visible to other operating room personnel or to one or more locations remote from the operating room (e.g., a surgeon at another location may monitor the video; live feed video may be used for training; etc.).

Surgeon's console 294 includes multiple degrees-of-freedom ("DOF") mechanical input devices ("masters") that allow the surgeon to manipulate the instruments, entry guide(s), and imaging system devices, which are collectively referred to as slaves. These input devices may in some aspects provide haptic feedback from the instruments and surgical device assembly components to the surgeon. Console 294 also includes a stereoscopic video output display positioned such that images on the display are generally focused at a distance that corresponds to the surgeon's hands working behind/below the display screen. These aspects are discussed more fully in U.S. Pat. No. 6,671,581, which is incorporated by reference herein.

Control during insertion of the instruments may be accomplished, for example, by the surgeon moving the instruments presented in the image with one or both of the masters; the surgeon uses the masters to move the instrument in the image side to side and to pull the instrument towards the surgeon. The motion of the masters commands the imaging system and an associated surgical device assembly to steer towards a fixed center point on the output display and to advance inside the patient. In one aspect, the camera control is designed to give the impression that the masters are fixed to the image so that the image moves in the same direction that the master handles are moved. This design causes the masters to be in the correct location to control the instruments when the surgeon exits from camera control, and consequently this design avoids the need to clutch (disengage), move, and declutch (engage) the masters back into position prior to beginning or resuming instrument control. In some aspects the master position may be made proportional to the insertion velocity to avoid using a large master workspace. Alternatively, the surgeon may clutch and declutch the masters to use a ratcheting action for insertion. In some aspects, insertion may be controlled manually (e.g., by hand operated wheels), and automated insertion (e.g., servomotor driven rollers) is then done when the distal end of the surgical device assembly is near the surgical site. Preoperative or real time image data (e.g., MRI, X-ray) of the patient's anatomical structures and spaces available for insertion trajectories may be used to assist insertion.

Patient side support system 210C includes a floor-mounted base 201C, or alternately a ceiling mounted base (not shown). Base 201C may be movable or fixed (e.g., to the floor, ceiling, wall, or other equipment such as an operating table).

Base 201C supports an arm assembly that includes a passive, uncontrolled setup arm assembly 220C and an actively controlled manipulator arm assembly 230C. The actively controlled manipulator arm assembly 230C is referred to as entry guide manipulator 230C.

In one example, the setup portion includes a first setup link 202C and two passive rotational setup joints 203C and 205C. Rotational setup joints 203C and 205C allow manual positioning of the coupled setup links 204C and 206C if the joint brakes for setup joints 203C and 205C are released. Alternatively, some of these setup joints may be actively controlled, and more or fewer setup joints may be used in various configurations. Setup joints 203C and 205C and setup links 204C and 206C allow a person to place entry guide manipulator 230C at various positions and orientations in Cartesian x, y, z space. A passive prismatic setup joint (not shown) between link 202C of arm assembly 220C and base 201C may be used for large vertical adjustments 212C.

Remote center of motion 246C is the location at which yaw, pitch, and roll axes intersect (i.e., the location at which the kinematic chain remains effectively stationary while joints move through their range of motion). As described in more detail below, some of these actively controlled joints are manipulators that are associated with controlling DOFs of individual instruments, and others of these actively controlled joints are associated with controlling DOFs of a single assembly of these manipulators. The active joints and links are movable by motors or other actuators and receive movement control signals that are associated with master arm movements at surgeon's console 294.

As shown in FIG. 2C, a manipulator assembly yaw joint 211C is coupled between an end of setup link 206C and a first end, e.g., a proximal end, of a first manipulator link 213C. Yaw joint 211C allows first manipulator link 213C to move with reference to link 206C in a motion that may be arbitrarily defined as "yaw" around a manipulator assembly yaw axis 223C. As shown, the rotational axis of yaw joint 211C is aligned with a remote center of motion 246C, which is generally the position at which an instrument enters the patient (e.g., at the umbilicus for abdominal surgery).

In one embodiment, setup link 206C is rotatable in a horizontal or x, y plane and yaw joint 211C is configured to allow first manipulator link 2130 in entry guide manipulator 230C to rotate about yaw axis 223C. Setup link 206C, yaw joint 211C, and first manipulator link 213C provide a constantly vertical yaw axis 223C for entry guide manipulator 230C, as illustrated by the vertical line through yaw joint 211C to remote center of motion 246C.

A distal end of first manipulator link 213C is coupled to a proximal end of a second manipulator link 215C by a first actively controlled rotational joint 214C. A distal end of second manipulator link 215C is coupled to a proximal end of a third manipulator link 217C by a second actively controlled rotational joint 216C. A distal end of third manipulator link 217C is coupled to a distal portion of a fourth manipulator link 219C by a third actively controlled rotational joint 218C.

In one embodiment, links 215C, 2170, and 219C are coupled together to act as a coupled motion mechanism. Coupled motion mechanisms are well known (e.g., such mechanisms are known as parallel motion linkages when input and output link motions are kept parallel to each other). For example, if rotational joint 214C is actively rotated, then joints 216C and 218C are also actively rotated so that link 219C moves with a constant relationship to link 215C. Therefore, it can be seen that the rotational axes of joints 214C, 216C, and 218C are parallel. When these axes are perpendicular to rotational axis 223C of joint 211C, links 215C, 217C, and 219C move with reference to link 213C in a motion that may be arbitrarily defined as "pitch" around a manipulator assembly pitch axis. The manipulator pitch axis extends into and out of the page in FIG. 2C at remote center of motion 246C in this aspect. The motion around the manipulator assembly pitch axis is represented by arrow 221C. Since links 215C, 217C, and 219C move as a single assembly in this embodiment, first manipulator link 213C may be considered an active proximal manipulator link, and second through fourth manipulator links 215C, 217C, and 219C may be considered collectively an active distal manipulator link.

An entry guide manipulator assembly platform 232C, sometimes referred to as platform 232C, is coupled to a distal end of fourth manipulator link 219C. An entry guide manipulator assembly 233C is rotatably mounted on platform 232C. Entry guide manipulator assembly 233C includes instrument manipulator positioning system 231C.

Each of plurality of surgical device assemblies 280C is coupled to entry guide manipulator assembly 233C by an insertion assembly 235C. Entry guide manipulator assembly 233C rotates plurality of surgical device assemblies 280C as a group around axis 225C. Specifically, entry guide manipulator assembly 233C rotates as a single unit with reference to platform 232C in a motion that may be arbitrarily defined as "roll" around an entry guide manipulator assembly roll axis 225C.

For minimally invasive surgery, the instruments must remain substantially stationary with respect to the location at which the instruments enter the patient's body, either at an incision or at a natural orifice, to avoid unnecessary tissue damage. Accordingly, the yaw and pitch motions of the instruments should be centered around a single location on manipulator assembly roll axis 225C that stays relatively stationary in space. This location is referred to as remote center of motion 246C.

For single port surgery, in which all the instruments (including a camera instrument) must enter via a single small incision (e.g., at the umbilicus) or natural orifice, all instruments must move with reference to such a generally stationary remote center of motion 246C. Therefore, remote center of motion 246C of entry guide manipulator 230C is defined by the intersection of manipulator assembly yaw axis 223C and manipulator assembly pitch axis 221C. The configuration of links 215C, 217C, and 219C, and the configuration of joints 214C, 216C, and 218C are such that remote center of motion 246C is located distal of entry guide manipulator assembly 233C with sufficient distance to allow entry guide manipulator assembly 233C to move freely with respect to the patient. Manipulator assembly roll axis 225C also intersects remote center of motion 246C.

Cannula 275C is removably coupled to a cannula mount, which in one embodiment is coupled to the distal end 219C_P of fourth manipulator link 219C. In one implementation, the cannula mount is coupled to link 219C by a rotational joint that allows the mount to move between a stowed position adjacent link 219C and an operational position that holds the cannula in the correct position so that remote center of motion 246C is located along the cannula. During operation, the cannula mount is fixed in position relative to link 219C according to one aspect.

In this description, a cannula is typically used to prevent an instrument or an entry guide from rubbing on patient tissue. Cannulas may be used for both incisions and natural orifices. For situations in which an instrument or an entry guide does not frequently translate or rotate relative to its insertion (longitudinal) axis, a cannula may not be used. For situations that require insufflation, the cannula may include a seal to prevent excess insufflation gas leakage past the instrument or entry guide. Examples of cannula assemblies which support insufflation and procedures requiring insufflation gas at the surgical site may be found in U.S. patent application Ser. No. 12/705,439 (filed Feb. 12, 2010; disclosing "Entry Guide for Multiple Instruments in a Single Port System"), the full disclosure of which is incorporated by reference herein for all purposes. For thoracic surgery that does not require insufflation, the cannula seal may be omitted, and if instruments or entry guide insertion axis movement is minimal, then the cannula itself may be omitted. A rigid entry guide may function as a cannula in some configurations for instruments that are inserted relative to the entry guide. Cannulas and entry guides may be, e.g., steel or extruded plastic. Plastic, which is less expensive than steel, may be suitable for one-time use.

The various passive setup joints/links and active joints/links allow positioning of the instrument manipulators to move the instruments and imaging system with a large range of motion when a patient is placed in various positions on a movable table. In some embodiments, a cannula mount may be coupled to the proximal link or first manipulator link 213C.

Certain setup and active joints and links in the manipulator arm may be omitted to reduce the surgical system's size and shape, or joints and links may be added to increase degrees of freedom. It should be understood that the manipulator arm may include various combinations of links, passive joints, and active joints (redundant DOFs may be provided) to achieve a necessary range of poses for surgery. Furthermore, various instruments alone or surgical device assemblies including entry guides, multiple instruments, and/or multiple entry guides, and instruments coupled to instrument manipulators (e.g., actuator assemblies) via various configurations (e.g., on a proximal face or a distal face of the instrument transmission means or the instrument manipulator), are applicable in aspects of the present disclosure.

Each of plurality of surgical device assemblies 280C includes an instrument manipulator assembly and one of a surgical instrument and a camera assembly. In FIG. 2C, two of a plurality of surgical device assemblies 280C are visible, and each of the two visible surgical device assemblies includes an instrument manipulator assembly and an instrument. Each of instrument manipulator assemblies 240C1 and 240C2 is teleoperated, in one aspect, and so each is sometimes referred to as a teleoperated instrument manipulator assembly. Each of instrument manipulator assemblies 240C1, 240C2 is coupled to entry guide manipulator assembly 233C by an different insertion assembly, e.g. instrument manipulator assembly 240C1 is coupled to entry guide manipulator assembly by insertion assembly 235C.

In one aspect, insertion assembly 235C is a telescoping assembly that moves the corresponding surgical device assembly away from and towards entry guide manipulator assembly 230C. In FIG. 2C, insertion assembly 235C is in the fully retracted position.

Each instrument manipulator assembly 240C1, 240C2 includes a plurality of motors that drive a plurality of outputs in an output interface of instrument manipulator assembly 240C1, 240C1. Each of instruments 260C1, 260C2 includes a body that houses a transmission unit. The transmission unit includes an input interface including a plurality of inputs. Each of instruments 260C1, 260C2 also includes a shaft 262C1, 262C2 sometimes referred to as a main tube that extends in the distal direction from the body. An end effector 263C is coupled to a distal end of the shaft. See U.S. Patent Application No. 61/866,115 (filed on 15 Aug. 2013), which is incorporated by reference, for one example of an instrument manipulator assembly and a surgical instrument.

Each of instruments 260C1, 260C2 is coupled to the instrument mount interface of a corresponding instrument manipulator assembly 240C1, 240C2 so that a plurality of inputs in an input interface of the transmission unit in instrument 260C1, 260C2 are driven by plurality of outputs in the instrument mount interface of instrument manipulator assembly 240C1, 240C2. See U.S. Patent Application No. 61/866,115 (filed on 15 Aug. 2013).

In one aspect, a membrane interface that is part of a sterile surgical drape may be placed between the instrument mount interface of instrument manipulator assembly 240C and the input interface of the transmission unit in instrument 260C. See, for example, U.S. Patent Application Publication No. US 2011/0277776 A1 for an example of the membrane interface and sterile surgical drape. In another aspect, a sterile adapter that is part of a sterile surgical drape may be placed between the instrument mount interface of instrument manipulator assembly 240C and the input interface of the transmission unit in instrument 260C. See, for example, U.S. Patent Application Publication No. US 2011/0277775 A1 for an example of a sterile adapter and a sterile surgical drape.

In one aspect, one or more instrument manipulator assemblies may be configured to support and actuate a particular type of instrument, such as a camera instrument. As shown in FIG. 2C, the shafts of plurality of surgical device assemblies 280C extend distally from a body of the instruments. The shafts extend through a common cannula 275C placed at the entry port into the patient (e.g., through the body wall or at a natural orifice). In one aspect, an entry guide 270C is positioned within cannula 275C, and each instrument shaft extends through a channel in entry guide 270C, so as to provide additional support for the instrument shafts.

The surgeries that can be performed using surgical system 200C may be performed on different regions of the body. For example, one surgery may be performed through the mouth of a patient. Another surgery may be performed between the ribs of the patient. Other surgeries may be performed through other orifices of the patient or through an incision in the patient. Each different entry into a patient may require a different shape and/or different size of an entry guide. Thus, an appropriate guide 270C is selected for a particular surgery.

An entry guide, which is suitable for abdominal surgery, may not be suitable for surgery through the mouth or between the ribs. The size and shape of an entry guide limits the locations of channels through the entry guide for shafts 262C1, 262C2 of plurality of surgical device assemblies 280C. Thus, instrument manipulator positioning system 231C moves each of instrument manipulator assemblies 240C1, 240C2 and corresponding instrument 260C1, 260C2 so that each of shafts 262C1, 262C2 is properly aligned for entry into a different channel of entry guide 270C. In one aspect, instrument manipulator positioning system 231C moves each of instrument manipulator assemblies 240C1, 240C2 and corresponding instrument 260C1, 260C2 to align shaft 262C1, 262C2 so that any bend in shaft 262C1, 262C2 between a proximal end of the shaft and a point of contact of the shaft with entry guide 270C as the shaft passes through entry guide 270C does not damage the instrument and does not inhibit operation of the instrument. Thus, not only is system 200C configured to use a variety of instruments, but also system 200C is configured to use a variety of different entry guides. Various combinations of these different entry guides are provided in kits.

FIG. 2D is an illustration of example paths 226 to 229 along which a different one of plurality of surgical device assemblies 280C can be moved by instrument manipulator positioning system 231C. In this example, three of the paths 227 to 229 are curved paths and one of the paths 226 is a linear path. In one aspect, linear path 226 is used for a camera instrument and the three curved paths 227 to 229 are used for surgical instruments. Each entry guide that can be used with system 200C has a channel positioned so that a surgical device assembly positioned on one of the four paths can pass the shaft of that surgical device assembly through that channel and work correctly for that instrument's intended purpose. In one aspect, instrument manipulator positioning system 231C automatically moves each of the entire surgical device assemblies to the appropriate location on the path for the entry guide being used in system 200C. In another aspect, each of the entire surgical device assemblies is manually moved to the appropriate location on the path for the entry guide being used in system 200C.

Figure 2E:
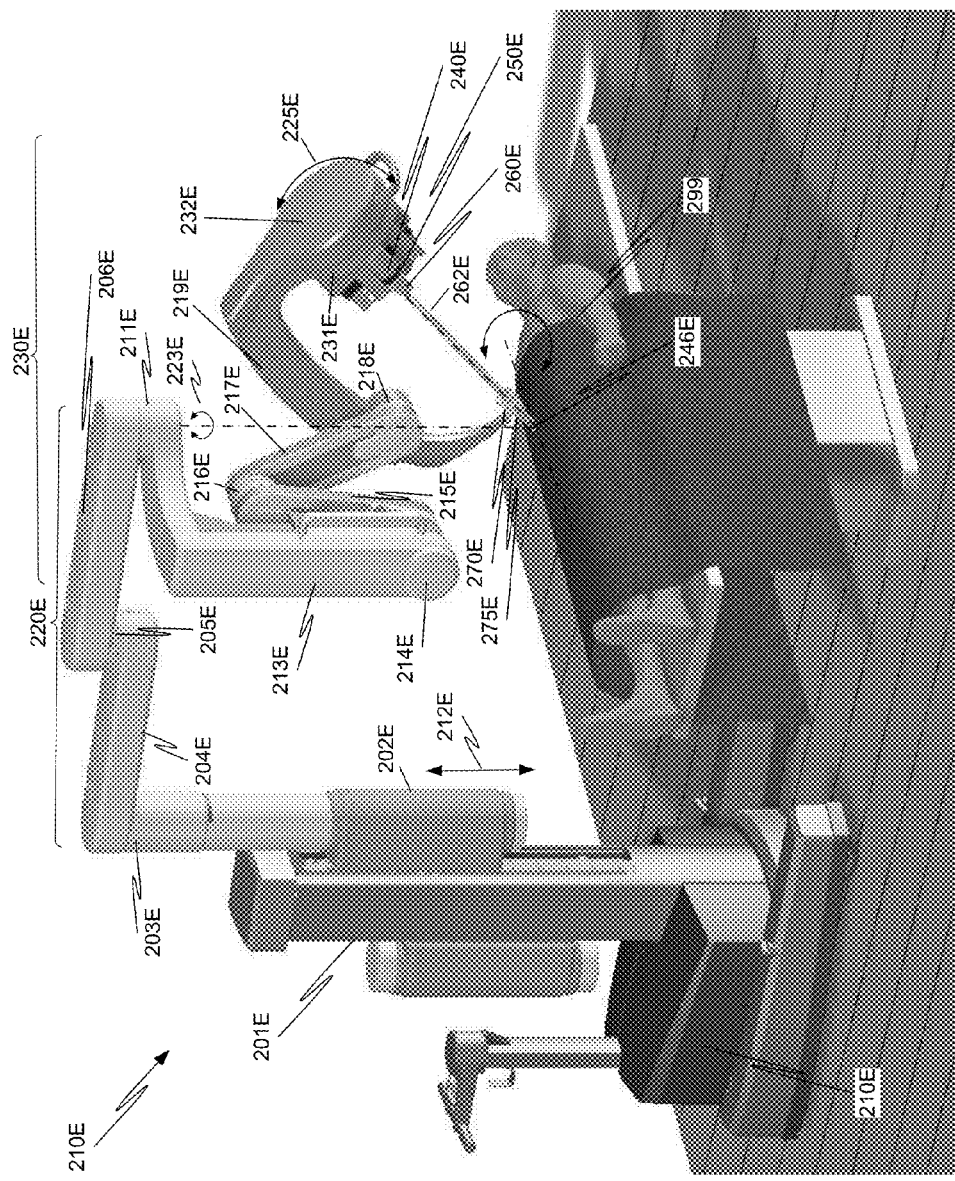
FIG. 2E is an illustration of a surgical system that includes an entry guide manipulator configured to position instruments so that when the shafts of the instruments enter an entry guide, any bending of the shafts does not damage the instruments.

FIG. 2E is an illustration of one implementation 210E of patient side support system 210C. In this aspect, patient side support system 210E is implemented as a patient-side cart 210E having a passive setup arm 220E and entry guide manipulator 230E. Entry guide manipulator 230E supports a plurality of surgical device assemblies.

In one aspect, at least one of the plurality of surgical device assemblies includes an instrument manipulator assembly 240E, a sterile adapter assembly 250E, and an instrument 260E. A main tube, sometimes referred to as a shaft, of instrument 260E extends through a channel in entry guide 270E during a surgical procedure.

The use of instrument manipulator assembly 240E and sterile adapter assembly 250E to couple instrument 260E to entry guide manipulator 230E is illustrative only and is not intended to be limiting. Instrument 260E can be coupled to entry guide manipulator in other ways so that instrument manipulator positioning system 231E can align shaft 262E with the corresponding channel in entry guide 270E for entry of shaft 262E into that channel.

Entry guide 270E is movably mounted in cannula 275E. Entry guide 270E may maintain an insufflation seal, if necessary, and entry guide 270E supports the shafts of the instruments at the entry into the body of patient 299. As explained more completely below, a plurality of different entry guides can be mounted and used in patient side support system 210E. Typically, a different entry guide is used for each different type of surgery.

The different surgeries that can be performed using patient side support system 210E may be performed on different regions of the body. For example, one surgery may be performed through the mouth of patient 299. Another surgery may be performed between the ribs of patient 299. Other surgeries may be performed through other orifices of patient 299. Entry guide 270E, which is suitable for abdominal surgery, may not be suitable for surgery through the mouth or between the ribs. A different shaped entry guide may be required for surgery through the mouth or between the ribs.

Not only is patient side support system 210E configured to use a variety of instruments, but also system 210E is configured to use a variety of different entry guides. Various combinations of these different entry guides are provided in kits.

When a rib entry guide for a surgery between the ribs is substituted for entry guide 270E, the channel configuration of the rib entry guide is different from the channel configuration of entry guide 270E, e.g., the layout of the channels relative to each other is different in the two entry guides. Also, one or more different surgical device assemblies may be mounted on entry guide manipulator 230E after the surgery using entry guide 270E is completed and the rib entry guide is mounted in patient side system 210E. Thus, the positions of the shafts of the surgical device assemblies are unlikely to be properly aligned for insertion into the rib entry guide. To correct this problem, entry guide manipulator 230E includes an instrument manipulator positioning system 231E. Instrument manipulator positioning system 231E simultaneously positions instrument mount interfaces for the surgical device assemblies with respect to the channels in the rib entry guide so that when a surgical device assembly is mounted on each of the instrument mount interfaces each instrument shaft is not damaged as the shaft passes through the corresponding channel in rib entry guide. This is done with little or no user input in some aspects.

Returning to the configuration illustrated in FIG. 2E, the plurality of surgical device assemblies mounted on entry guide manipulator 230E is spaced closely together. To permit this close packing arrangement and to permit the channels in entry guide 270E to be close together, in one aspect, the shafts of the instruments are angled from the instrument housings (See FIG. 4B) and in some aspects bent against entry guide 270E as the shafts pass through cannula 275E. As just described, instrument manipulator positioning system 231E simultaneously positions each of the entire surgical device assemblies, as needed, with respect to a corresponding channel in entry guide 270E so that each instrument shaft is not damaged as the shaft passes through the corresponding channel in entry guide 270E. Again, this is done with little or no user input, in one aspect.

In one aspect, instrument manipulator positioning system 231E limits the number of actuators and sensors required. Instrument manipulator positioning system 231E is synchronized with a roll system in entry guide manipulator 230E. The roll system rolls the surgical device assemblies as a group. In one aspect, gearing is used in instrument manipulator positioning system 231E to align the shafts of the surgical device assemblies for insertion into entry guide 270E and to maintain the synchronization.

To further simplify the design and the size of instrument manipulator positioning system 231E, in one aspect, the motion of instrument manipulator positioning system 231E used to align each of the plurality of instrument shafts with respect to the corresponding channels in entry guide 270E is limited to one degree of freedom in one aspect, and is limited to two degrees of freedom in another aspect. Irrespective of the number of degrees of freedom, the motion is in a plane. In addition, the range of motion of each of the plurality of surgical device assemblies is limited to the extent possible so that the range of motion of the plurality of surgical device assemblies does not compete for space that might otherwise be used for drape management, electronics, and reducing the overall size of system 210E.

Hence, as explained more completely below, entry guide manipulator 230E positions each entire surgical device assembly so that the shaft of the surgical device assembly is aligned for entry in the corresponding channel of entry guide 270E for that particular surgical device assembly. If the shaft is bent upon passing through entry guide 270E, the shaft is aligned so that any bending does not damage the instrument and does not inhibit operation of the instrument. This simultaneous automatic alignment of the instrument shafts is done for each entry guide that is used in system 210E.

In one aspect, a control system automatically checks on the compatibility of the surgical device assemblies mounted on entry guide manipulator 230E with the channel locations in entry guide 270E. In some instances, it is necessary to flex, e.g., slightly bend, the shaft of the instrument to insert the shaft in the appropriate channel in entry guide 270E. If this flex will damage the instrument, an alarm is issued by the control system when the instrument is mounted in system 210E and the system rejects use of that instrument. When a shaft of an instrument is flexed so that the resulting stresses are outside an allowable stress profile, the shaft may be damaged, e.g., permanently bent, and consequently the tendons that run through the shaft may not operate properly.

If the instrument is compatible with the entry guide, the control system checks other elements of the surgical system for compatibility with the entry guide, e.g., drapes, cameras, foot pedal control assemblies, master control assemblies, etc. Finally, the control system makes any needed adjustments in the user interface elements, allowable control modes, type and behavior of control modes, etc. for both the surgeon and patient side assistant based on the entry guide configuration. For example, if the entry guide is used in ear, throat, and nose surgery, the configuration and allowable range of motion of the various instruments would be different from entry guide 270E that is used for abdominal surgery, and so the control system automatically makes the necessary changes based on the entry guide to be used in the procedure.

As explained more completely below, in one aspect, each instrument 260E is positioned by entry guide manipulator 230E to maintain the bending stress or stresses on the instrument shaft within a predetermined stress profile. This assures that the bending does not damage the instrument and that the bending does not affect the correct operation of the instrument. For each entry guide with a different channel configuration, entry guide manipulator 230E positions each instrument so that the bending stress or stresses on the instrument shaft remains within the predetermined stress profile.

In FIG. 2E, elements 202E, 203E, 204E, 205E, 206E, and 211E of passive setup arm 220E are equivalent to elements 202C, 203C, 204C, 205C, 206C, and 211C of passive setup arm 220C. Thus, the description of passive setup arm 220C is applicable to passive setup arm 220E, and so is not repeated here. Elements 213E, 214E, 215E, 216E, 217E, 218E and 219E of entry guide manipulator 230E are equivalent to elements 213C, 214C, 215C, 216C, 217C, 218C and 219C of entry guide manipulator 230C. Thus, the description of elements 213C, 214C, 215C, 216C, 217C, 218C and 219C of entry guide manipulator 230C is applicable to elements 213E, 214E, 215E, 216E, 217E, 218E and 219E of entry guide manipulator 230E, and so is not repeated here. Similarly, base 201E is equivalent to base 201C.

Entry guide manipulator 230E changes the pitch around axis 221E of the plurality of surgical device assemblies as a group. Entry guide manipulator 230E changes the yaw around axis 223E of the plurality of surgical device assemblies as a group. In one aspect, entry guide manipulator 230E also rolls the plurality of surgical device assemblies as a group about a roll axis 225E. Roll axis 225E, in this aspect, is coincident with a longitudinal axis of cannula 275E. Pitch axis 221E, yaw axis 223E, and roll axis 225E intersect at remote center of motion 246E. Remote center of motion 246E is located along cannula 275E.

While it not shown in FIG. 2E, the surgical system also includes a control system and a master control console equivalent to those described with respect to FIG. 2C. In FIG. 2E, the surgery is in the abdomen of patient 299. However, the surgical system including patient side support system 210E is used for a wide variety of surgeries. The variety of surgical procedures uses various combinations of instruments.

For convenience, the instruments, in one aspect, are grouped into sets of instruments based on the shaft characteristics of the instruments, e.g., standard surgical instrument, advanced surgical instruments, and camera instruments, as explained more completely below. Briefly, the shafts of the advanced surgical instruments have a larger diameter than the diameter of the standard surgical instruments. The grouping of the instruments is for ease of discussion and the names of the groups are not intended to limit the instruments to any specific surgical instruments. In some surgeries, a manual instrument or instruments may be used in conjunction with teleoperated surgical instruments. A manual instrument is an instrument that a person controls using a handle or grip of the instrument itself.

The shaft of a camera instrument has a fixed bend. In one aspect, two different camera instruments are provided. One of the camera instruments has the fixed bend at a first location in a shaft of the camera instrument and the other of the camera instruments has the fixed bend in at a second location in a shaft of that camera instrument. The first and second locations are different locations.

Figures 3A, 3B:
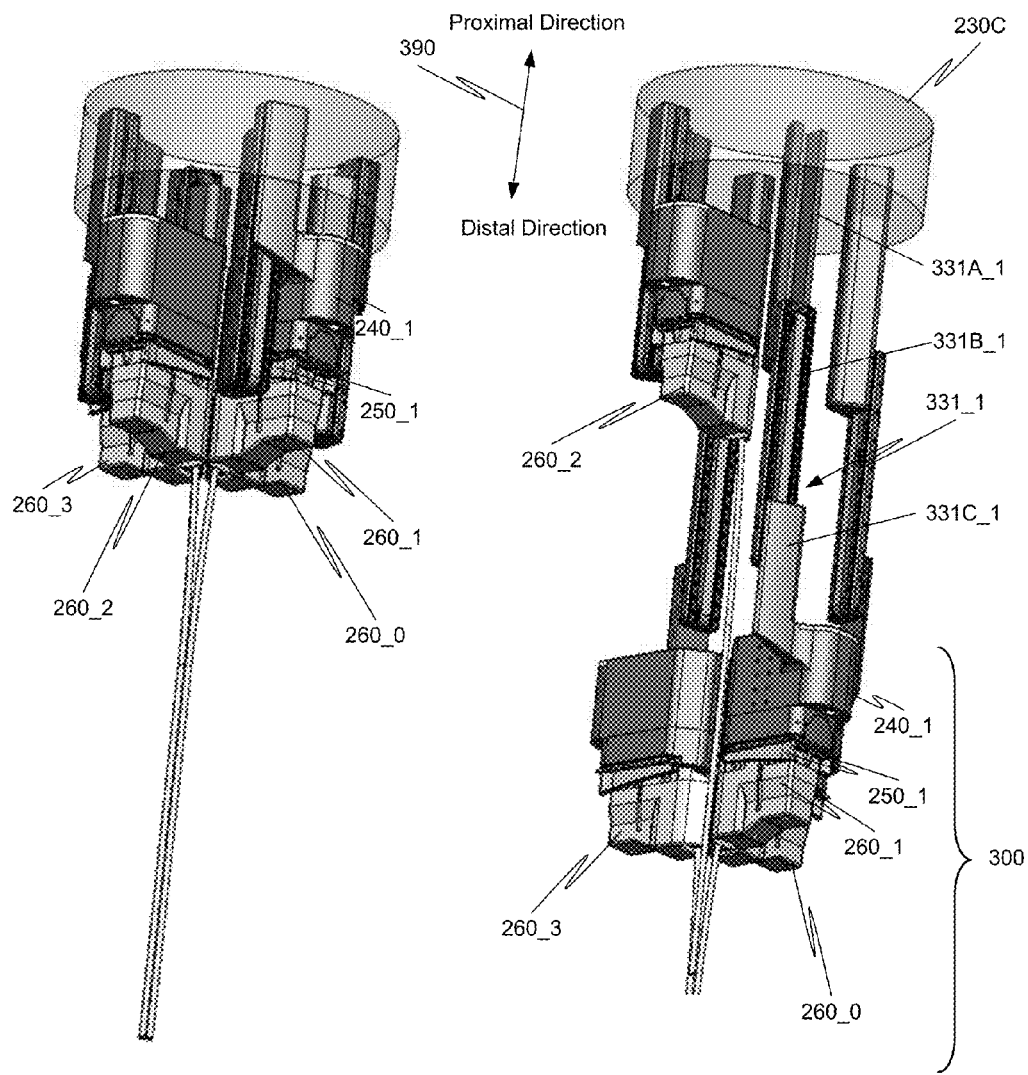
FIGS. 3A and 3B are more detailed illustrations of the configuration of the surgical device assemblies in FIG. 2E.

FIGS. 3A and 3B are illustrations of a plurality of surgical device assemblies 300 mounted on entry guide manipulator 230E. As noted above, each of the plurality of surgical device assemblies 300 includes an instrument manipulator assembly 240_1, a sterile adapter assembly 250_1, and an instrument 260_1. In FIG. 3A, each of the plurality of surgical device assemblies 300 is positioned at an initial position on an insertion assembly 331. Insertion assembly 331 is an example of a longitudinal motion mechanism. In FIG. 3B, three of the four surgical device assemblies have been moved distally on the insertion assembly. Arrow 390 defines the distal and proximal directions. Here, the distal direction is towards patient 299. The proximal direction is away from patient 299.

The proximal end of each insertion assembly in FIGS. 3A and 3B is shown as floating. As explained more completely below, in one aspect, the proximal end of each insertion assembly is mounted on a movable platform. The movable platform is coupled to instrument manipulator positioning system 231E in entry guide manipulator 230E. The movable platform allows the lateral motion mechanism of entry guide manipulator 230E to move the movable platform in a plane perpendicular to the longitudinal axis of entry guide 270, and consequently the entire surgical device assembly, so that the shaft of the instrument attached to the movable platform can be inserted in the corresponding channel of entry guide 270 without damaging the shaft, e.g., without exceeding the limits on the bending stresses. Once the instrument is properly positioned by instrument manipulator positioning system 231E, the movable platform is locked in place.

FIGS. 3A and 3B illustrate the configuration that is used as an example in the following description. Instrument 260_0 is a camera instrument. Instruments 260_1 to 260_3 are standard or advanced surgical instruments. Instrument 260_1 is referred to as a first surgical instrument, instrument 260_2 as a second surgical instrument, and instrument 260_3 as a third surgical instrument. Thus, the camera instrument is mounted roughly at the twelve o'clock position on a clock; the first surgical instrument is mounted roughly at the three o'clock position, and so on. The first, second, and third surgical instruments may be instruments of the same type, or instruments of different types. The types of the surgical instruments are selected for compatibility with the channel sizes in the entry guide, as explained more completely below.

As illustrated in FIG. 3B, each insertion assembly includes three components. Using insertion assembly 331_1 as an example, insertion assembly 331_1 includes a frame 331A_1, a mid-carriage 331B_1, and a distal carriage 331C_1. Mid-carriage 331B_1 rides on a ball screw in frame 331A_1. In one aspect, the ball screw has a 6 mm pitch, and so the ball screw is back-drivable. Mid-carriage 331B_1 includes metal belts that drive distal carriage 331C_1. Distal carriage 331C_1 is attached to surgical device assembly 300 that includes surgical instrument 260_1.

Thus, as described more completely below, when a positioning element in instrument manipulator positioning system 231E moves the movable platform affixed to the proximal end of frame 331A_1, insertion assembly 331_1 and the surgical device assembly of plurality of surgical device assemblies 300 including surgical instrument 260_1 and its shaft are all moved as a single unit. Thus, the movement of the positioning element in instrument manipulator positioning system 231E moves insertion assembly 331_1 and entire surgical device assembly 300 including surgical instrument 260_1 and its shaft along the same trajectory that the positioning element follows.

Figures 4A, 4B:
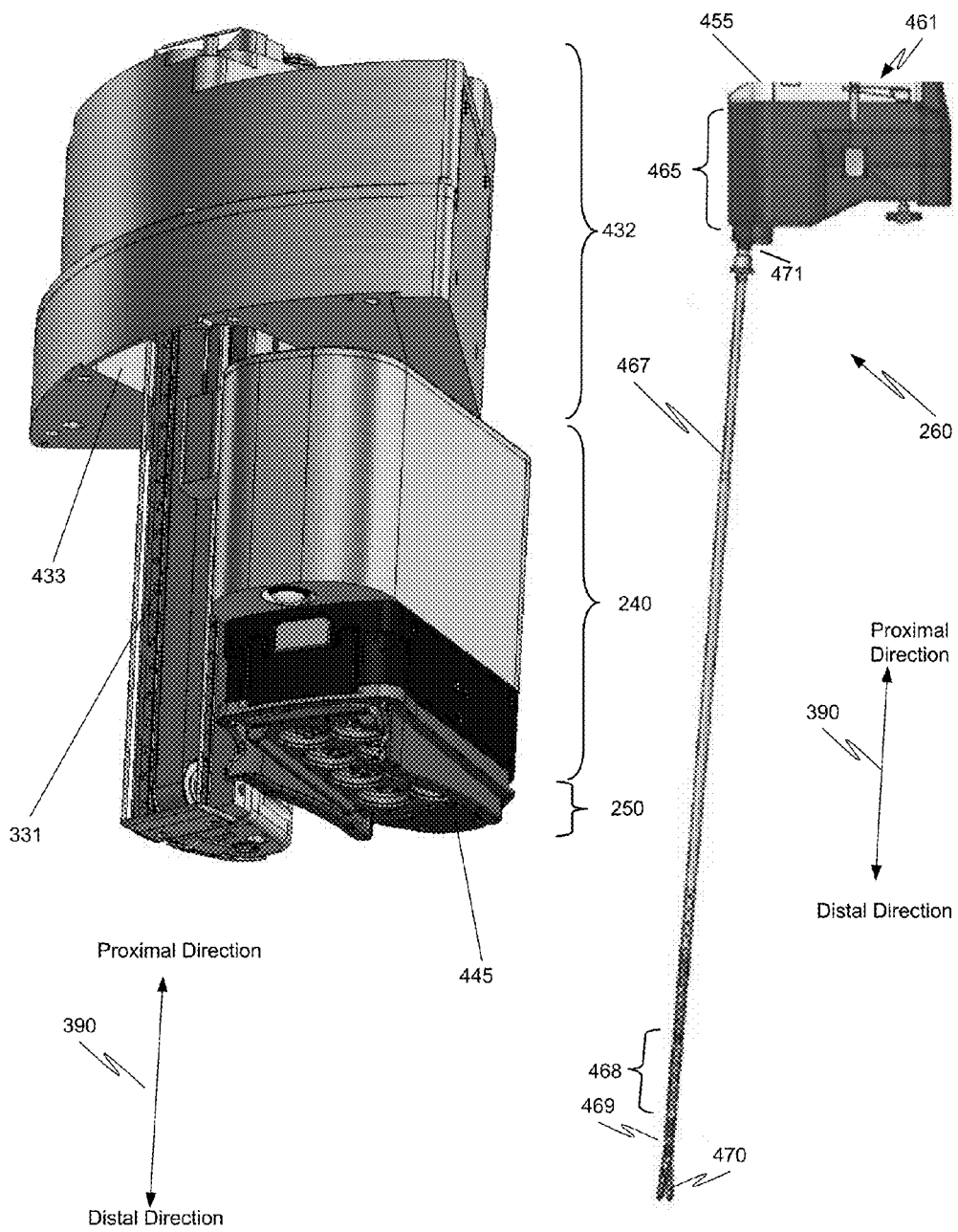
FIG. 4A illustrates a manipulator assembly affixed to an insertion assembly that in turn is attached to a base assembly.
FIG. 4B is a more detailed illustration of the instruments of FIGS. 2A, 2C, 2E, 3A and 3B.

Prior to considering the positioning of the instrument in plurality of surgical device assemblies 300 in further detail, one aspect of a surgical device assembly is described. FIGS. 4A and 4B are a more detailed illustration of one aspect of a surgical device assembly in plurality of surgical device assemblies 300.

A base assembly 432 (FIG. 4A) is connected to a rotatable base in entry guide manipulator 230E. Insertion assembly 331 is connected to a floating platform (not visible) in base assembly 432. There is an opening 433 in the distal end of base assembly 432 in which insertion assembly 331 can move about, as described more completely below.

In this example, the housing of base assembly 432 is roughly wedge shaped (pie-shaped) to allow assembly 432 to be closely positioned to similar housings as illustrated in FIG. 2E. A vertex of the wedge shape of each of the base assemblies of the four surgical device assemblies is arranged around an extended longitudinal axis of cannula 275E.

An instrument manipulator assembly 240 is affixed to insertion assembly 331. Instrument manipulator assembly 240 is an example of the instrument manipulator assemblies illustrated in FIGS. 2A to 2C, 2E, 3A, and 3B. Instrument manipulator assembly 240 includes a plurality of drive units.

A sterile adapter assembly 250 is mounted on instrument manipulator assembly 240. Sterile adapter assembly 250 is an example of the sterile adapter assemblies illustrated in FIGS. 2E, 3A, and 3B. Sterile adapter assembly 250 includes a plurality of intermediate disks. Each intermediate disk is coupled to a drive disk on a drive unit of instrument manipulator assembly 240. Hence, in this example, the instrument mount interface is provided by a combination of instrument manipulator assembly 240 and sterile adapter assembly 250. However, the instrument mount interface could alternatively be defined as a distal face of sterile adapter assembly 250 mounted on instrument manipulator assembly 240.

Sterile adapter assembly 250 includes a sterile drape (not shown). Sterile drapes are known and so are not described in further detail. See for example, U.S. Pat. No. 7,666,191 B2, U.S. Pat. No. 7,699,855 B2, U.S. Patent Application Publication No. US 2011/0277775 A1, and U.S. Patent Application Publication No. US 2011/0277776 A1, all of which are incorporated herein by reference. The sterile drape drapes at least a portion of system 210E to maintain a sterile field during a surgical procedure while sterile adapter assembly 250E also facilitates efficient and simple instrument exchange.

FIG. 4B is a more detailed illustration of an example of a surgical instrument 260. Surgical instrument 260 is an example of the surgical instruments illustrated in FIGS. 2A, 2C, 2E, 3A, and 3B. Surgical instrument 260, in this aspect, includes a driven interface assembly 461, a transmission unit 465, a main tube 467, a parallel motion mechanism 468, a wrist 469, and an end effector 470. Wrist 469 is described, for example, in U.S. Patent Application No. US 2003/0036478 A1 (disclosing "Surgical Tool Having Positively Positionable Tendon-Activated Multi-Disk Wrist Joint"), which is incorporated herein by reference. Parallel motion mechanism 868 is described, for example, in U.S. Pat. No. 7,942,868 B2 (disclosing "Surgical Instrument With Parallel Motion Mechanism"), which also is incorporated herein by reference.

Driven interface assembly 461 includes a plurality of driven disks. Each driven disk is coupled to a corresponding intermediate disk in sterile adapter assembly 250 when surgical instrument 260 is mounted in sterile adapter 250, as illustrated in FIGS. 2D, 3A, and 3B.

Mechanical components (e.g., gears, levers, gimbals, cables etc.) in transmission unit 465 transfer forces from the driven disks to cables, wires, and/or cable, wire, and hypotube combinations that run through main tube 467 to control movement of parallel motion mechanism 468, wrist 469, and end effector 470. Main tube 467 has a bearing 471 at the proximal end of main tube 467.

Main tube 467 is substantially rigid, which means that main tube 467 can be bent slightly between transmission unit 465 and entry guide 270E. This bending allows the channels in entry guide 270E to be spaced closer together than the size of the base assemblies would otherwise allow. The bending is resilient so that main tube 467 assumes its straight shape when surgical instrument 260E is withdrawn from entry guide 270E (the main tube may be formed with a permanent bend as in the camera instrument). The allowable stress profile, mentioned above, is a stress profile such that the bending remains resilient and main tube 467 is not permanently deformed by the bending stresses.

Instrument manipulator assembly 240 (FIG. 4A) includes a radio-frequency identification (RFID) reader 445 in a distal end of instrument manipulator assembly 240. Surgical instrument 260 has an RFID tag 455 mounted on a proximal end surface of instrument 260. When surgical instrument 260 is mounted in sterile adapter assembly 250, RFID tag 455 is positioned under RFID reader 445. After surgical instrument 260 is mounted in sterile adapter assembly 250, the control system receives the information from RFID reader 445 and uses the information in identifying surgical instrument 260 to determine the compatibility of surgical instrument 260 with entry guide 270E.

FIG. 5A is a schematic representation of four base assemblies 432_0, 432_1, 432_2, and 432_3 mounted on entry guide manipulator 230E. FIG. 5A shows that four wedge-shaped assemblies 432_0, 432_1, 432_2, and 432_3 form a circle 501. Center 501C of circle 501 is on the extended longitudinal axis of cannula 275E.

The use of wedge-shaped base assemblies is illustrative only and is not intended to be limiting. The base assemblies could have a square shape, a rectangular shape, or other shape so long as the base assemblies can be mounted on entry guide manipulator 230E and then moved as a group in roll, pitch, and yaw by entry guide manipulator 230E. For example, in FIG. 5F, base assemblies having a hexagonal shape as shown in a configuration 595 that could be mounted on and moved by entry guide manipulator 230E.

FIG. 5B is a cross sectional view of a first entry guide 570S that is referred to as a standard entry guide 570S. Entry guide 570S is movably, e.g., rotatably, mounted in a cannula 580. Entry guide 570S has four lumens that are referred to as channels. The channels extend from a proximal end of entry guide 570S to a distal end of entry guide 570S, e.g., the channels extend from a first end to a second end of the entry guide. This is true for each of the channels of an entry guide described herein. In one aspect, entry guide 570S is entry guide 270E and cannula 580 is cannula 275E.

In this aspect, one of the surgical device assemblies includes an endoscope and a camera. This instrument is referred to as a camera instrument. The camera instrument has a pre-bent shaft. The bend in the shaft remains between the distal part of transmission unit 465 and the proximal end of entry guide 270E, e.g., the bend does not enter entry guide 270E. The cross-section of the portion of the camera shaft that goes through entry guide 270E and cannula 275E is an oblong shape, in one aspect. Alternatively, the cross-section of the portion of the camera shaft that goes through entry guide 270E and cannula 275E could have a circular shape.

Thus, standard entry guide has a camera channel 571S with an oblong cross section, and three surgical instrument channels 572S1, 572S2, 572S3 that are circular in cross section. In this aspect, each of the three surgical instrument channels 572S1, 572S2, 572S3 is the same size, e.g., has the same diameter. The diameter is selected such that a sheathed shaft of a surgical instrument can be passed through the channel. Surgical instrument channels 572S1, 572S2, 572S3 are referred to as standard surgical instrument channels.

In FIG. 5A, a channel in standard entry guide 570S that is associated with a particular base assembly 432_0, 432_1, 432_2, and 432_3 is shown as a dotted line. A channel being associated with a base assembly means that the shaft of the surgical instrument mounted on that base assembly is inserted through the channel. For example, surgical instrument 260_2 is mounted on base assembly 432_2 and shaft 467 passes through channel 572S2. Thus, both base assembly 432_2 and surgical instrument 260_2 are associated with channel 572S2.

FIG. 5C is a cross sectional view of a second entry guide 570MS. Entry guide 570MS is positioned in a cannula 581. Entry guide 570MS also has four lumens that are referred to as channels. Entry guide 570MS has an outer diameter that is larger than the outer diameter of standard entry guide 570S.

Entry guide 570MS has an oblong camera channel 571MS, and two standard circular surgical instrument channels 572MS1 and 572MS3. In this aspect, entry guide 570MS also includes a manual instrument channel 573MS. In one aspect, a manually controlled surgical instrument is passed through channel 573MS. In another aspect, a tele-operated surgical instrument is passed through channel 573MS.

In FIG. 5D, an x-axis 590 and a y-axis 591 have an origin at a center of entry guide 570MS. Entry guide 570S, which is represented by dashed lines, is overlaid on entry guide 570MS with its center also at the origin. The center of entry guide 570MS in FIG. 5D represents a longitudinal axis of entry guide 570MS.

Assuming that entry guide 570MS is being used and the positioning elements for the surgical instruments attached to base assemblies 432_1 and 432_3 are in the standard positions as shown in FIG. 5A, the shafts of surgical instruments 260_1 and 260_3 (FIG. 3A) are not properly positioned for insertion through channels 572MS1 and 572MS3. Instead, the shafts of surgical instruments 260_1 and 260_3 are positioned to pass though channels 572S1 and 572S3 in standard entry guide 570S. Similarly, camera instrument 260_0 is positioned for channel 571S and not channel 571MS.

In one aspect, instrument manipulator positioning system 231E in entry guide manipulator 230E moves a first positioning element that is associated with surgical instrument 260_1 to a position indicated by arrow 586. Specifically, the movement of the positioning element is coupled to surgical instrument 260_1, and so moves the shaft of surgical instrument 260_1 to the appropriate position to enable insertion of the shaft into channel 572MS1 without damaging the shaft.

Similarly, instrument manipulator positioning system 231E in entry guide manipulator 230E moves a second positioning element that is associated with surgical instrument 260_3 to a position indicated by arrow 583. The instrument manipulator positioning system in entry guide manipulator 230E also moves a third positioning element that is associated with camera instrument 260_0 to a position indicated by arrow 585. In the new positions, the shafts of the surgical instruments and the shaft of the camera instrument are positioned to enable insertion through the corresponding channels in entry guide 570MS. In one aspect, all of the positioning elements are simultaneously moved to the correct location. In one aspect, the positioning elements are included in the lateral motion mechanism of system 231E.

In FIG. 5E, the dotted lines represent a position of insertion assembly 531 and a surgical device assembly 500 with a shaft 567 configured for a first entry guide, e.g., entry guide 570S. If shaft 567 is withdrawn from entry guide 570S and a second entry guide such as entry guide 570MS is placed in the system, the position of shaft 567 as shown by the dotted line is not correct for entry into the corresponding channel in the second entry guide (See FIG. 5D).

The solids lines in FIG. 5E illustrate the result of instrument manipulator positioning system 550 in entry guide manipulator 530 moving positioning element 549 that is coupled to surgical device assembly 500. In particular, insertion assembly 531 is mounted on a floating platform 532A that is connected to positioning element 549. As positioning element 549 is moved by instrument manipulator positioning system 550, floating platform 532A is moved, which in turn moves entire surgical device assembly 500 including shaft 567.

Thus, to reposition surgical device assembly 500 for entry guide 570MS, instrument manipulator positioning system 550 moves positioning element 549 that in turn moves floating platform 532A so that insertion assembly 531 and entire surgical device assembly 500 including shaft 567 are moved from the position represented by the dotted lines to the position shown in FIG. 5E by the solid lines. In one aspect, positioning element 549 is moved by manually turning a knob. In another aspect, positioning element 549 is moved using a servomotor.

Only one surgical device assembly 500 and its associated base assembly 532 are shown in FIG. 5E. However, this is representative of each of the four base assemblies in one aspect, and so the description is applicable to each of the total number of base assemblies, e.g., four base assemblies, or in some aspects is applicable to a number of base assemblies smaller than the total number of base assemblies. Also, the use of an insertion assembly to couple the surgical device assembly to the associated base assembly is illustrative only, and is not intended to be limiting. In another aspect, the surgical device assembly is coupled directly to the base assembly.

FIG. 5E also illustrates circular bending of shaft 567. In circular bending, the bend in shaft 567 is an arc of a circle. When shaft 567 is circularly bent, the circular bend introduces the minimum stress over the length of the bend of all of the possible bends, as discussed more completely below.

FIG. 6A is an illustration of one implementation of an instrument manipulator positioning system 640A in entry guide manipulator 530. Only one surgical device assembly 500 and its associated base assembly 532 are shown in FIG. 6A. However, this is representative of each of the total number of base assemblies in one aspect, and so the description is applicable to each of four base assemblies, or in some aspects is applicable to a number of base assemblies smaller than the total number of base assemblies.

Floating platform 600A, e.g., a moveable platform, in base assembly 532 is connected to insertion assembly 531. Thus, as indicated above, movement of floating platform 600A moves the location of shaft 567. A positioning element 610 in lateral motion mechanism of instrument manipulator positioning system 640A is coupled to floating platform 600A. In this example, positioning element 610 and floating platform 600A can be moved in four degrees of freedom, e.g., along a first axis 601, along a second axis 602, in pitch 603, and in yaw 604. First axis 601 and second axis 602 are in a plane that is perpendicular to a longitudinal axis of the entry guide, as previously shown.

In one aspect, platform 600A is suspended on a rail system so that positioning element 610 can move floating platform 600A and hence insertion assembly 531 in directions 601, 602. Platform 600A also is movably suspended on a support 620 that allows changing the pitch of positioning element 610 and platform 600A, e.g., the rail system is mounted on support 620. Support 620 can also rotate about anchor 630 to change the yaw of positioning element 610 and platform 600A.

As indicated above, patient side support system 210E is used with a wide variety of entry guides. The particular entry guide used typically depends on the surgery being performed. In some instances, a channel in an entry guide may not extend straight through the entry guide. In this case, the instrument shafts exiting the entry guide are not all parallel to the longitudinal axis of the entry guide, but rather the instrument shafts are splayed. The entry guide has one or more channels that are at an angle to the longitudinal axis of the entry guide, e.g., the channel is canted. For this entry guide, pitch and/or yaw of positioning element 610 can be changed to insert shaft 567 into the chanted channel.

FIG. 6B is a cross-sectional view of an entry guide 670 with at least one canted channel 670C, e.g., channel 670C is at an angle to longitudinal axis 690. Longitudinal axis 690 extends from distal end 670D of entry guide 670 to the proximal end 670P of entry guide 670. Lengthwise axis 670CL of channel 670C is angled relative to longitudinal axis 690. Entry guide 670 may have more than the two channels visible in FIG. 6B.

In one aspect, channel 670C is a manual channel. The angle of the manual channel is selected to facilitate aiming a manual instrument, e.g., a stapler, at the center of the surgical site.

FIG. 6C illustrates an example of an instrument manipulator positioning system 640C that moves insertion assembly 531 and consequently shaft 567 in two perpendicular directions 601, 602, i.e., in two degrees of freedom, in a plane perpendicular to a longitudinal axis of the entry guide. Insertion assembly 531 extends through an opening 653 in a second floating platform 600C. The proximal end of insertion assembly 531 is mounted to a first floating platform 600B. Platform 600B rides on a first set of rails 663. Set of rails 663 is mounted on platform 600C. A servomotor 660 is connected to platform 600B by a first positioning element, in this aspect, by a lead screw 661 and a nut.

Platform 610C rides on a second set of rails 652. A servomotor 650 is connected to platform 600B by a second positioning element, in this aspect, by a lead screw 651 and a nut. Servomotor 650 moves platform 600C and consequently insertion assembly 531 in direction 601. Servomotor 660 moves platform 600B and consequently insertion assembly 531 in direction 602. To add the ability to change the pitch and yaw, set of rails 652 is mounted on support that has the two degrees of freedom. The configuration of positioning mechanism 640C is illustrative only and is not intended to be limiting to the specific elements illustrated.

FIGS. 7A to 7C are a top, bottom, and oblique views respectively of one aspect of a portion of a base assembly 732 that includes a floating platform 700. Base assembly 732 is representative of one aspect of base assembly 432. In FIGS. 7A to 7C, only components necessary to understand this aspect of floating platform 700 are included.

Floating platform 700 includes a first platform 700A and a second platform 700B. First platform 700A has legs 700L1, 700L2 (FIG. 7B). Leg 700L1 has an outer side surface 700L1S that lies in a plane that is perpendicular to a plane including an inner side surface 700L2S of leg 700L2. Axis 790 is along outer side surface 700L1S, while axis 791 is along inner side surface 700L2S.

Outer side surface 700L1S of leg 700L1 is coupled to a first set of precision linear rails 752. Set of rails 752 is affixed to an inner side surface of base assembly 732. In FIGS. 7B and 7C, only the distal rail in set 752 is visible. A proximal rail also is affixed to base assembly 732. Sets of bearings 701 are mounted on outer side surface 700L1S of leg 700L1. Sets of bearings 701 are preloaded and ride on set of rails 752.

A side surface of second platform 700B is coupled to inner side surface 700L2S of leg 700L2. A proximal portion 700B1 of second platform 700B extends over a proximal end surface of leg 700L2. Another side surface of second platform 700B is affixed to a portion of insertion assembly 731. In one aspect, insertion assembly 731 includes a frame, a mid-carriage, and a distal carriage. The portion of insertion assembly 731 illustrated in FIGS. 7A to 7C is the frame. The mid-carriage rides on a ball screw 713 in the frame. In one aspect, ball screw 713 has a 6 mm pitch, and so ball screw 713 is back-drivable. The mid-carriage includes metal belts that drive the distal carriage. The distal carriage is attached to the surgical device assembly.

A second set of precision linear rails 763 is affixed to inner side surface 700L2S of leg 700L2. Second set of rails 763 is perpendicular to first set of rails 752. In FIGS. 7B and 7C, only the distal rail in set 763 is visible. A proximal rail also is affixed to inner side surface 700L2S of leg 700L2. Sets of bearings 702 are mounted on a side surface of platform 700B. Sets of bearings 702 are preloaded and ride on set of rails 763.

Proximal portion 700B1 of second platform 700B includes a positioning element receptacle 710 that is positioned in a circular opening 715 in proximal end surface of base assembly housing 732. As explained more completely below, a unit that includes the positioning element is mounted on housing 732 so that the positioning element, e.g., a pin, mates with positioning element receptacle 710. In one aspect, both the pin and positioning element receptacle 710 are made of strong steel and are precisely machined to minimize backlash in the coupling of the pin in positioning element receptacle 710. In one aspect, second platform 700B is made of stainless steel, for example, Nitronic 60, thirty percent cold worked. However, any strong steel that operates well, e.g., does not exhibit galling or cold welding, with other steels can be used.

FIG. 7D is a cut-away illustration of one aspect of positioning element receptacle 710. A positioning element receptacle assembly 714 is mounted on proximal portion 700B 1 of second platform 700B. Positioning element receptacle assembly 714 includes a housing 714H, positioning element receptacle 710, and two bearings 711, 712. Positioning element receptacle 710 is a hollow cylinder, which is open at the proximal end and open at the distal end, in this aspect. Bearing 711 is positioned between housing 714H and positioning element receptacle 710 adjacent a proximal end of positioning element receptacle 710. Bearing 712 is positioned between housing 714H and positioning element receptacle 710 adjacent a distal end of positioning element receptacle 710. Bearings 711 and 712 allow positioning element receptacle 710 to rotate relative to housing 714H, and hence relative to second platform 700B. The use of bearings 711 and 712 is illustrative only and is not intended to be limiting. In one aspect, bearings are not included in positioning element receptacle assembly 714.

Platform 700 floats on sets of rails 752 and 763. When the positioning element is mated with positioning receptacle 710, movement of the positioning element moves floating platform 700 along one or both of axes 790, 791. Instrument manipulator positioning system 231E in entry guide manipulator 230E controls the location of insertion assembly 731 by moving the positioning element to a particular location.

Figure 8A:
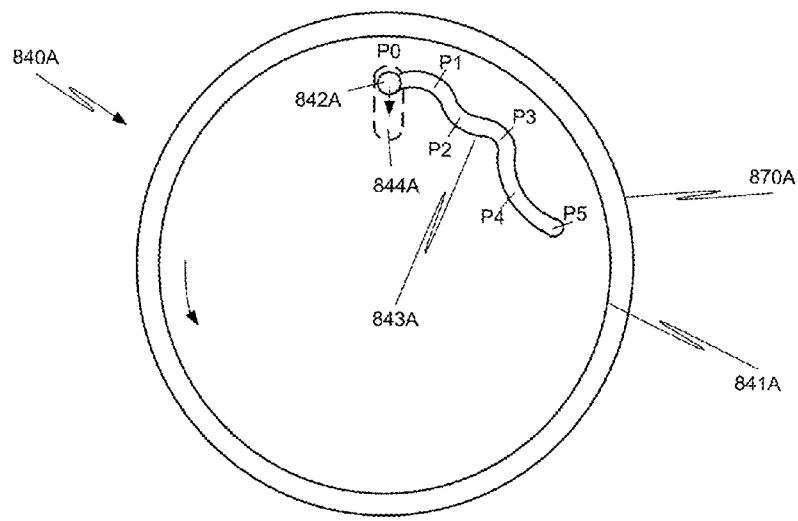
FIGS. 8A, 8B, and 8C are other examples of the instrument manipulator positioning system of FIGS. 2A and 2B that can be included in the entry guide manipulator of FIG. 2C and in the entry guide manipulator of FIG. 2E.

FIG. 8A is a first example of an instrument manipulator positioning system 840A that can be included in entry guide manipulator 230E and coupled to floating platform 700. Instrument manipulator positioning system 840A includes an adjustment disk 841A that is coupled to a fixed disk 870A. When adjustment disk 841A and fixed disk 870A move synchronously together, rotation of fixed disk 870A rolls plurality of surgical device assemblies 300 as a group, as previously described. Specifically, adjustment disk 841A moves in synchronization with fixed disk 870A so that rotation of fixed disk 870A rolls the surgical device assemblies coupled to adjustment disk 841A.

However, to position a shaft of an instrument for insertion into a particular entry guide, adjustment disk 841A is first decoupled from fixed disk 870A so that rotation of adjustment disk 841A is not transferred to fixed disk 870A. For a given set of entry guides, a location of the positioning element is known for the channel in each entry guide. In this example, for the given set of entry guides, the positioning element can moved to any one of five locations P0 to P5, which are known. The displacements needed to move the positioning element from one location to the next are programmed in instrument manipulator positioning system 840A. In this example, an adjustment cam 843A defines the location of positioning element for each of five locations P0 to P5.

A cam follower 842A is mounted to ride on adjustment cam 843A and in a fixed slot 844A. Fixed slot 844A limits the range of motion of cam follower 842A, and so limits the motion of the positioning element. In one aspect, two types of motions are possible using cam follower 842A—linear motion along a line and circular motion along an arc.

For motion along a line, cam follow 842A includes a rod such that one end of the rod rides in adjustment cam 843A and a second end of the rod extends, for example, into positioning element receptacle 710. Thus, as adjustment disk 841A rotates, the rod moves in fixed slot 844A, which in turn moves moving platform 700 and the distal end of an instrument coupled to insertion assembly 731 along a line in a plane.

Figure 8B:
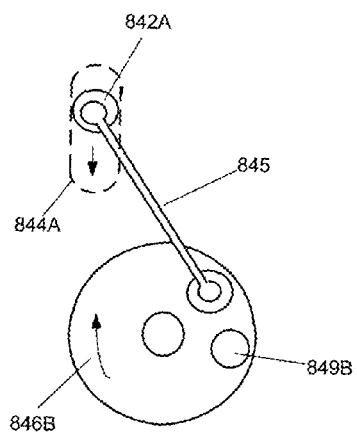

For motion along an arc, a link rod 845 (FIG. 8B) connects cam follower 842A to a rotary disk 846B. Positioning element 849B is affixed to a side surface of rotary disk 846B. As adjustment disk 841A is rotated, a pin in the cam follower 842A follows adjustment cam 843A and acts like a slider crank to drive rotary disk 846B. Output pin 894B, the positioning element, is mounted on a side surface of disk 846B. Thus, as rotary disk 846B rotates, output pin 849B moves along a constant radius arc. In one aspect, output pin 849B is mounted in positioning element receptacle 710, and so the shaft of the instrument coupled to floating platform 700 moves along a constant radius arc.

Figure 8C:
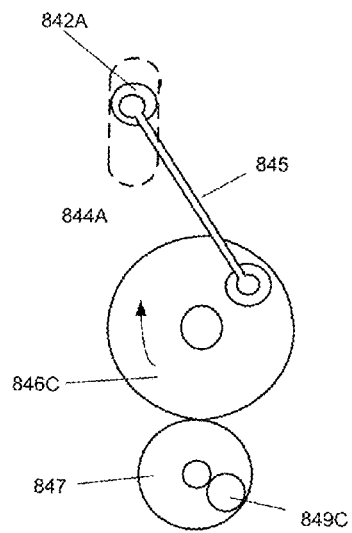

In one aspect (FIG. 8C), positioning element 849C is mounted on a side of secondary disk 847. Secondary disk 847 is geared from rotary disk 846C. Thus, output pin 849C follows an arc that is different from the arc followed by output pin 849B.

While in FIG. 8A only a single fixed slot, single cam follower and single adjustment cam are shown, adjustment disk 841A can include a fixed slot, a cam follower, and an adjustment cam for each of plurality of surgical device assemblies 300 or a fixed slot, a cam follower, and an adjustment cam for each of less than all of plurality of surgical device assemblies 300.

Figure 8D:
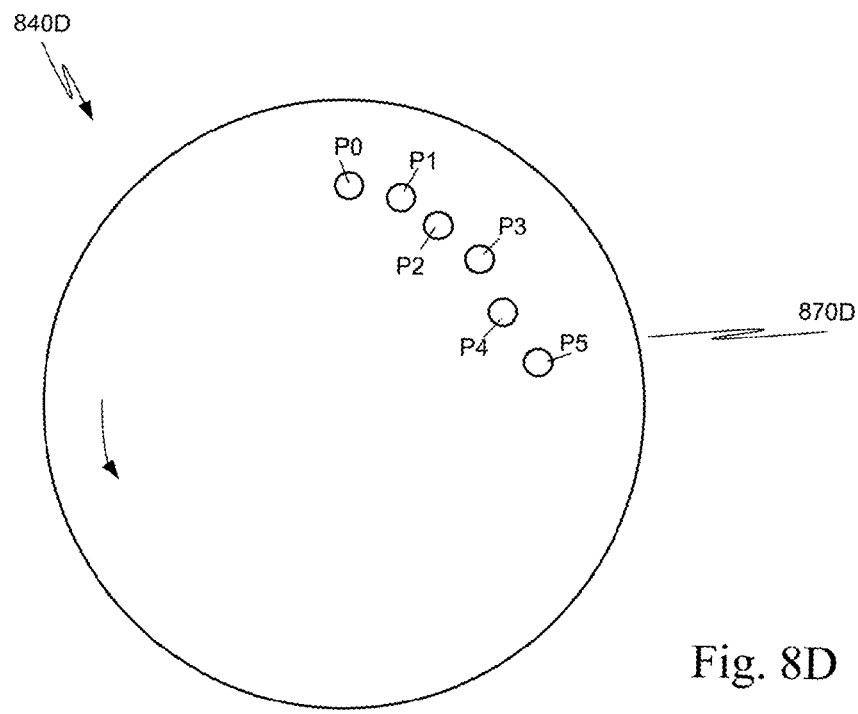
FIG. 8D is yet another example of the instrument manipulator positioning system of FIGS. 2A and 2B that can be included in the entry guide manipulator of FIG. 2C and in the entry guide manipulator of FIG. 2E.

FIG. 8D illustrates another example of an instrument manipulator positioning system 840D that can be included in entry guide manipulator 230E and coupled to floating platform 700. Instrument manipulator positioning system 840D includes a fixed disk 870D. Plurality of surgical device assemblies 300 is coupled to fixed disk 870D in entry guide manipulator 230E so that rotation of fixed disk 870D rolls plurality of surgical device assemblies 300, as a group. Note that in this aspect, an adjustment disk is not used, because the surgical device assemblies are moved manually to the correct location.

To position a shaft of an instrument for insertion into a particular entry guide, a user manually moves floating platform 700 until positioning element receptacle 710 aligns with one of five locations P0 to P5, which are through holes in fixed disk 870D. In one aspect, the outer surface of the entry guide adjacent a channel includes a number between 0 and 5 so that the operator knows which of the five locations P0 to P5 to select.

When positioning element receptacle 710 is aligned with the correct location in fixed disk 870D, a pin is inserted through positioning element receptacle 710 into the hole in fixed disk 870D to lock floating platform in place. In one aspect, a ball lock pin is used to lock floating platform 700 to fixed disk 870D. While in FIG. 8D only a single set of locations are illustrated, fixed disk 870D can include a set of locations for each of plurality of surgical device assemblies 300 or for each of less than all of plurality of surgical device assemblies 300.

Figure 8E:
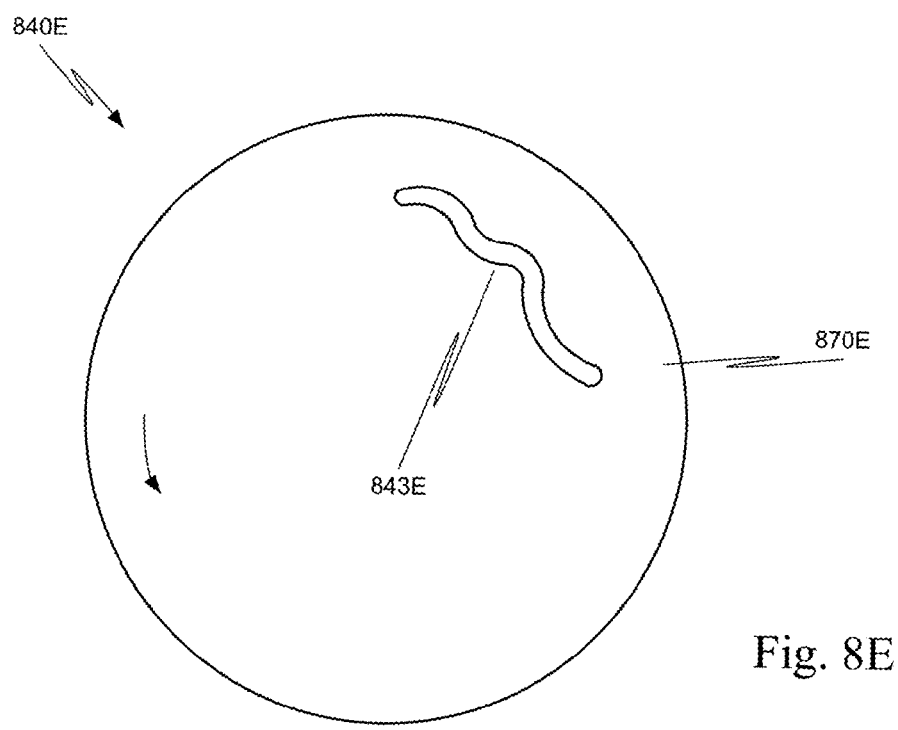
FIG. 8E is still another example of the instrument manipulator positioning system of FIGS. 2A and 2B that can be included in the entry guide manipulator of FIG. 2C and in the entry guide manipulator of FIG. 2E.

FIG. 8E illustrates another example of an instrument manipulator positioning system 840E that can be included in entry guide manipulator 230E and coupled to floating platform 700. Instrument manipulator positioning system 840E includes an adjustment path 843E in fixed disk 870E. Plurality of surgical device assemblies 300 is coupled to fixed disk 870E in entry guide manipulator 230E so that rotation of fixed disk 870E rolls plurality of surgical device assemblies 300, as a group.

For a given set of entry guides, acceptable locations of positioning element receptacle 710 are known for a channel in each entry guide. In this example, for the given set of entry guides, the acceptable locations are along adjustment path 843E in fixed disk 870E.

However, to move a shaft of an instrument for insertion into a particular entry guide, entry guide 270E is moved so that the longitudinal axis of entry guide 270E is vertical. Next, a surgical instrument having a shaft is mounted onto an instrument manipulator to form a surgical device assembly, and the shaft of the surgical device assembly is inserted into a channel of entry guide 270E. If the shaft is bent, the instrument manipulator would move along adjustment path 843E to a position of least energy, e.g., the instrument manipulator would move to where the shaft is bent the least, and so the bend in the shaft is minimized. After the surgical device assembly has moved to the position of least energy, floating platform 700 is locked to adjustment path 843E at that location. In one aspect, a ball lock pin is used to lock floating platform 700 to a location of adjustment path 843E of fixed disk 870E. While in FIG. 8E only a single adjustment path 843E is illustrated, fixed disk 870E can include a set of adjustment paths, one path each of plurality of surgical device assemblies 300 or one path for each of less than all of plurality of surgical device assemblies 300.

Figure 9:
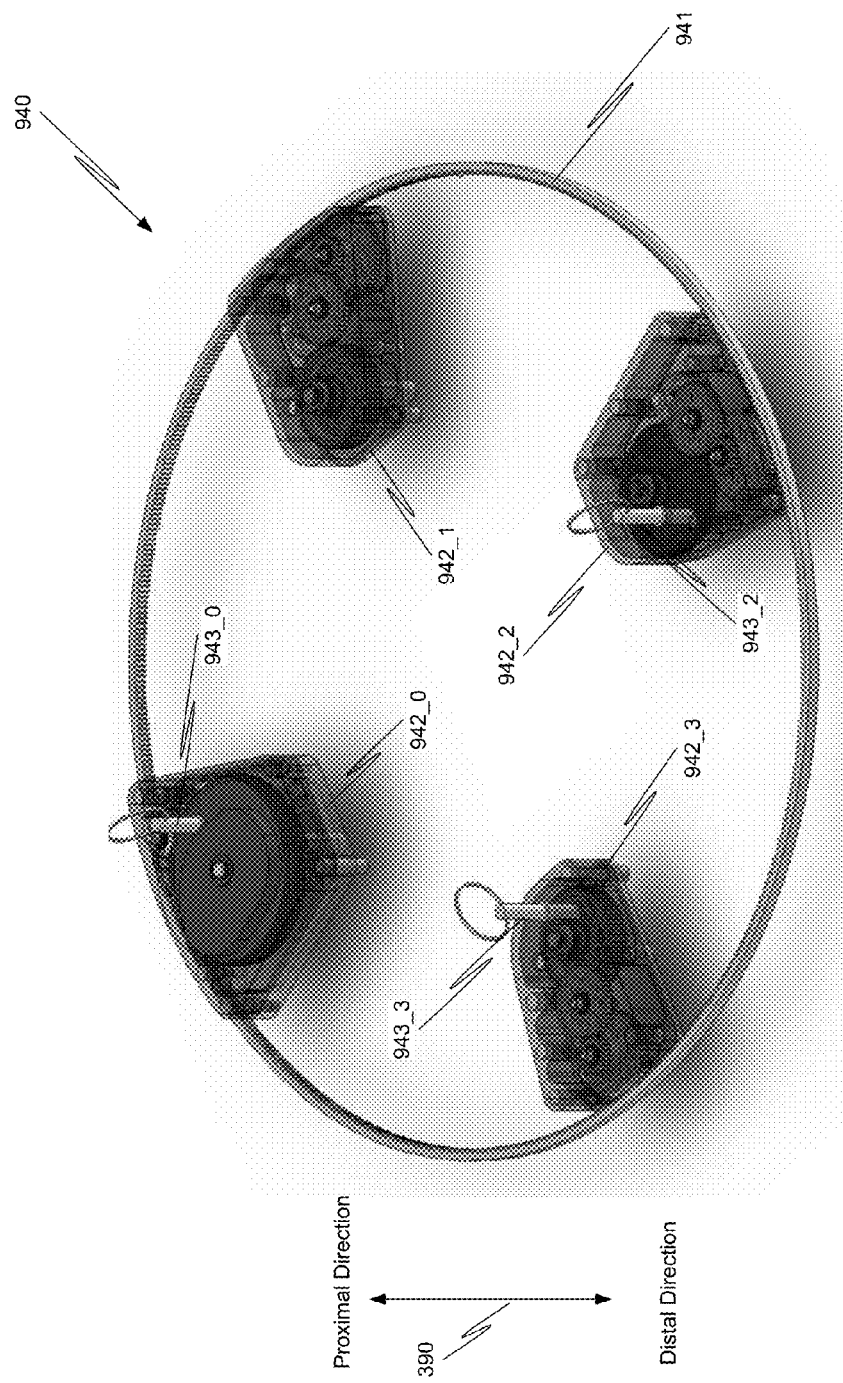
FIG. 9 illustrates yet another example of an instrument manipulator positioning system.

FIG. 9 illustrates another aspect of an instrument manipulator positioning system 940 that is included in entry guide manipulator 230E. Instrument manipulator positioning system 940 includes a lateral motion mechanism. The lateral motion mechanism includes an adjustment gear 941, sometimes referred to as a drive gear or an adjustment ring gear, and a plurality of gearboxes 942_0, 942_1, 942_2, 942_3. As described more completely below, each of gearboxes 942_0, 942_1, 942_2, 942_3 has an input spur gear, which engages adjustment gear 941, and an output pin. The output pin is the positioning element described above. Each positioning element mates with a positioning element receptacle in a floating platform, e.g., positioning element receptacle 710 in floating platform 700.

Each of gearboxes 942_0, 942_1, 942_2, 942_3 is installed with a release pin 943_0, 943_1, 943_2, 943_3. The release pin locks each gearbox during installation, which ensures that the gearboxes are properly synchronized. In FIG. 9, release pin 943_1 has been removed from gearbox 942_1.

In one aspect, turning adjustment gear 941 causes each of gearboxes 942_0, 942_1, 942_2, 942_3 to move the positioning element so that the floating platform coupled to the positioning element moves on a specific trajectory. As described previously, an insertion assembly is attached to the floating platform and a surgical device assembly is attached to the insertion assembly. Thus, as the positioning element moves the floating platform on the specific trajectory, the distal end of the surgical instrument shaft follows that specific trajectory.

In FIG. 9, gearboxes 942_0, 942_1, 942_2, 942_3 are representative of a set of gearboxes. In FIGS. 10A to 10D, a first set of gearboxes is illustrated. In FIGS. 11A to 11K, a second set of gearboxes is illustrated. The combination of gearboxes in a set is illustrative only and is not intended to be limiting. As explained more completely below, the particular combination of gearboxes used in a set of gearboxes for FIG. 9 is determined by the entry guides and instruments used with patient side support system 210E.

Also, the use of four gearbox sets is illustrative only and is not intended to be limiting. In view of this disclosure, a set of gearboxes can include any number of gearboxes, e.g., one for each manipulator assembly 240 that is to be automatically positioned. With a set of four gearboxes, each of the four manipulator assemblies in FIGS. 3A and 3B is automatically positioned. However, as explained above, some aspects may include more than four manipulator assemblies (see FIG. 5F) in a system, and so if all the manipulator assemblies are automatically positioned, the set of gearboxes can include more than four gearboxes in such a system. Similarly, if less than all of the manipulator assemblies were automatically positioned, the number of gearboxes in a set would be less than the total number of manipulator assemblies. FIG. 9 is not repeated for each of the possible combinations of gearboxes in a set, because in view of this disclosure, one knowledgeable in the field can select gearboxes for the number of manipulator assemblies that are automatically positioned to accommodate different instruments and/or guide tubes, e.g., the number of gearboxes in a set can vary from one up to the total number of manipulator assemblies in the system.

In one aspect, two types of gearboxes are used in a first set of gearboxes. A first gearbox moves the positioning element on a circular trajectory. A second gearbox moves the positioning element on a linear trajectory. In this aspect, a linear trajectory gearbox 942_0_1 (FIGS. 10C and 10D) is used for gearbox 942_0 (FIG. 9), while a circular trajectory gearbox 942 (FIGS. 10A and 10B) is used for each of gearboxes 942_1, 942_2, 942_3 (FIG. 9). This combination of gearboxes is illustrative only and is not intended to be limiting. As explained more completely below, the particular combination of gearboxes used in FIG. 9 is determined by the entry guides and instruments used with patient side support system 210E.

Figure 10A:
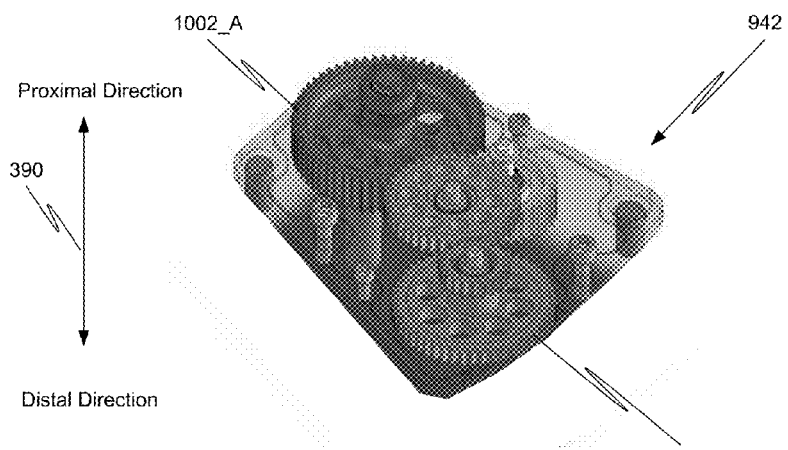
FIGS. 10A and 10B are proximal and distal views of a circular motion gearbox in a first set of gearboxes for the instrument manipulator positioning system of FIG. 9.
Figure 10B:
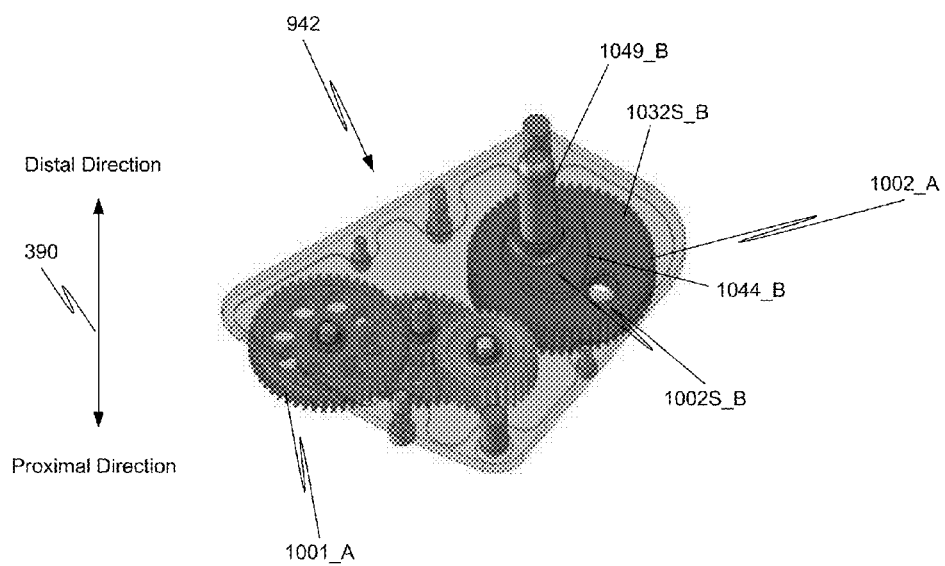

FIG. 10A is a proximal view of a gearbox 942. In this aspect, gearbox 942 represents each of gearboxes 942_1, 942_2, and 942_3 in FIG. 9, which have a circular trajectory. FIG. 10B is a distal view of gearbox 942. In FIGS. 10A and 10B, parts of the gearbox housing have been removed.

Gearbox 942 has a housing that supports a gear train including an input gear 1001_A and an output gear 1002_A. Above, input gear 1001_A was referred to as an input spur gear.

An output pin 1049_B, e.g., a positioning element, is mounted on a distal side surface 1002S_B of output gear 1002_A. In this aspect, output pin 1049_B is mounted on output gear 1002_A offset from the center of rotation of output gear 1002_A. Thus, the trajectory of output pin 1049_B and consequently, the shaft of the surgical instrument, is a constant radius arc. In one aspect, output pin 1049_B is a stainless steel pin, for example, Nitronic 60, thirty percent cold worked. However, any strong steel that operates well, i.e., does not exhibit galling or cold welding, with other steels can be used.

Output pin 1049_B extends distally from surface 1002S_B through an opening 1044_B in a distal side 1032S_B of the housing. A shape of opening 1044_B is selected to control the range of motion of output pin 1049_B. Thus, opening 1044_B is a motion stop for output pin 1049_B.

Figure 10C:
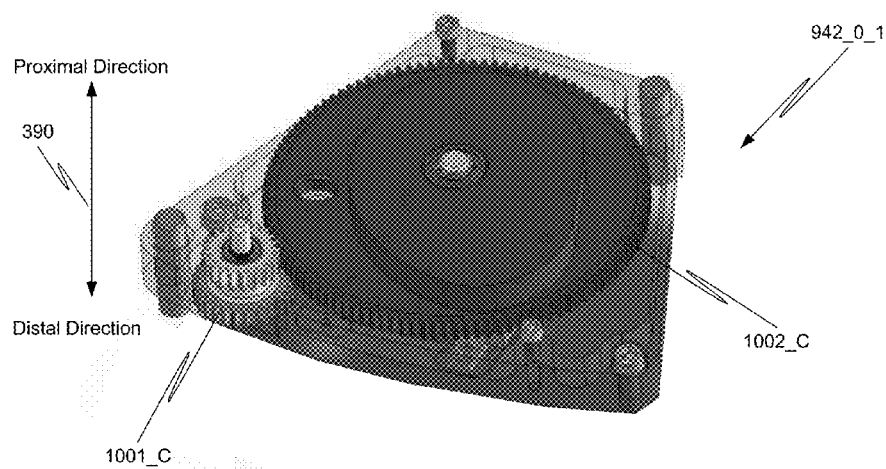
FIGS. 10C and 10D are proximal and distal views of a linear motion gearbox in the first set of gearboxes for the instrument manipulator positioning system of FIG. 9.
Figure 10D:
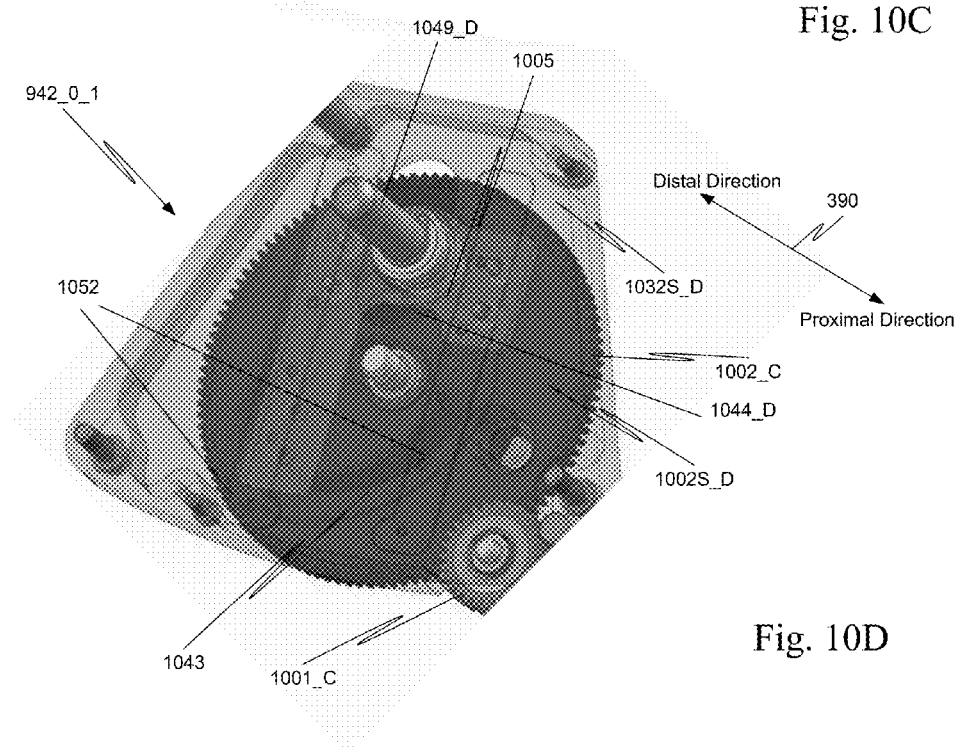

FIG. 10C is a proximal view of gearbox 942_0_1, which is a linear trajectory gearbox. Gearbox 942_0_1 is an example of gearbox 942_0 (FIG. 9). FIG. 10D is a distal view of gearbox 942_0_1. In FIGS. 10C and 10D, the gearbox housing is transparent so that the elements inside the housing can be seen.

Gearbox 942_0_1 has a housing that supports a gear train including an input gear 1001_C and a cam gear 1002_C. Cam gear 1002_C includes an adjustment cam 1043 that is a slot machined into cam gear 1002_C from distal surface 1002S_D (FIG. 10D). Thus, adjustment cam 1043 is sometimes referred to as cam slot 1043.

A proximal end of an output pin 1049_D, e.g., a proximal end of a positioning element, rides in adjustment cam 1043. Output pin 1049_D is mounted in a carriage 1005 that rides on a pair on linear rails 1052. Linear rails 1052 are mounted on an inner distal surface of the housing. In one aspect, output pin 1049_D is a stainless steel pin, for example, Nitronic 60, thirty percent cold worked. However, any strong steel that operates well, i.e., does not exhibit galling or cold welding, with other steels can be used.

Output pin 1049_D extends distally through a fixed slot 1044_D in a distal side 1032S_D of the housing. The size of fixed slot 1044_D is selected to control the range of motion of output pin 1049_D. Thus, fixed slot 1044_D is a motion stop for output pin 1049_D.

As input gear 1001_C drives cam gear 1002_C, adjustment cam 1043 moves output pin 1049_D. Normally, there would be a fair amount of friction between output pin 1049_D and cam slot 1043 as cam gear 1002_C rotates. However, in one aspect, a pair of bearings is mounted on output pin 1049_D where output pin 1049_D sits in cam slot 1043 so that gearbox 942_0_1 transmits the pin motion through bearing rolling action rather than sliding motion.

In gearbox 942_0_1, the position of output pin 1049_D is guided by the profile of adjustment cam 1043. However, carriage 1005 and linear rails 1052 restrict the movement of output pin 1049_D to motion on a straight line. This configuration has the benefit of being reversible, which makes the ordering of the output pin positions more flexible.

Figures 11A, 11B:
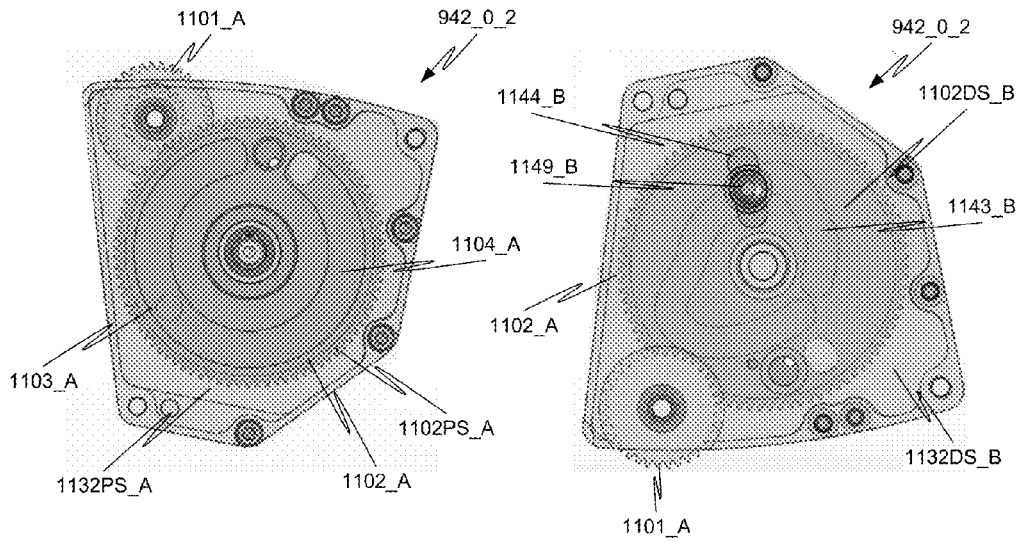
FIGS. 11A and 11B are proximal and distal views of a first gearbox in a second set of gearboxes for the instrument manipulator positioning system of FIG. 9.

In another aspect, a second set of gearboxes includes four different gearboxes as illustrated in FIGS. 11A to 11K. FIG. 11A is a proximal view of gearbox 942_0_2, which is a linear trajectory gearbox. Gearbox 942_0_2 is an example of 942_0 (FIG. 9). Gearbox 942_0_2 is a first gearbox in the second set of gearboxes, and typically is used to position a camera instrument. FIG. 11B is a distal view of gearbox 942_0_2. In FIGS. 11A and 11B, the gearbox housing is transparent so that the elements inside the housing can be seen. In FIG. 11A, release pin 943_0_2 has been removed from gearbox 942_0_2, and so is not shown.

Gearbox 942_0_2 has a housing that supports a gear train including an input gear 1101_A and a cam gear 1102_A. Cam gear 1102_A includes an adjustment cam 1143_B that is a slot machined into cam gear 1102_A from distal surface 1102DS_B (FIG. 11B). Thus, adjustment cam 1143_B is sometimes referred to as cam slot 1143_B.

A proximal end of an output pin 1149_B is coupled to a cam follower, e.g., a proximal end of a positioning element is coupled to a cam follower, which rides in adjustment cam 1143_B. Output pin 1149_B extends distally through a fixed slot 1144_B in a distal side 1132DS_B of the housing. The size of fixed slot 1144_B is selected based on the range of motion of output pin 1149_B. The width of fixed slot 1144_B is wide enough to accommodate the part of output pin 1149_B that rolls on an edge surface of the slot plus a tolerance.

In this aspect, a stop pin 1103_A extends in a proximal direction from proximal surface 1102PS_A of cam gear 1102_A. Stop pin 1103_A rides in a slot 1104_A in an interior surface of a proximal side 1132PS_A of the housing. Stop pin 1103_A in combination with slot 1104_A limits the range of rotation of cam gear 1102_A, and so the combination is a range of motion stop.

As input gear 1101_A rotates cam gear 1102_A, adjustment cam 1143_B moves output pin 1149_B in slot 1144_B. The position of output pin 1149_B is guided by the profile of adjustment cam 1143_D. However, slot 1144_B restrains the movement of output pin 1149_B to motion on a straight line. See FIG. 18C.

Figures 11C, 11D:
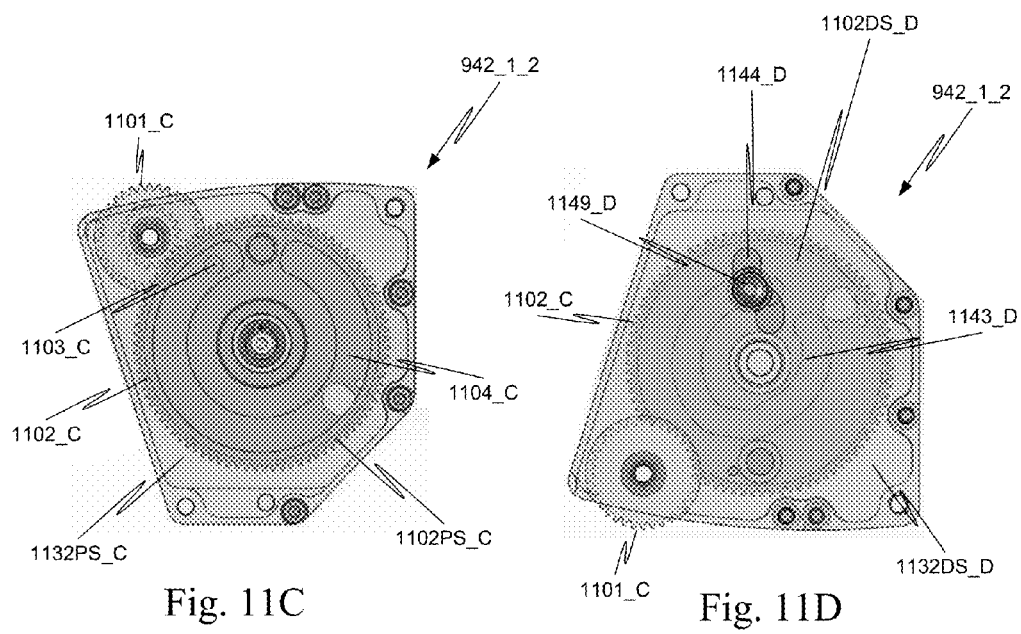
FIGS. 11C and 11D are proximal and distal views of a second gearbox in the second set of gearboxes for the instrument manipulator positioning system of FIG. 9.

FIG. 11C is a proximal view of gearbox 942_1_2, which is a first two degree-of-freedom trajectory gearbox. Gearbox 942_1_2 is an example of 942_1 (FIG. 9). Gearbox 942_1_2 is a second gearbox in the second set of gearboxes. FIG. 11D is a distal view of gearbox 942_0_2. In FIGS. 11C and 11D, the gearbox housing is transparent so that the elements inside the housing can be seen. In FIG. 11C, release pin 943_1_2 has been removed from gearbox 942_1_2, and so is not shown.

Gearbox 942_1_2 has a housing that supports a gear train including an input gear 1101_C and a cam gear 1102_C. Cam gear 1102_C includes an adjustment cam 1143_D that is a slot machined into cam gear 1102_C from distal surface 1102DS_D (FIG. 11B). Thus, adjustment cam 1143_D is sometimes referred to as cam slot 1143_D.

A proximal end of an output pin 1149_D is coupled to a cam follower, e.g., a proximal end of a positioning element is coupled to a cam follower, which rides in adjustment cam 1143_D. Output pin 1149_D extends distally through a fixed slot 1144_D in a distal side 1132DS_D of the housing. The size of fixed slot 1144_D is selected based on the range of motion of output pin 1149_D. The width of fixed slot 1144_D is wide enough to accommodate the part of output pin output pin 1149_D that rolls on an edge surface of the slot plus a tolerance.

In this aspect, a stop pin 1103_C extends in a proximal direction from proximal surface 1102PS_C of cam gear 1102_C. Stop pin 1103_C rides in a slot 1104_C in an interior surface of a proximal side 1132PS_C of the housing. Stop pin 1103_C in combination with slot 1104_C limits the range of rotation of cam gear 1102_C, and so the combination is a range of motion stop.

As input gear 1101_C rotates cam gear 1102_C, adjustment cam 1143_D moves output pin 1149_D in slot 1144_D. The position of output pin 1149_D is guided by the profile of adjustment cam 1143_D. However, slot 1144_D restrains the movement of output pin 1149_D to motion on a combination of two arcs. Output pin 1149_D has two degrees of freedom. See FIG. 18E.

Figures 11E, 11F:
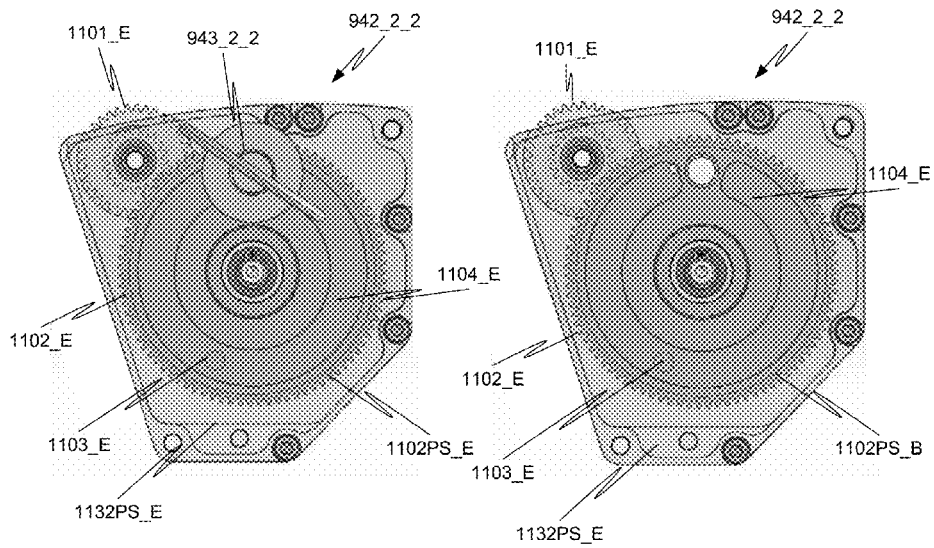
FIGS. 11E and 11F are proximal views of a third gearbox in the second set of gearboxes for the instrument manipulator positioning system of FIG. 9.
Figures 11G, 11H:
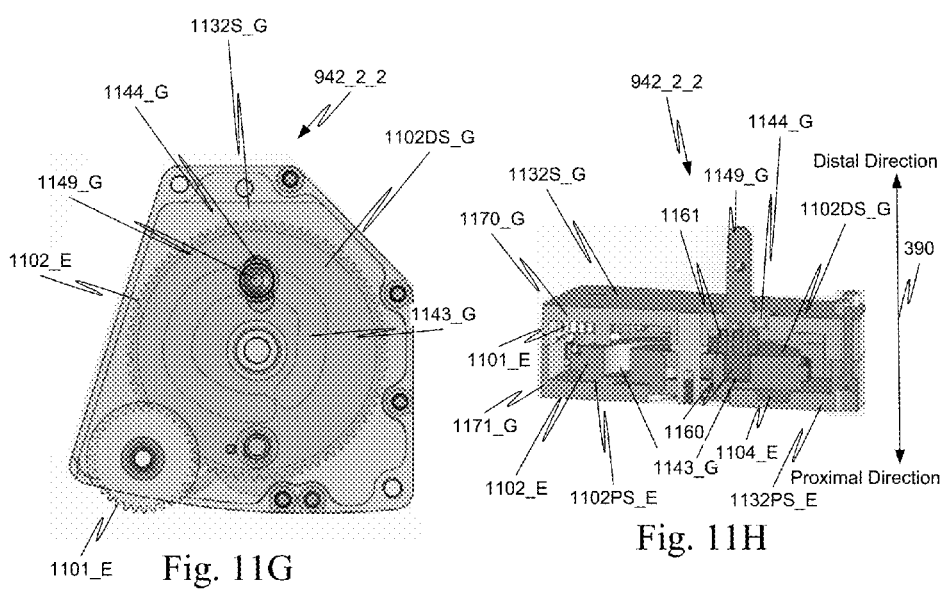
FIG. 11G is a distal view of the third gearbox in the second set of gearboxes for the instrument manipulator positioning system of FIG. 9.
FIG. 11H is a cross-sectional view of the third gearbox in the second set of gearboxes for the instrument manipulator positioning system of FIG. 9.

FIGS. 11E and 11F are proximal views of gearbox 942_2_2, which is a second two degree-of-freedom trajectory gearbox. Gearbox 942_2_2 is an example of 942_2 (FIG. 9). Gearbox 942_2_2 is a third gearbox in the second set of gearboxes. FIG. 11G is a distal view of gearbox 942_2_2. FIG. 11H is a cross-sectional view of gearbox 942_2_2. In FIGS. 11E, 11F, and 11G, the gearbox housing is transparent so that the elements inside the housing can be seen.

Gearbox 942_2_2 has a housing that supports a gear train including an input gear 1101_E and a cam gear 1102_E. Cam gear 1102_E includes an adjustment cam 1143_G that is a slot machined into cam gear 1102_E from distal surface 1102DS_G (FIG. 11B). Thus, adjustment cam 1143_G is sometimes referred to as cam slot 1143_G.

In FIG. 11E, release pin 943_2_2 is shown inserted in gearbox 942_2_2. As described previously, each release pin, e.g., release pin 943_2_2, locks its gearbox during installation, which ensures that the gearbox is properly synchronized with adjustment gear 941. In FIG. 11F, release pin 943_2_2 has been removed from gearbox 942_2_2.

A proximal end of an output pin 1149_G is coupled to a cam follower, e.g., a proximal end of a positioning element is coupled to a cam follower, which rides in adjustment cam 1143_G. Output pin 1149_G extends distally through a fixed slot 1144_G in a distal side 1132DS_G of the housing. The size of fixed slot 1144_G is selected based on the range of motion of output pin 1149_G. The width of fixed slot 1144_G is wide enough to accommodate the part of output pin 1149_G that rolls on an edge surface of the slot plus a tolerance.

In this aspect, a stop pin 1103_E extends in a proximal direction from proximal surface 1102PS_E of cam gear 1102_E. Stop pin 1103_E rides in a slot 1104_E in an interior surface of a proximal side 1132PS_E of the housing. Stop pin 1103_E in combination with slot 1104_E limits the range of rotation of cam gear 1102_A, and so the combination is a range of motion stop.

As input gear 1101_E rotates cam gear 1102_E, adjustment cam 1143_G moves output pin 1149_G in slot 1144_G. The position of output pin 1149_G is guided by the profile of adjustment cam 1143_G. However, slot 1144_G restrains the movement of output pin 1149_G to motion on a combination of a line and an arc. Output pin 1149_G has two degrees of freedom. See FIG. 18G.

Each of the other gearboxes in the second set, i.e., gearboxes 942_0_2, 942_1_2, and 942_3_2 has a cross-sectional view similar to the cross sectional view for gearbox 942_2_2 in FIG. 11H. Thus, a cross-sectional view of each gearboxes 942_0_2, 942_1_2, and 942_3_2 would not add any additional information, and so is not presented. As shown in FIG. 11H, in this aspect, output pin 1149_G is coupled to a cam follower 1160 by a bushing 1161. Cam follower 1160 rides in cam slot 1104_E. In this aspect, no bearings are used to support output pin 1149_G, because output pin 1149_G is supported by bearings 711 and 712 in positioning element receptacle assembly 714 (FIG. 7D). In this aspect, the housing of gearbox 942_2_2 includes a base 1170_G and a lid 1171_G.

Figures 11I, 11J:
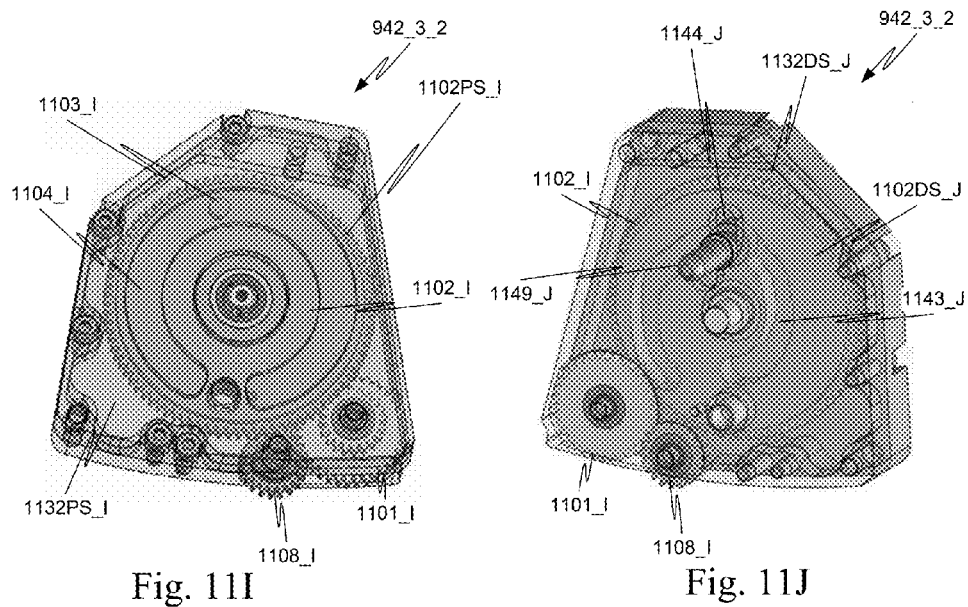
FIGS. 11I and 11J are proximal and distal views of a fourth gearbox in the second set of gearboxes for the instrument manipulator positioning system of FIG. 9.

FIG. 11I is a proximal view of gearbox 942_3_2, which is a third two degree-of-freedom trajectory gearbox. Gearbox 942_3_2 is an example of 942_3 (FIG. 9). Gearbox 942_3_2 is a fourth gearbox in the second set of gearboxes. FIG. 11J is a distal view of gearbox 942_3_2. In FIGS. 11I and 11J, the gearbox housing is transparent so that the elements inside the housing can be seen. In FIG. 11I, release pin 943_3_2 has been removed from gearbox 942_3_2, and so is not shown.

Gearbox 942_3_2 has a housing that supports a gear train including a reversing idler gear, 1108_I, an input gear 1101_I and a cam gear 1102_I. Reversing idler gear 1108_I rides on adjustment gear 941, and drives cam gear 1102_I. Reversing idler gear 1108_I is used, in this aspect, to assure that the manipulator positioning system does not enter an unstable state. Cam gear 1102_I includes an adjustment cam 1143_J that is a slot machined into cam gear 1102_I from distal surface 1102DS_J (FIG. 11J). Thus, adjustment cam 1143_J is sometimes referred to as cam slot 1143_J.

A proximal end of an output pin 1149_J is coupled to a cam follower, e.g., a proximal end of a positioning element is coupled to a cam follower, which rides in adjustment cam 1143_J. Output pin 1149_J extends distally through a fixed slot 1144_J in a distal side 1132DS_J of the housing. The size of fixed slot 1144_J is selected based on the range of motion of output pin 1149_J. The width of fixed slot 1144_J is wide enough to accommodate the part of output pin 1149_J that rolls on an edge surface of the slot plus a tolerance.

In this aspect, a stop pin 1103_I extends in a proximal direction from proximal surface 1102PS_I of cam gear 1102_I. Stop pin 1103_I rides in a slot 1104_I in an interior surface of a proximal side 1132PS_I of the housing. Stop pin 1103_I in combination with slot 1104_I limits the range of rotation of cam gear 1102_I, and so the combination is a range of motion stop.

As input gear 1101_I rotates cam gear 1102_I, adjustment cam 1143_J moves output pin 1149_J in slot 1144_J. The position of output pin 1149_J is guided by the profile of adjustment cam 1143_J. However, slot 1144_J restrains the movement of output pin 1149_J to motion on a combination of two arcs. Output pin 1149_J has two degrees of freedom. See FIG. 18I.

Figure 11K:
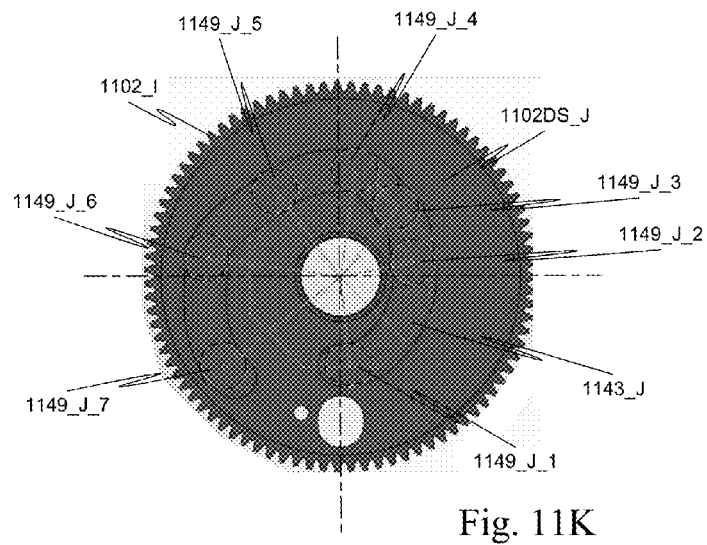
FIG. 11K is a more detailed illustration of the cam gear of FIG. 11J.

FIG. 11K is a more detailed diagram of cam gear 1102_I. In one aspect, output pin 1149_J is moved to one of seven positions by rotation of cam gear 1102_I. The seven positions of output pin 1149_J are represented by dotted lines 1149_J_1 to 1149_J_7 in cam slot 1143_J. The lighter colored lines in FIG. 11K are working lines and are not essential.

At each location where output pin 1149_J stops in cam slot 1143_J, the cam surface is flat, i.e., the flat surface of the cam is perpendicular to a radial line through the center of cam gear 1102_I. This prevents back driving of cam gear 1102_I. In some situations, surgical device assemblies 300 may be positioned such that the weight of a surgical device assembly transfers a force to the corresponding output pin for that assembly. The flat spots at the stop locations of output pin 1149_J assures that the only force transferred by the pin to cam gear 1102_I is a radial force through the center of cam gear 1102_I, and so back driving of cam gear 1102_I is not a problem. Cam gear 1102_I is also representative of the cam gears in each of the other gearboxes in the second set although the cam surfaces are not the same in each gearbox.

Another feature of cam gear 1102_I is that output pin 1149_J is moved to the appropriate stop position, as shown in FIG. 11K, by even increments of rotation of cam gear 1102. In this example, cam gear 1102_I is rotated ninety degrees to move output pin 1149_J from location 1149_J_1—the draping position—to location 1149_J_2 and then cam gear 1102_I is rotated forty-five degrees to move output pin 1149_J to each subsequent stop location, i.e., locations 1149_J_3 to 1149_J_7. Stop locations 1149_J_2 to 1149_J_7 are not at even increments in FIG. 11K because while cam gear 1102_I rotates in even increments, output pin 1149_J is constrained to move in cam slot 1143_J.

In one aspect, each of the gearboxes in the second set of gearboxes is constructed using the same materials. The base is made from 2024-T4 aluminum. The lid is made from 6061-T6 aluminum. All of the gears including the cam gear are made from 2024-T4 aluminum. In one aspect, each of the output pins is a stainless steel pin, for example, Nitronic 60, thirty percent cold worked, or 416 stainless steel. However, any strong steel that operates well, i.e., does not exhibit galling or cold welding, with other steels can be used. The materials mentioned here are illustrative only and are not intended to be limiting. Other equivalent metals and/or plastics could also be used.

In one aspect, a roll system and an instrument manipulator positioning system are both contained in entry guide manipulator 230E. The roll system includes a roll ring gear that is used to roll plurality of surgical device assemblies 300 (FIG. 3B). Adjustment ring gear 941 of instrument manipulator positioning system 940 interfaces with an input gear in each gearbox, e.g., gearboxes 942_0 to 942_3.

The output pin in each of the gearboxes is moved, for example, in one of two ways. The roll ring gear is held stationary, and the adjustment ring gear is rotated, or the adjustment ring gear is held stationary and the roll ring gear rotated. In general however, proper positioning can be obtained if one of the two gears is moved differentially with respect to the other gear, e.g., the two gears are moved with different angular velocity.

FIGS. 12A to 12D illustrate an example of an entry guide manipulator in which the roll ring gear is held stationary and the adjustment ring gear is rotated to move simultaneously each of the surgical device assemblies so that its instrument shaft is in the appropriate position for passing through a channel in an entry guide with damaging the surgical instrument. FIGS. 13A and 13D illustrate an example of an entry guide manipulator in which the adjustment ring gear is held stationary and the roll ring gear is rotated to move simultaneously each of the surgical device assemblies so that its instrument shaft is in the appropriate position for passing through a channel in an entry guide without damaging the surgical instrument. In both examples, during normal operations, the rotation of the roll ring gear and adjustment ring gear is synchronous, which means that that the two ring gears rotate together at the same angular velocity.

These examples are illustrative only and are not intended to be limiting. In view of this disclosure, other methods that move the roll ring gear and the adjustment ring gear asynchronously, e.g., move the two gears differentially, can be used to move the surgical device assemblies to the appropriate positions to enable passing their shafts through an entry guide, e.g., the two ring gears could be rotated at different angular velocities.

Figure 12A:
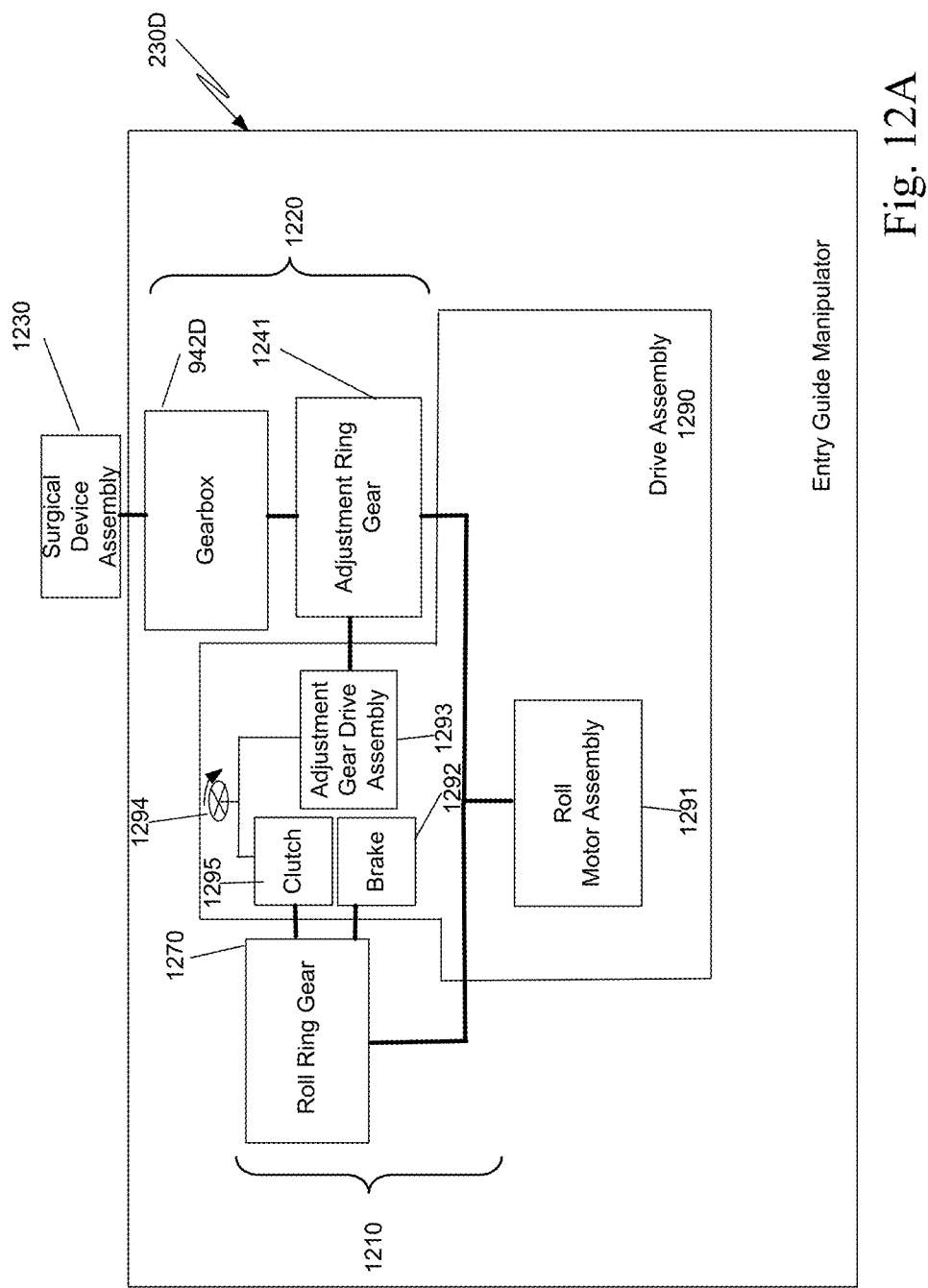
FIGS. 12A to 12D illustrate one aspect of an entry guide manipulator including an instrument manipulator positioning system.
Figure 13A:
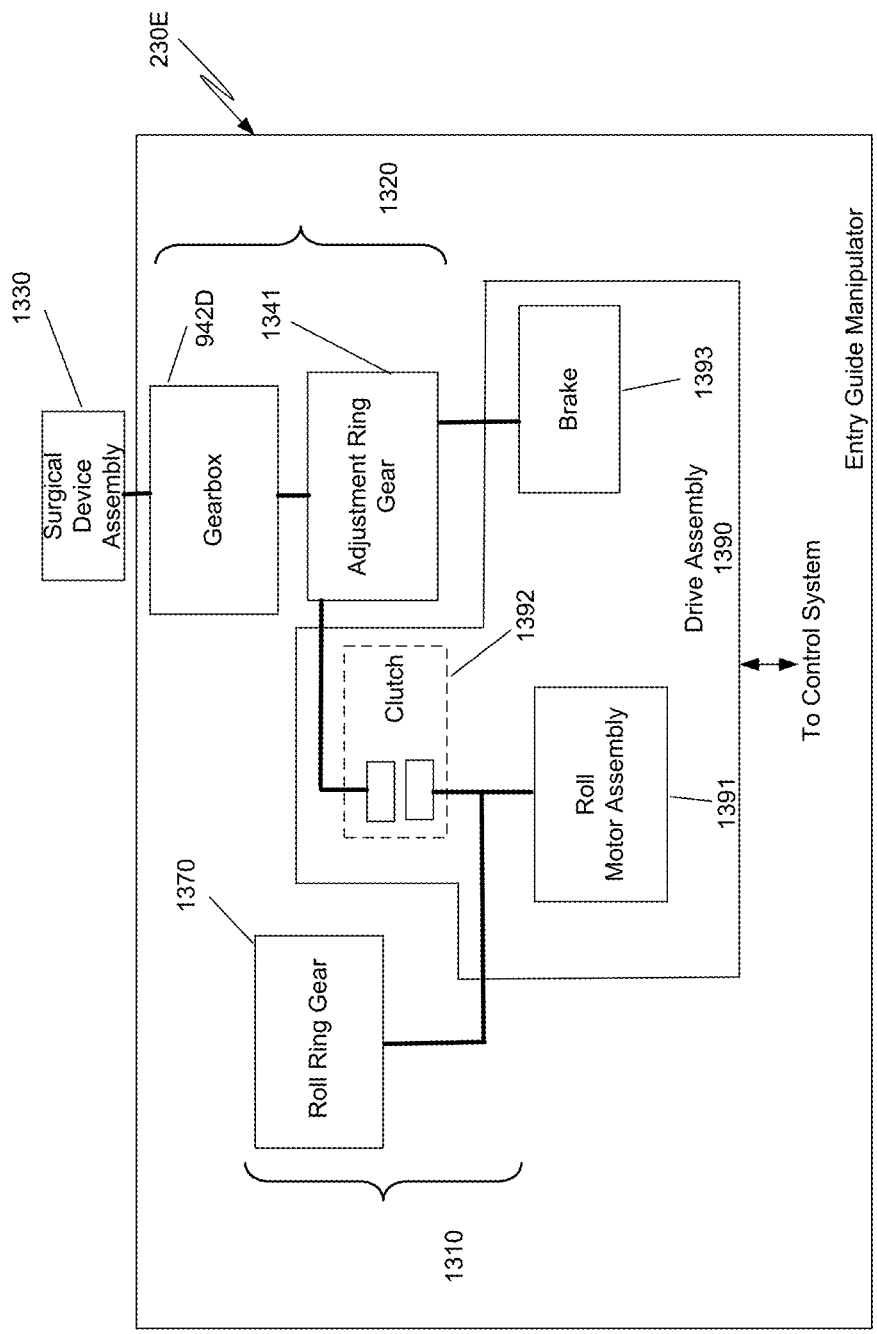
FIGS. 13A and 13D illustrate an alternative aspect of an entry guide manipulator including an instrument manipulator positioning system.

FIG. 12A is a schematic diagram of another aspect of an entry guide manipulator 230D with a roll system 1210 and an instrument manipulator positioning system 1220. Roll system 1210 rolls all of the surgical instruments assemblies coupled to entry guide manipulator 230D as a group. Instrument manipulator positioning system 1220 simultaneously moves all or some of the surgical instruments assemblies coupled to entry guide manipulator 230D, as needed, to align the shafts of the surgical device assemblies with different channels in an entry guide so that the shafts can enter and pass through the entry guide without exceeding the stress limits on the shafts if the shafts are bent upon entry to the entry guide.

A drive assembly 1290 is coupled to roll system 1210 and to instrument manipulator positioning system 1220. A surgical device assembly 1230 is coupled to manipulator position system 1220. While it not shown in FIG. 12A, surgical device assembly 1230 is also coupled to roll system 1210.

Roll system 1210 includes a roll ring gear 1270. Roll system 1210 includes other components, but these components are not shown in the drawings to facilitate the description of drive assembly 1290. Instrument manipulator positioning system 1220 includes an adjustment ring gear 1241 and a gearbox 942D. Gearbox 942D includes a positioning element. Surgical device assembly 1230 is coupled to the positioning element in gearbox 942D, for example as described above, so that when the positioning element moves the shaft of the instrument also is moved. When gearbox 942D moves the positioning element, the position the shaft of surgical device assembly 1230 moves in a plane, which in one aspect is a lateral plane that is perpendicular to a longitudinal axis of the entry guide.

In FIG. 12A, only a single gearbox 942D is shown for ease of discussion. However, adjustment ring gear 1241 engages a plurality of gearboxes in manner equivalent to that illustrated in FIG. 9 and each gearbox is couplable to a surgical device assembly. Surgical device assembly 1230 is equivalent to a surgical device in the plurality of surgical device assemblies 300 described above, and so that description is not repeated here.

Drive assembly 1290 includes a roll motor assembly 1291 that is coupled to roll ring gear 1270 and to adjustment ring gear 1241. Adjustment ring gear 1241 is sometimes referred to as an adjustment gear. In a roll operation, roll motor assembly 1291 drives roll ring gear 1270 and adjustment ring gear 1241 so that the rotation of the two gears is synchronized.

A brake 1292 and a clutch 1295 are coupled to roll ring gear 1270. An adjustment gear drive assembly 1293 is coupled to adjustment ring gear 1241. In this aspect, when clutch 1295 is disengaged by moving a knob 1294 with a linear motion, adjustment gear drive assembly 1293 can then be manually operated by turning knob 1294.

In a manipulator position adjustment process, knob 1294 disengages clutch 1295, and brake 1292 prevents roll ring gear 1270 from turning. Turning knob 1294 causes adjustment gear drive assembly 1293 to rotate adjustment ring gear 1241. Because roll ring gear 1270 is held stationary, gearbox 942D does not move. However, the rotation of adjustment gear drive assembly 1293 moves the positioning element in gearbox 942D, as described above, which in turn changes the position of the shaft of surgical device assembly 1230. The differential motion between roll ring gear 1270 and adjustment ring gear 1241 controls the movement of the positioning element in gearbox 942D.

Figure 12B:
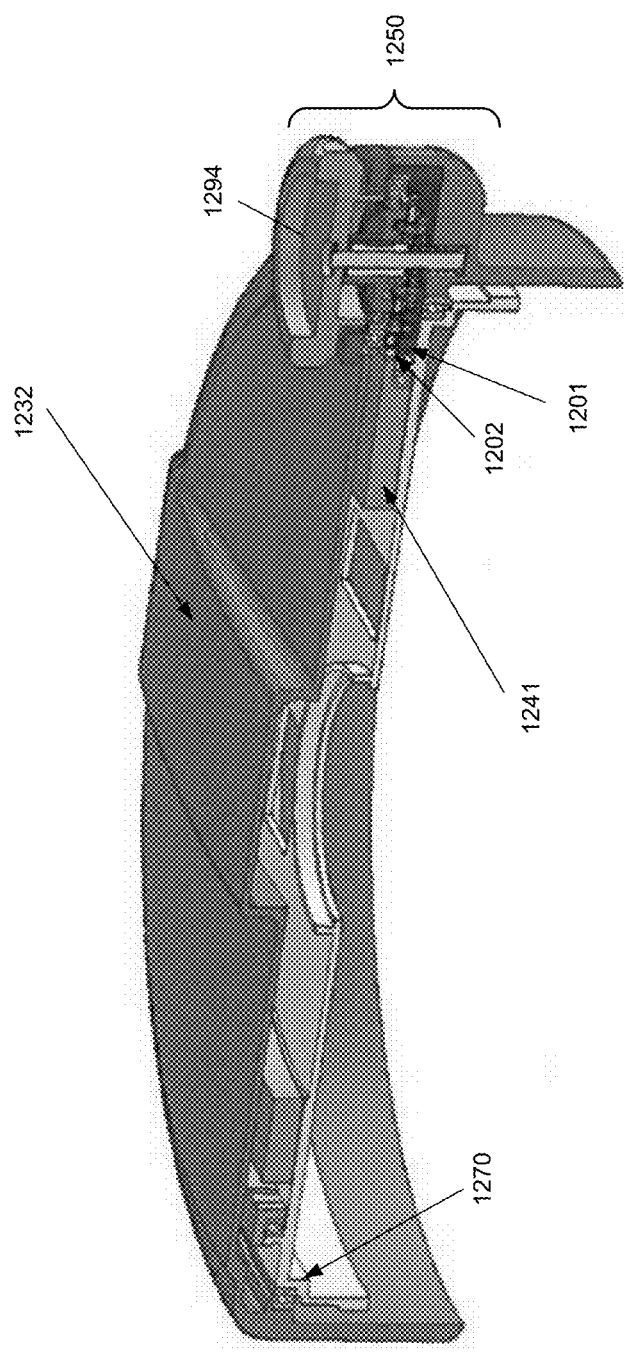

FIG. 12B illustrates one configuration with roll ring gear 1270 and adjustment ring gear 1241 mounted in a housing 1232 of entry guide manipulator 230D. In one aspect, adjustment ring gear 1241 can be either adjustment disk 841 or adjustment gear 941.

Figure 12C:
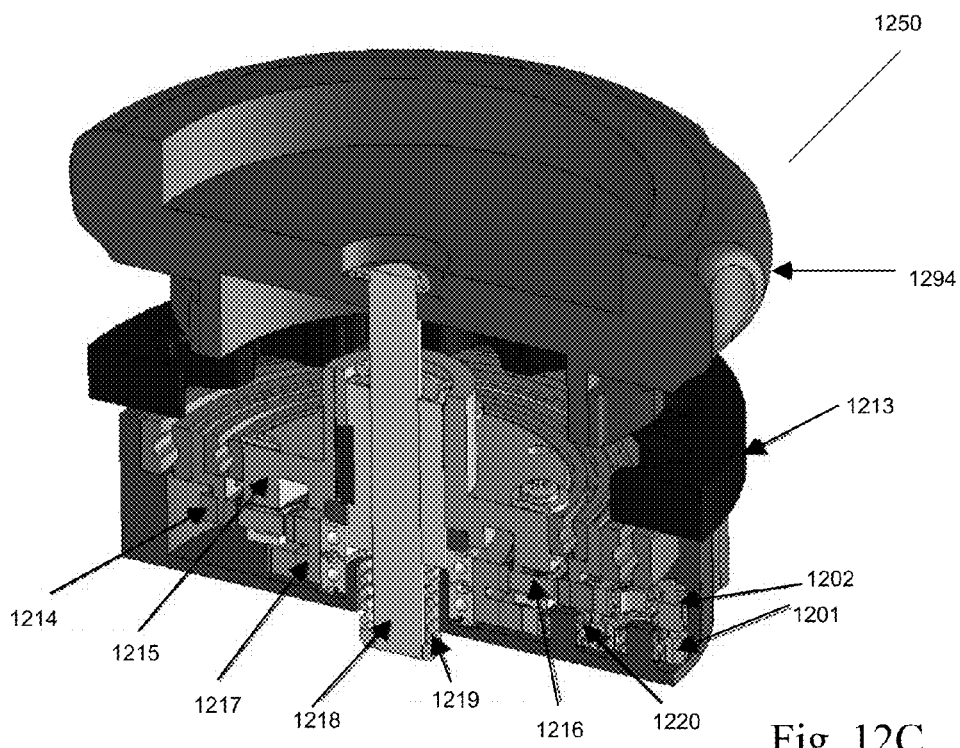
Figure 12D:
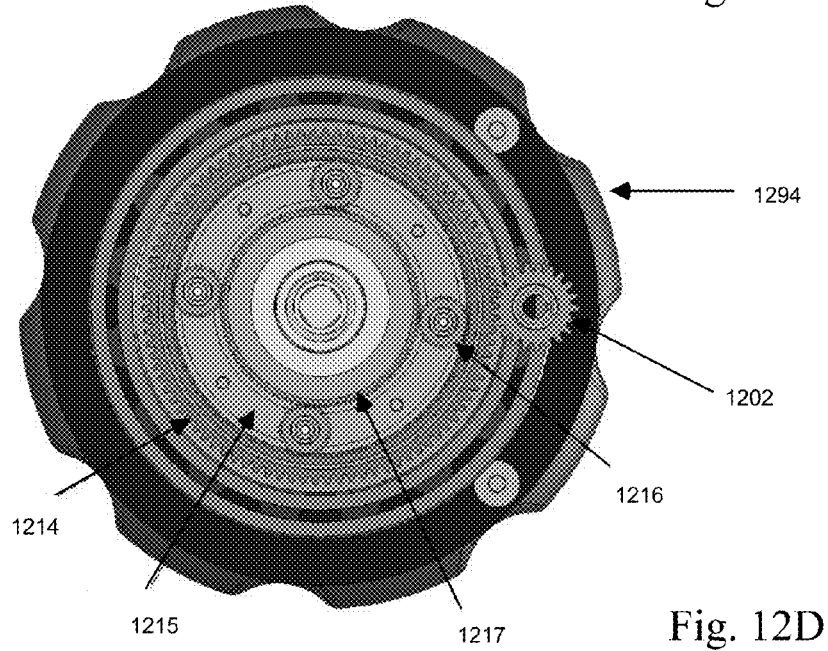

Roll ring gear 1270 rotates inside housing 1232 on a four-point contact bearing, in one aspect. Adjustment ring gear 1241 is free to rotate on roll ring gear 1270, and is driven by output gear 1202 (FIG. 12C) in a planetary gear differential mechanism 1250. FIG. 12C is a cross sectional view of one aspect of planetary gear differential mechanism 1250, while FIG. 12D is a bottom view of planetary gear differential mechanism 1250. Planetary gear differential mechanism 1250 is an example of an implementation of clutch 1295 and adjustment gear drive assembly 1293.

Motion of adjustment ring gear 1241 relative to roll ring gear 1270 is controlled by a user through a single manual knob 1294 located on housing 1232. Knob 1294 is mounted on a spline shaft 1218.

To drive adjustment ring gear 1241, the user pulls knob 1294 against knob preload spring 1219 to disengage knob 1294 from lock 1213 and then rotates knob 1294. When used this way, roll ring gear 1270 is disengaged from knob 1294 by clutch 1295 and brake 1292 prevents motion of roll ring gear 1270 (which effectively locks sun gear 1217), and the rotation of knob 1294 rotates planet carrier 1215. The rotation of planet carrier 1215 rotates planet gears 1216 that in turn drives ring gear 1214. Ring gear 1214 drives output gear 1202. The teeth on output gear 1202 mesh with teeth on the perimeter of adjustment ring gear 1241. Thus, the engagement of knob 1294 locks roll ring gear 1270, and the rotation of knob 1294 rotates adjustment ring gear 1241. The rotation of adjustment ring gear 1241 moves the positioning elements as described above. Gears 1201 and 1220 are idler gears configured to assist in proper operation of the structure.

The gear ratios of all components in planetary gear differential mechanism 1250 are selected to ensure that adjustment ring gear 1241 and roll ring gear 1270 are synchronized when the knob 1294 is locked and clutch 1295 is engaged. The gear ratios are also selected to get an adequate relationship between the knob rotation and adjustment disk rotation. In one aspect, positions on knob 1294 corresponding to positions of the positioning elements are communicated to the user as a ball-detent click, and the positions may have some over-center feel as well.

In this aspect, manual control of adjustment ring gear 1241 is used. In another aspect, knob 1294 is eliminated and spline shaft 1218 is coupled to a shaft of a servomotor or to a solenoid. The servomotor is configured to push or pull against preload spring 1219 to lock roll ring gear 1270 and engage adjustment ring gear 1241, as described above for manual operation.

FIG. 13A is a schematic diagram of another aspect of an entry guide manipulator 230E with a roll system 1310 and an instrument manipulator positioning system 1320. Roll system 1310 rolls all of the instruments assemblies coupled to system 1310 as a group. Instrument manipulator positioning system 1320 simultaneously positions all or some of the instruments assemblies coupled to system 1310 to enable insertion of shafts of the surgical device assemblies into different channels in an entry guide without damaging the instruments.

A drive assembly 1390 is coupled to roll system 1310 and to instrument manipulator positioning system 1320. A surgical device assembly 1330 is coupled to manipulator position system 1320. While it not shown in FIG. 13A, surgical device assembly 1330 is also coupled to roll system 1310.

Roll system 1310 includes a roll ring gear 1370. Instrument manipulator positioning system 1320 includes an adjustment ring gear 1341 and a gearbox 942D. Gearbox 942D includes a positioning element. Surgical device assembly 1330 is coupled to the positioning element in gearbox 942D, for example as described above. When gearbox 942D moves the positioning element, the position of the shaft of surgical device assembly 1330 moves in a plane, which in one aspect is a lateral plane. The lateral plane is perpendicular to the axis of rotation of entry guide manipulator 230E.

In FIG. 13A, only a single gearbox 942D is shown for ease of discussion. However, adjustment ring gear 1341 engages a plurality of gearboxes in manner equivalent to that illustrated in FIG. 9 and each gearbox is couplable to a surgical device assembly. Surgical device assembly 1330 is equivalent to surgical device assembly 300 described above, and so that description is not repeated here.

In this aspect, drive assembly 1390 includes a roll motor assembly 1391, a clutch 1392, and a brake 1393. Roll motor assembly 1391 is directly coupled to roll ring gear 1370 and is directly coupled to adjustment ring gear 1341 through clutch 1392, when clutch 1392 is engaged. When clutch 1392 is dis-engaged, roll motor assembly 1391 is not coupled to adjustment ring gear 1341.

Brake 1393 is directly coupled to adjustment ring gear 1341. When brake 1393 is engaged, brake 1393 prevents adjustment ring gear 1341 from turning. When brake 1393 is disengaged, adjustment ring gear 1341 can rotate.

In one aspect, clutch 1392 and brake 1393 are implemented as electromagnetic components. Clutch 1392 is implemented so that when power is applied to clutch 1392, clutch 1392 is released, i.e., dis-engaged, and when there is no power applied, clutch 1392 is engaged. Brake 1393 is implemented so that when power is applied, brake 1393 is released, and where there is no power brake is engaged.

Entry guide manipulator 230E, in one aspect, has at least three modes of operation: a roll mode, a fault mode, and an instrument manipulator positioning system adjustment mode. In the roll mode, the surgical device assemblies coupled to roll system 1310 are rolled as a group. In the fault mode, both roll system 1310 and instrument manipulator positioning system 1320 are disabled. In the instrument manipulator positioning system adjustment mode, each surgical device assembly coupled to system 1320 is individually moved so that its instrument shaft is in the appropriate position for passing through an entry guide without exceeding the stress limits for that shaft. Table 1 is an example of how the control system powers clutch 1392 and brake 1393 in each mode of operation.

TABLE 1

| Mode | Brake 1393 | Clutch 1392 |
|---|---|---|
| Roll | Energized = released | Not-energized = engaged |
| Fault | Not-energized = engaged | Not-energized = engaged |
| Adjustment | Not-energized = engaged | Energized = released |

Returning to FIG. 13A, in the roll mode, brake 1393 is released and clutch 1392 is engaged. Thus, roll motor assembly 1391 drives roll ring gear 1370 and adjustment ring gear 1341 so that the rotation of the two ring gears is synchronous.

In the fault mode, power is cut to both clutch 1392 and brake 1393. Thus, both brake 1393 and clutch 1392 are engaged. Brake 1393 prevents adjustment ring gear 1341 from rotating. Since roll ring gear 1370 is connected to adjustment ring gear 1341 through engaged clutch 1392, roll ring gear 1370 is also prevented from rotating by brake 1393. Thus, in the fault mode, any motion of either ring gear is inhibited.

In the adjustment mode, clutch 1392 is released, and brake 1393 is engaged. Thus, adjustment ring gear 1341 is preventing from rotating, while roll motor assembly 1391 rotates roll ring gear 1370. Roll ring gear 1370 is rotated until the difference in position between adjustment ring gear 1341 and roll ring gear 1370 is such that the instrument shafts are properly positioned.

In the prior example of FIGS. 12A to 12D, the gearboxes were held stationary, and motion of adjustment ring gear 1241 turned the input gears of the gearboxes to position the output pins. Here, the gearboxes are rotated relative to adjustment ring gear 1341 and this motion turns the gears in the gearbox so that that the output pins, the positioning elements, are moved to the correct location.

Figure 13B:
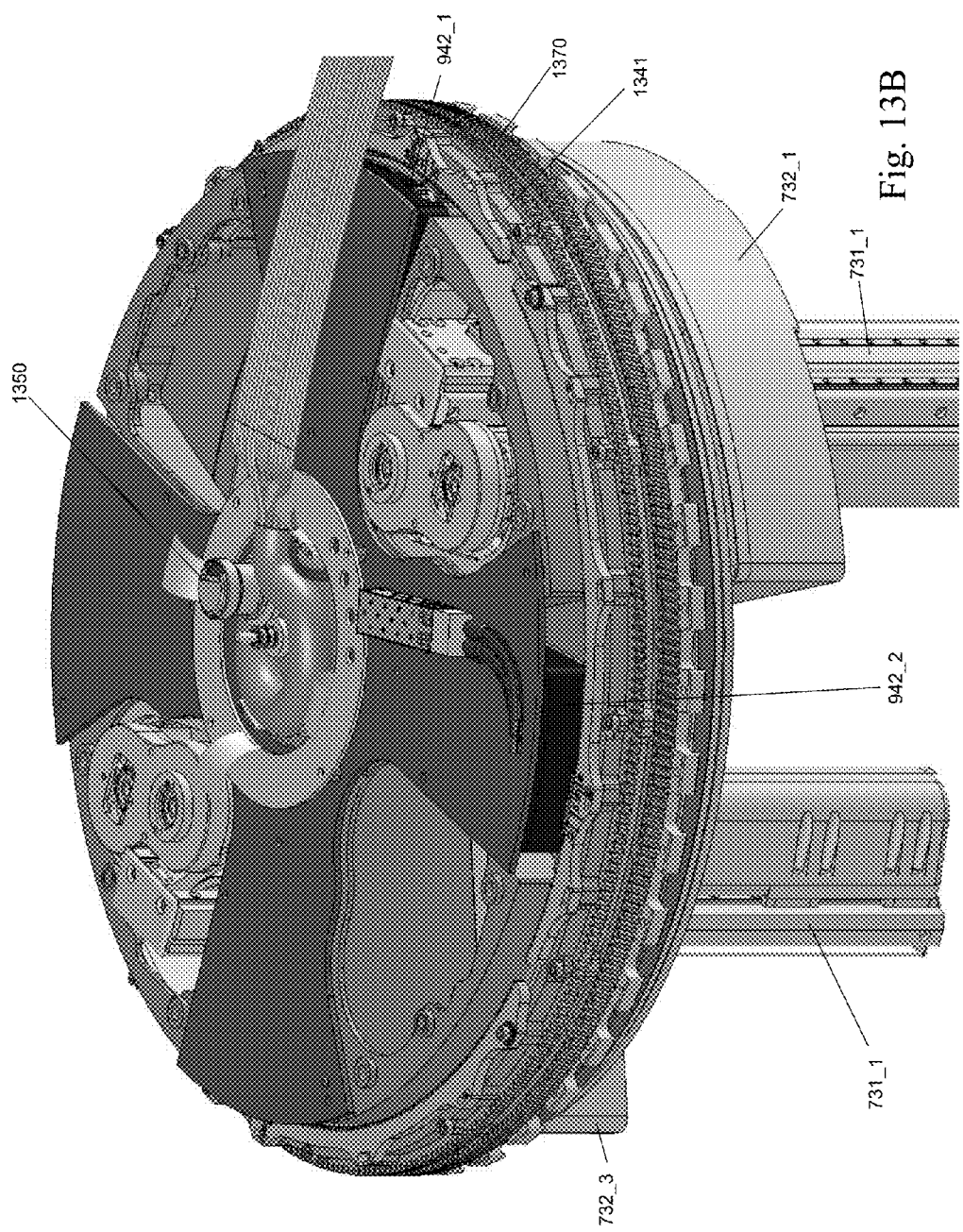
Figure 14A:
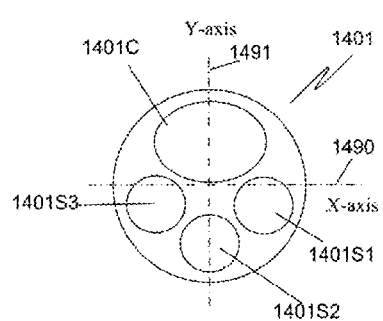
FIGS. 14A to 14J are illustrations of cross-sections of a family of entry guides that can be used with the systems of FIGS. 2A, 2C, and 2E.
Figure 14B:
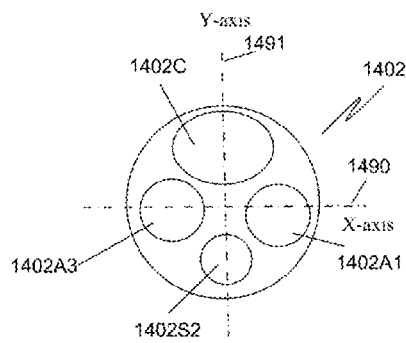
Figure 14C:
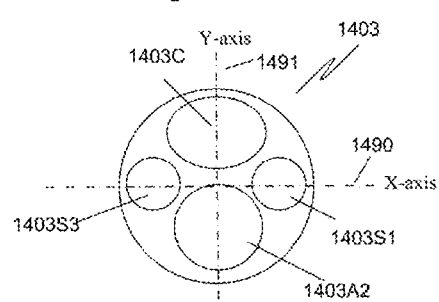
Figure 14D:
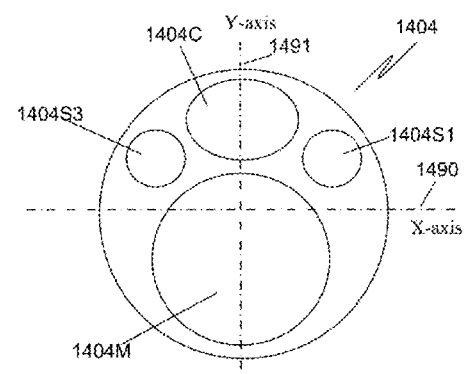
Figure 14E:
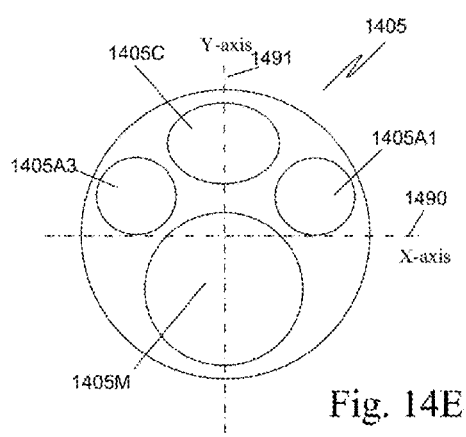
Figure 14F:
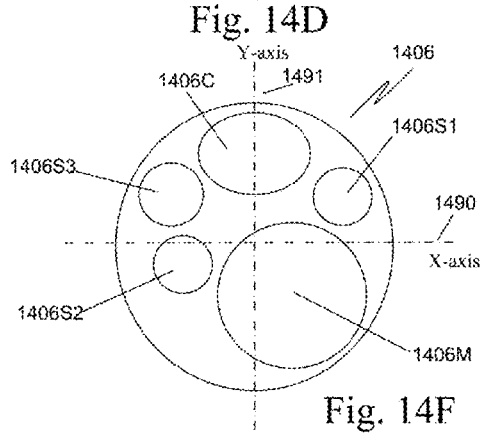
Figure 14H:
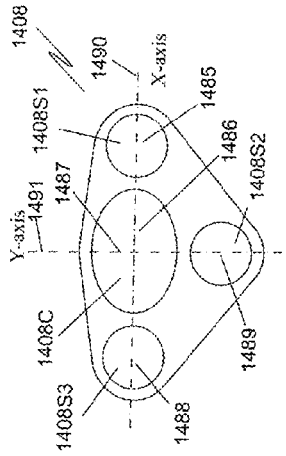
Figure 14J:
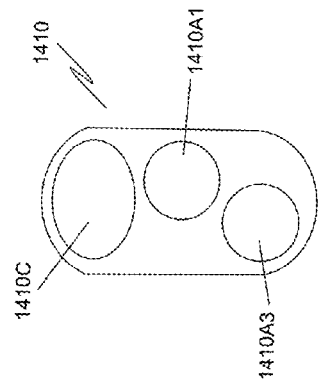
Figure 14G:
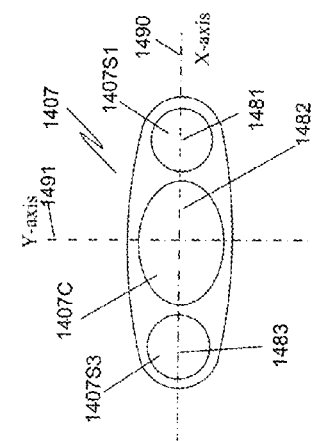
Figure 14I:
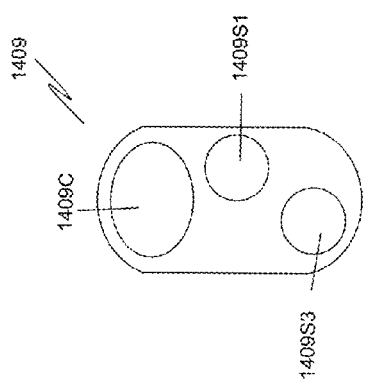

FIGS. 13B to 13D are more detailed illustrations of one aspect of implementing entry guide manipulator 230E of FIG. 13A. FIG. 13B is an illustration of entry guide manipulator 230E with the cover removed. Gearboxes 942_1, 942_2 (see FIG. 9), base assemblies 732_1, 732_3 (see FIGS. 7A to 7C), and insertion assemblies 731_1, 731-3 (see FIGS. 7A to 7C) are visible in FIG. 13B. The outer gear teeth of adjustment ring gear 1341 and the gear teeth of roll ring gear 1370 are also visible in FIG. 13B. The outer diameter of adjustment ring gear 1341 is the same as the outer diameter as roll ring gear 1370. Digital potentiometer 1350 measures the absolute position of roll ring gear 1370 with respect to a mechanical ground of entry guide manipulator 230E.

FIG. 13C is a cut away illustration that shows the interface between adjustment ring gear 1341 and input gear 1001 of gearbox 942_1. The gear teeth of input gear 1001 engage the inner gear teeth of adjustment ring gear 1341.

FIG. 13D is a cut away illustration of a drive assembly 1390 for roll gear assembly 1310 and instrument manipulator positioning system 1320. Motor assembly 1391, clutch 1392, brake 1393, and a second potentiometer 1351 are mounted in a housing 1394 of drive assembly 1390. As used herein, a clutch connects and disconnects one shaft to and from another shaft, and a brake connects and disconnects a shaft to and from ground.

Motor output gear 1317 drives roll gear train 1371, and roll gear train 1371 drives roll ring gear 1370. Roll gear train 1371 includes a roll input gear 1372 and a roll output gear 1373. Roll input gear 1372 and a roll output gear 1373 spin together.

Adjustment gear train 1360 is coupled to roll gear train 1371 by clutch 1392. Sometimes adjustment gear train 1360 is referred to as instrument manipulator positioning system gear train 1360. Adjustment gear train 1360 drives adjustment ring gear 1341. Adjustment gear train 1360 includes an adjustment input gear 1361 and an adjustment output gear 1362. Adjustment input gear 1361 and adjustment output gear 1362 spin together.

The ratios of the gears in roll gear train 1371 and in adjustment gear train 1360 are the same. Thus, when both gear trains 1371 and 1360 are driven by motor 1391, roll ring gear 1370 and adjustment ring gear 1341 rotate synchronously, e.g., roll ring gear 1370 and adjustment ring gear 1341 spin one to one.

In this example, roll motor assembly 1391 is a compact high torque slotless brushless direct current motor 1312 with a shaft 1313. Roll motor assembly 1391 includes a hall sensor assembly 1314 and an encoder 1315. Motor shaft 1313 is coupled to a harmonic gear drive 1316. Harmonic gear drive 1316 is coupled to a motor output gear 1317.

As is known to those knowledgeable in the field, harmonic gear drive 1316 includes three components: a wave generator, a flexspline, and a circular spline. Harmonic gear drive 1316 has zero backlash, high positional accuracy relative to other gearing technologies, and a high torque-to-weight ratio relative to other gearing technologies.

Motor output gear 1317 drives roll input gear 1372 in a roll system gear train 1371. Roll input gear 1372 is mounted on a pair of bearings. The pair of bearings is mounted on shaft 1331 of clutch 1392. A hub 1335 of clutch 1392 is affixed to roll input gear 1372 in roll system gear train 1371.

Shaft 1331 of clutch 1392 is rotatably mounted in housing 1394 using a bearing on each end of shaft 1331. Adjustment input gear 1361 of instrument manipulator positioning system gear train 1360 is fixedly mounted on shaft 1331 so that as shaft 1331 spins, adjustment input gear 1361 rotates.

Hub 1335 of clutch 1392 is mounted on shaft 1331 through a hub on roll input gear 1372. Armature 1334 contains permanent magnets and is connected mechanically to hub 1335 by leaf springs so that armature 1334, hub 1335, and roll input gear 1372 rotate as a unit about shaft 1331.

Rotor 1333 is mounted on shaft 1331 so that when rotor 1333 spins, shaft 1331 spins also. When there is no power applied to electromagnetic coil 1332, permanent magnet armature 1334 also attaches to rotor 1333 and so adjustment input gear 1361 rotates synchronously with roll input gear 1372 when brake 1393 is not engaged.

When power is applied to electromagnetic coil 1332, the current flow through electromagnetic coil 1332 creates a magnetic field that magnetizes rotor 1333 so that there is no longer any magnetic attachment between rotor 1333 and armature 1334. The leaf springs connecting armature 1334 and hub 1335 pull the armature 1334 upward and separate the armature 1334 from the rotor 1333. Thus, armature 1334 and rotor 1333 are disconnected and shaft 1331 is no longer coupled to roll input gear 1372. This allows roll input gear 1372 to rotate without rotating adjustment input gear 1361 as clutch 1392 is disengaged.

Roll input gear 1372 drives roll output gear 1373 of roll system gear train 1371. Roll output gear 1373 is mounted on a pair of bearings. The pair of bearings is mounted on shaft 1322 of brake 1393. Roll output gear 1373 is engaged with roll ring gear 1370.

Shaft 1322 of brake 1393 is rotatably mounted in housing 1394 using a bearing on each end of shaft 1322. Adjustment output gear 1362 of instrument manipulator positioning system gear train 1360 is fixedly mounted on shaft 1322 so that when shaft 1331 is free to spin, adjustment output gear 1362 rotates. Adjustment output gear 1362 is driven by adjustment input gear 1361 of instrument manipulator positioning system gear train 1360.

A hub 1324 of brake 1393 is mounted on shaft 1322 adjacent a body 1323 that includes an electromagnetic coil and permanent magnets. Body 1323 is affixed to drive housing 1394. An armature 1325 is connected to hub 1324 by leaf springs. When the electromagnetic coil in body 1323 is not energized, armature 1325 is affixed to body 1323 by the magnetic lines of flux of permanent magnets in body 1323. Thus, in this state, shaft 1322 is connected to housing 1394, e.g., shaft 1322 is connected to ground. Thus, shaft 1322 cannot spin and so adjustment output gear 1362 of instrument manipulator positioning system gear train 1360 is held in position and cannot rotate. When power is applied to the electromagnetic coil in body 1323, a magnetic field is generated that cancels the magnetic field of the permanent magnets in body 1323, and leaf springs connecting hub 1324 and armature 1325 pull armature 1325 upward and separate armature 1325 from body 1323. Thus, shaft 1322 is free to spin, i.e., brake 1393 is released.

Roll output gear 1373 of roll system gear train 1371 drives roll ring gear 1370. Adjustment output gear 1362 of instrument manipulator positioning system gear train 1360 drives adjustment ring gear 1341. One end of brake shaft 1322 is coupled to a second digital potentiometer 1351 that is mounted on drive housing 1394. Digital potentiometer 1351 measures the absolute position of adjustment ring gear 1341 with respect to the mechanical ground.

Thus, first digital potentiometer 1350 (FIG. 13B) measures the absolute position of roll ring gear 1370 with respect to the mechanical ground, while second digital potentiometer 1351 measures the absolute position of adjustment ring gear 1341 with respect to the same mechanical ground. In the roll mode (see Table 1) when roll ring gear 1370 and adjustment ring gear 1341 rotate synchronously, first digital potentiometer 1350 and second digital potentiometer 1351 both turn. In the adjustment mode, adjustment ring gear 1341 is braked and so second digital potentiometer 1351 does not turn. However, first digital potentiometer 1350 does turn and is incremented. The configuration of the surgical device assemblies is determined by the difference between first digital potentiometer and second digital potentiometer in the adjustment mode, i.e., by the relative position of roll ring gear 1370 to adjustment ring gear 1341.

As described above, patient side support system 210E is used for a variety of surgical procedures that use various combinations of instruments. Also as described above, the instruments in one aspect are grouped into sets of instruments based on the shaft characteristics of the instruments, e.g., standard surgical instrument, advanced surgical instruments, and camera instruments. Also, in some surgeries, a manual instrument or instruments may be used in conjunction with the teleoperated surgical instruments.

In one aspect, each standard surgical instrument has a shaft with a specified outer diameter, e.g., a 6 mm (0.237 in) outer diameter. The outer diameter of the shaft of an advanced surgical instrument is larger than the outer diameter of the shaft of the standard surgical instrument. In one aspect, advanced surgical instruments have shafts with outer diameters of 8 mm (0.315 in) and 12 mm (0.473 in). Examples of advanced surgical instruments include a stapler and a vessel sealer.

System 210E has the flexibility to accommodate a specific combination of these instruments for a particular procedure, as well as a camera instrument. In one aspect, a number of different entry guides are used in system 210E. Each different entry guide includes a different configuration of channels, as described more completely below. The channels include standard instrument channels, advanced instrument channels, camera channels, and manual channels in one aspect. In another aspect, manual channels are not included and can be eliminated or replaced with a standard instrument channel or an advanced instrument channel. The standard instrument channels are sometimes referred to as standard surgical instrument channels. The advanced instrument channels are sometimes referred to as advanced surgical instrument channels.

The selection of entry guides and cannula sizes for system 210E was based on clinical needs, system feasibility, logistics, and manufacturability. The instrument channels in the entry guides were sized to include a sheath mounted on the surgical instrument. The sheath prevents tissue or entry guide features from catching on the instrument joints.

In one aspect, the minimum spacing between channels in an entry guide was selected to provide a minimum webbing thickness based on manufacturability, e.g., a minimum thickness between adjacent channels of 0.046 inches (1.17 mm). Similarly, the minimum outer wall thickness of the entry guide was selected based on manufacturability, e.g., a minimum outer wall thickness of 0.035 inches (0.89 mm). The diameter of the entry guide channel for manual instruments was made as large as possible while maintaining the minimum outer wall thickness and minimum thickness between adjacent channels.

FIGS. 14A to 14J are illustrations of cross-sections of a family of entry guides that can be used with system 210E. The inclusion of ten entry guides in the family is illustrative only and is not intended to be limiting. The number of entry guides in the family depends, for example, on the number of different types of surgical instruments used in a surgical procedure and the number of surgical procedures that require different shaped entry guides and/or different types and numbers of surgical instruments. In one aspect, each entry guide in the family includes the characteristics just described. The family of entry guides can be grouped into kits of two or more entry guides. Each entry guide includes a plurality of channels. A channel is defined by an interior wall or by interior walls of the entry guide.

As indicated above, each entry guide is inserted in a cannula. Each cannula has a common wall thickness. The wall of the cannula is made as thin as possible to minimize incision size, but thick enough to support the working loads. In addition, the thickness of the wall is large enough that the distal end of the cannula does not have a knife edge. The entry guides were selected to minimize the number of different sized cannulas required. For entry guides with a circular cross section, two cannula sizes were selected, e.g., cannulas with an inner diameter of about 25 mm (0.986 in) and about 31 mm (1.222 in). For entry guides with a non-circular cross section, the smallest circular cannula size is reported that permits that non-circular entry guide to roll about the longitudinal axis of entry guide manipulator 230 assuming that roll is allowed. However, typically non-circular entry guides and cannulas do not roll.

Hence, the ten entry guides presented in FIGS. 14A to 14J require at a minimum three cannula sizes. A standard 25 mm inner diameter cannula is used with standard entry guide 1401. A 31 mm inner diameter cannula is used with the other circular cross section entry guides. Both the 25 mm cannula and the 31 mm cannula have two sizes—a short length and a long length—for accommodating different patient anatomies. The non-circular cross section cannulas would require a cannula with a 36 mm (1.420 in) inner diameter if roll was possible in the procedure. A non-circular entry guide placed between ribs typically would not be rolled.

The positions of instrument channels in the various non-circular cross section entry guides were adjusted (inward) from hugging the outer perimeter of the entry guide to fit within limitations of the instrument manipulator positioning system, as described more completely below. Four unique non-circular cross section entry guides are included in the family of entry guides, one in a horizontal configuration for transoral surgery, one in a cross arm configuration for transoral surgery, and two in a vertical configuration for intercostal surgery.

Entry guide 1401 (FIG. 14A) is referred to as a standard entry guide and is the same as entry guide 571S. Entry guide 1401 has a circular cross section. Entry guide 1401 includes four channels. The four channels are a camera channel 1401C and three standard surgical instrument channels 1401S1, 1401S2, 1401S3. Camera channel 1401C has an oblong cross section. Herein, an oblong channel refers to a channel having an oblong cross section. Standard surgical instrument channels 1401S1, 1401S2, 1401S3 have a circular cross section. Herein, a circular channel refers to a channel having a circular cross section. In this aspect, each of the three circular standard surgical instrument channels 1401S1, 1401S2, 1401S3 is the same size, i.e., has the same diameter, e.g., 0.310 inches (7.9 mm).

Entry guide 1402 (FIG. 14B) is a first example of an advanced instrument entry guide. Entry guide 1402 has a circular cross section. Entry guide 1402 includes four channels. The four channels are an oblong camera channel 1402C, a first circular advanced surgical instrument channel 1402A1, a circular standard surgical instrument channels 1402S2, and a second circular advanced surgical instrument channel 1402A3. In this aspect, first and second circular advanced instrument channels 1402A1, 1402A3 have a same diameter, e.g., 0.428 inches (10.9 mm).

Entry guide 1403 (FIG. 14C) is a second example of an advanced instrument entry guide. Entry guide 1403 has a circular cross section. Entry guide 1403 includes four channels. The four channels are an oblong camera channel 1403C, a first circular standard instrument channel 1403S1, a circular advanced surgical instrument channel 1403A2, and a second circular standard surgical instrument channels 1403S3. In this aspect, first and second circular standard surgical instrument channels 1403S1, 1403S3 have a same diameter, e.g., 0.310 inches (7.9 mm). In one aspect, circular advanced surgical instrument channel 1403A2 is sized for a stapler, and has, for example, a diameter of 0.595 inches (15.1 mm).

Entry guide 1404 (FIG. 14D) is a first example of a manual port entry guide. Entry guide 1404 has a circular cross section. Entry guide 1404 includes four channels. The four channels are an oblong camera channel 1404C, a first circular standard instrument channel 1404S1, a circular manual channel 1404M, and a second circular standard surgical instrument channels 1404S3. In this aspect, first and second circular standard surgical instrument channels 1404S1, 1404S3 have a same diameter, e.g., 0.310 inches (7.9 mm). In one aspect, circular manual channel 1404M has a diameter of 0.671 inches (17 mm).

Entry guide 1405 (FIG. 14E) is a second example of a manual port entry guide. Entry guide 1405 has a circular cross section. Entry guide 1405 includes four channels. The four channels are an oblong camera channel 1405C, a first circular advanced instrument channel 1405A1, a circular manual channel 1405M, and a second circular advanced surgical instrument channels 1405A3. In this aspect, first and second circular advanced surgical instrument channels 1405A1, 1405A3 have a same diameter, e.g., 0.428 inches (10.9 mm). In one aspect, circular manual channel 1405M has a diameter of 0.472 inches (12 mm).

Entry guide 1406 (FIG. 14F) is a third example of a manual port entry guide. Entry guide 1406 has a circular cross section. Entry guide 1406 includes five channels. The five channels are an oblong camera channel 1406C, three circular standard instrument channels 1406S1, 1406S2, 1406S3, and a circular manual channel 1406M. In this aspect, each of the three circular standard surgical instrument channels 1406S1, 1406S2, 1405S3 is the same size, i.e., has the same diameter, e.g., 0.310 inches (7.9 mm). In one aspect, circular manual channel 1406M has a diameter of 0.505 inches (12.8 mm).

Entry guide 1407 (FIG. 14G) is a first example of a transoral entry guide, i.e., entry guide 1407 is used in minimally invasive transoral surgery. Entry guide 1407 can also be used in minimally invasive thoracic surgery. Entry guide 1407 has a non-circular cross section, e.g., an oblong cross section. The oblong cross section of entry guide 1407 has a major axis 1490 and a minor axis 1491. Major axis 1490 is perpendicular to minor axis 1491. Entry guide 1407 includes three channels. The three channels are an oblong camera channel 1407C and two circular standard instrument channels 1407S1, 1407S3. In this aspect, first and second circular standard surgical instrument channels 1407S1, 1407S3 have a same diameter, e.g., 0.310 inches (7.9 mm). First circular standard surgical instrument channel 1407S1 has a lengthwise axis 1481. The oblong cross section of camera channel 1407C has a major axis 1482, and second circular standard surgical instrument channel 1407S2 has a lengthwise 1483. Major axis 1482 is coincident with major axis 1490 of the oblong cross section of entry guide 1407. Lengthwise axis 1481 and lengthwise axis 1483 intersect major axis 1490. First and second circular standard surgical instrument channels 1407S1, 1407S3 have mirror symmetry about a minor axis 1491 of the oblong cross section of entry guide 1407.

Entry guide 1408 (FIG. 14H) is a second example of a transoral entry guide. Entry guide 1408 has a modified triangle cross section. The cross section is a non-circular cross section and is referred to as a modified triangle cross section because the vertices of the triangle shape are rounded and one side of the triangle has a small arc in the center. Entry guide 1408 includes four channels. The four channels are an oblong camera channel 1408C and three circular standard instrument channels 1408S1, 1408S2, 1408S3. In this aspect, the three circular standard surgical instrument channels 1408S1, 1408S2, 1408S3 have a same diameter, e.g., 0.310 inches (7.9 mm).

First circular standard surgical instrument channel 1408S1 has a lengthwise axis 1485. The oblong cross section of camera channel 1408C has a major axis 1486 and a minor axis 1487. Third circular standard surgical instrument channel 1408S3 has a lengthwise axis 1488. Second circular standard surgical instrument channel 1408S2 has a lengthwise axis 1489.

Lengthwise axes 1485, 1488 intersect a line 1490 that includes major axis 1486. Line 1490 is referred to as a major axis 1490 of a cross section of entry guide 1408. Lengthwise axis 1489 intersects a straight line 1491 that includes minor axis 1487. Line 1491 is referred to as a minor axis 1490 of a cross section of entry guide 1408. Major axis 1490 and minor axis 1491 intersect at length wise axis of oblong camera channel 1408C. Entry guide 1408 has minor symmetry about minor axis 1491.

Entry guide 1409 (FIG. 14I) is a first example of a thoracic entry guide. Entry guide 1409 has a non-circular cross section that is a cross section with two parallel sides connected by two arcs, e.g., an oblong-like cross section. Entry guide 1409 includes three channels. The three channels are an oblong camera channel 1409C and two circular standard instrument channels 1409S1, 1409S3. In this aspect, the two circular standard surgical instrument channels 1409S1, 1409S3 have a same diameter, e.g., 0.310 inches (7.9 mm).

Entry guide 1410 (FIG. 14J) is a second example of a thoracic entry guide. Entry guide 1410 has a non-circular cross section that is an oblong-like cross section. Entry guide 1410 includes three channels. The three channels are an oblong camera channel 1410C and two circular advanced surgical instrument channels 1410A1, 1410A3. In this aspect, the two circular advanced surgical instrument channels 1410A1, 1410A3 have a same diameter, e.g., 0.428 inches (10.9 mm).

Table 2 is a summary of the information presented above for entry guides 1401 to 1410. The sizes presented are illustrative only and are not intended to limit the entry guides to the specific dimensions presented.

TABLE 2

| Entry Guide Configurations | | Entry Guide OD or Maximum Dimension (mm) | Manual Lumen (mm) | Cannula | |
|---|---|---|---|---|---|
| Name | Channel Descriptions | | | Main (mm) | 2$^{nd}$ axis (mm) |
| Standard 1401 | Camera, Standard | 25.0 | — | 26.4 | — |
| Four Lumen: Advanced Vessel Sealer 1402 | Camera, Vessel Sealer Standard | 31.0 | — | 32.4 | — |
| Four Lumen: Advanced Vessel Sealer 1403 | Camera Stapler Standard | 31.0 | — | 32.4 | — |
| Four Lumen: Manual 1404 | Camera Manual Standard | 31.0 | 17.0 | 32.4 | — |
| Four Lumen: Vessel Sealer with Manual 1405 | Camera, Vessel Sealer Manual | 31.0 | 12.0 | 32.4 | — |
| Five Lumen: Manual 1406 | Camera Manual Standard | 31.0 | 12.8. | 32.4 | — |
| Three Lumen: Horizontal 1407 | Camera Standard | 35.4 | — | 36.8 | 14 |
| Four Lumen: Horizontal: 1408 | Camera Standard | 35.4 | — | 36.8 | 23.0 |
| Three Lumen: Vertical 1409 | Camera Standard | 32.5 | — | 33.9 | 19.7 |
| There Lumen: Vertical Vessel Sealer 1410 | Camera Vessel Sealer | 36.0 | — | 37.4 | 19.7 |

Figure 15:
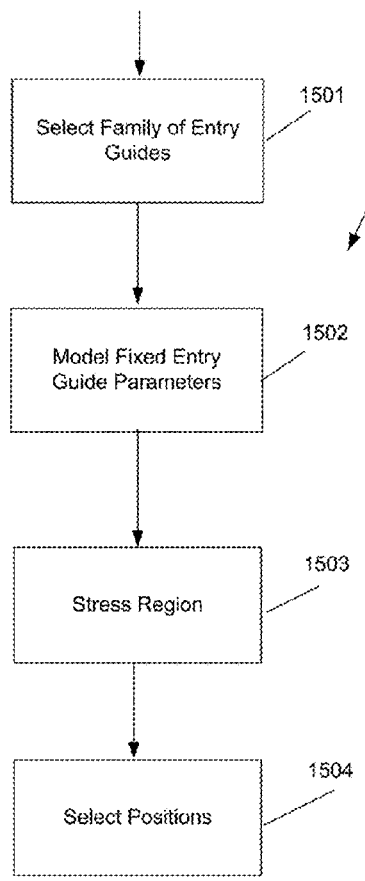
FIG. 15 is a process flow diagram of a method used to determine the range of motion required and the trajectory to be implemented in each of the four gearboxes in FIG. 9 for the family of entry guides in FIGS. 14A to 14J.

The ten entry guide configurations with the three cannulas were analyzed to determine the range of motion required and the trajectory to be implemented in each of the four gearboxes. FIG. 15 is a process flow diagram of a method used to perform the analysis.

In SELECT FAMILY OF ENTRY GUIDES 1501, a family of entry guides is selected. This process is equivalent to the considerations described above with respect to FIGS. 14A to 14J, and so is not repeated here. In general terms, the selection of entry guides in the family and the cannula sizes was based on clinical needs, system feasibility, logistics, and manufacturability. The clinical needs included the surgical instruments needed for the various surgical procedures that can be carried out by the minimally invasive surgical system. In the above examples, the family includes entry guides for standard surgical instruments, advanced surgical instruments, manual surgical instruments, camera instruments, and combinations of these instruments. In addition, the entry guides are selected to facilitate using as few different cannula sizes as possible in one aspect. The entry guide channel configurations are laid out according to logistics in use of the surgical instruments and manufacturability of the entry guides.

After a family of entry guides has been selected, MODEL FIXED ENTRY GUIDE PARAMETERS process 1502 process is performed. Some of the entry guide parameters can be directly derived from the shape and size of the entry guide, without consideration of the instrument manipulator positioning system or the surgical device assembly. For example, a camera instrument channel is always centered on the Y-axis and the center of the camera instrument channel is positioned as far as possible from the longitudinal axis of the entry guide. This provides the most room for the other surgical instrument channels and manual instrument channel(s), and results in an intuitive arrangement of the surgical instruments relative to the camera for the surgeon. Similarly, the channels for the shafts of the first and third surgical device assemblies are typically positioned symmetrically about the camera channel, at the perimeter of the entry guide, and as close as possible to the camera channel. This provides the most room for the manual channel and more flexibility for placing the channel for the shaft of another surgical device assembly mounted on the base assembly.

Upon completion of MODEL FIXED ENTRY GUIDE PARAMETERS process 1502, stress regions are drawn around each instrument lumen position showing the allowable offset between the actual and ideal (minimum stress) instrument positions in STRESS REGION process 1503. The boundary of each stress region is a line of isostress. Any point interior to the boundary has less stress than the stress on the isostress boundary.

Figure 16A:
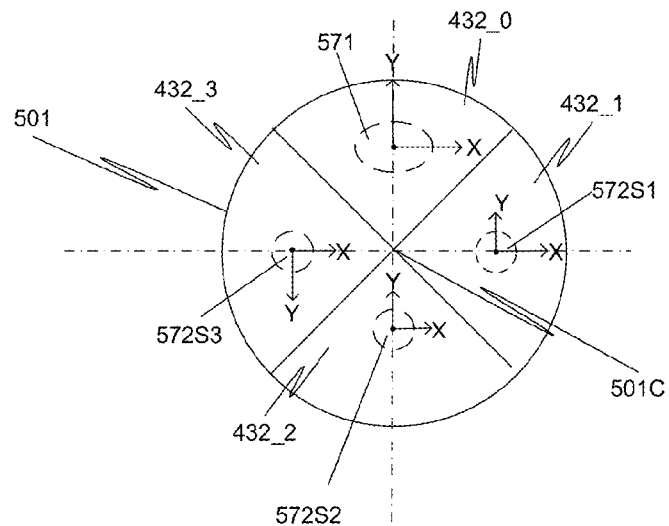
FIG. 16A is a schematic representation of base assemblies mounted on the entry guide manipulator and the coordinate system used by the instrument manipulator positioning system.

Thus, minimum stress positions are first determined. In one aspect, the minimum stress position is chosen as the location where the bend in the shaft is a circular bend. With one end of the shaft fixed in place and another part of the shaft having approximately two point contact with the entry guide, the shaft follows a circular arc. The stress is being applied by a pure moment. This circular bending was taken as minimizing the stress in the shaft over the bending length, e.g. over a six inch (152.2 mm) length. In Table 3, the ideal positions for the positioning elements and hence the surgical instrument shafts are given as (x, y) coordinates. The direction of x and y is defined at the location of each positioning element in the base assembly. The values of the (x, y) coordinates (in inches) in Table 3 provide the nominal location for each instrument insertion assembly. FIG. 16A is FIG. 5A redrawn with the (x, y) coordinate systems added. As is known to those of skill in the art, the coordinates in Table 3 can be converted to millimeters by multiplying each coordinate by 25.4.

TABLE 3

| Entry Guide Ref. No. | Positioning Element in Base Assembly 432_0 | | Positioning Element in Base Assembly 432_1 | | Positioning Element in Base Assembly 432_2 | | Positioning Element in Base Assembly 432_3 | |
|---|---|---|---|---|---|---|---|---|
| | X | Y | X | Y | X | Y | X | Y |
| 1401 | 0.000 | 0.245 | 0.288 | −0.094 | 0.000 | −0.303 | −0.288 | 0.094 |
| 1402 | 0.000 | 0.363 | 0.361 | 0.000 | 0.000 | −0.353 | −0.361 | 0.000 |
| 1403 | 0.000 | 0.363 | 0.406 | 0.110 | 0.000 | −0.250 | −0.406 | −0.110 |
| 1404 | 0.000 | 0.363 | 0.406 | 0.110 | — | — | −0.406 | −0.110 |
| 1405 | 0.000 | 0.363 | 0.361 | 0.000 | — | — | −0.361 | 0.000 |
| 1406 | 0.000 | 0.363 | 0.420 | 0.110 | −0.286 | −0.308 | −0.420 | −0.110 |
| 1407 | 0.000 | 0.000 | 0.506 | 0.000 | 0.000 | −0.414 | −0.506 | 0.000 |
| 1408 | 0.000 | 0.000 | 0.506 | 0.000 | 0.000 | −0.414 | −0.506 | 0.000 |
| 1409 | 0.000 | 0.393 | 0.156 | 0.000 | 0.000 | −0.451 | −0.156 | 0.000 |
| 1410 | 0.000 | 0.461 | 0.111 | 0.000 | 0.000 | −0.453 | −0.111 | 0.000 |

Transoral and thoracic entry guides 1407 to 1410 only use two of the three instrument manipulators, but positions are specified for positioning elements in all three base assemblies. This is done to avoid collisions and to provide a gap for a sterile drape. Typically, when only two manipulator assemblies and associated surgical instruments are used with an entry guide, base assembly 432_1 and base assembly 432_2 are used to position the two manipulator assemblies.

Figure 16B:
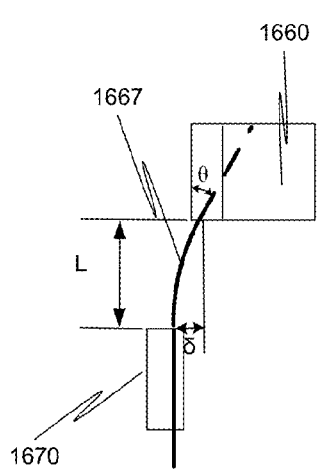
FIG. 16B is a schematic representation of a surgical instrument with a shaft that is entering an entry guide mounted in a cannula, where the shaft is bent against the entry guide.
Figure 16C:
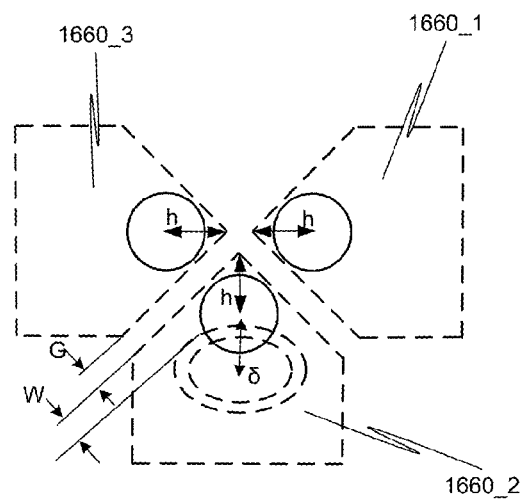
FIG. 16C is a schematic top view of three surgical instruments mounted as illustrated in FIGS. 3A and 3B.

To facilitate placing the channels in the entry guide closer together to minimize the cannula diameter, the shafts of the surgical instruments are angled from the instrument housings (See FIG. 4B) and bent against the entry guide as they pass through the cannula. This makes up for space lost to the shaft bearings and lost to the wall thickness of the instrument housing. FIG. 16B illustrates a surgical instrument 1660 with a shaft 1667 that is entering an entry guide 1670 mounted in a cannula. Shaft 1667 is bent against entry guide 1670. Surgical instrument 460 is an example of surgical instrument 1660. FIG. 16C is a schematic top view of three surgical instruments 1660_1, 1660_2, 1660_3 mounted as illustrated in FIGS. 3A and 3B for surgical instruments 260_1, 260_2, 260_3.

With one end of shaft 1667 fixed at the instrument housing and another point on shaft 1667 having approximately two point contact with a wall of the channel in entry guide 1670 (FIG. 16B), shaft 1667 follows a circular arc as depicted in FIG. 16B. The amount of bending or angle θ needed is a function of a distance L of the bottom of the instrument housing to the top of entry guide 1670, and the relative distances of the channel from adjacent instrument housing and lumens. Angle θ is the shaft exit angle from the housing. Distance δ is distance from a center of shaft 1667 to an outer diameter of a bearing B (FIG. 16C) mounted at the proximal end of shaft 1667. Distance h is a housing theoretical sharp dimension that is used to show the derived location of the instrument housing relative to the channel. Distance G is a minimum distance that is maintained between adjacent instrument housings.

The circular bending assumptions minimize the stress in the shaft over the bending length assuming the worst-case insertion depth L. However, other bending can be achieved as needed to provide additional offset between the instrument housing and the entry guide lumen. This S-bending increases the shaft stress as a function of its magnitude and direction (either perpendicular or in-line to the circular bend). As used herein, an S-shaped bend, e.g., S-bending, is created when a moment and a force are applied simultaneously to the shaft. To understand how much S-bending can be tolerated, for a given shaft material, a region bounded by an isostress boundary is plotted around the ideal instrument location. The positioning element can be offset as needed to insert the shaft into the channel so long as the stress on the shaft remains on or within the isostress boundary. If the positioning element is moved from the ideal position, extra shaft bending is imposed on the instrument shaft, but the stresses associated with the extra shaft bending are within acceptable stress levels so long as the position of the positioning element, and hence the instrument shaft, remains within the isostress boundary.

In one aspect, the shaft material for the standard surgical instruments was stainless steel, e.g., a precipitation hardened stainless steel such as 17-4 or 17-7 stainless steel condition H1050. However, for the advanced surgical instruments, a different material is used. To tolerate the increased bend angle on a larger shaft, it is necessary to select a different material for the shafts of the vessel sealer and stapler instruments.

The advanced surgical instruments have high strength plastic shafts to allow for bending through the cannulas. In one aspect, the shafts are made from a polyether ether ketone (PEEK) plastic. PEEK plastic is an organic polymer thermoplastic. In one aspect, a PEEK plastic with a flexural modulus of 11.8 GPa (1,711 ksi) is selected for the shafts of the advanced surgical instruments. The tensile fatigue of this PEEK plastic at $10^7$ cycles is a tensile strength of about 14,500 psi. A PEEK plastic having these characteristics is manufactured by Victrex® Manufacturing Limited as PEEK 450GL30. (VICTREX is a registered trademark of Victrex Manufacturing Limited of Lancashire FY5 4QD, United Kingdom.) Alternative grades of PEEK with higher stiffness are available. The alternative grades of PEEK have a modulus of elasticity of 45 GPa and 22 GPa. These grades might be required for some advanced surgical instruments to prevent shaft buckling under high cable tension.

Figure 17:
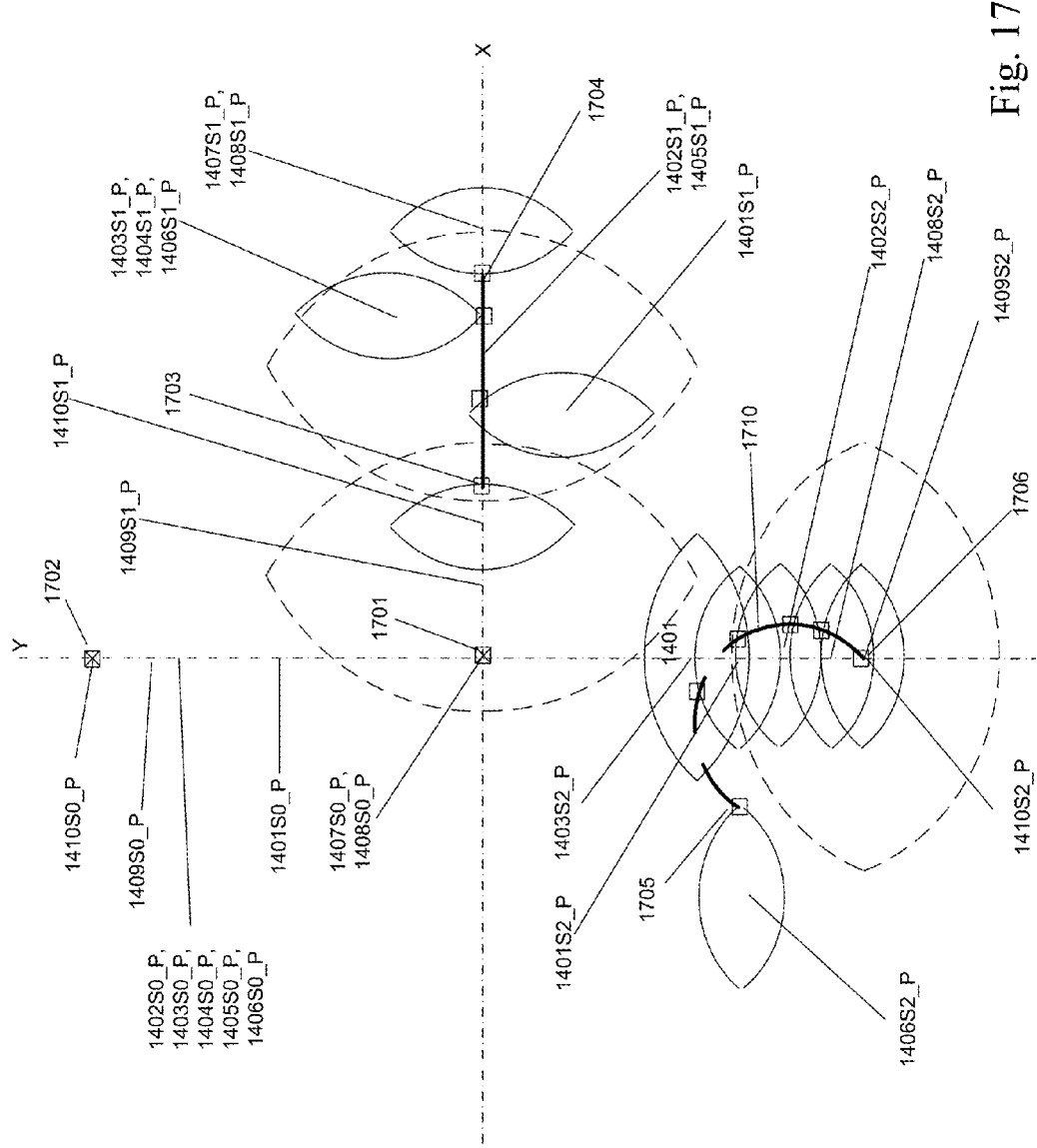
FIG. 17 illustrates acceptable stress regions for each positioning element and the associated entry guide channel showing the allowable offsets from ideal (minimum stress) instrument shaft positions.

In FIG. 17, stress regions, sometimes called stress profiles, bounded by lines of isostress, i.e., bounded by isostress boundaries are presented for each positioning element and the associated entry guide channel showing the allowable offsets from ideal (minimum stress) instrument shaft positions. Each region has a shape that is roughly a cross section of an American football shape, i.e., a cross section of an oblate spheroid shape. The stress on the shaft of an instrument is acceptable if the shaft is positioned at a location within the isostress boundary. Thus, the stress regions in FIG. 17 are regions of acceptable stress associated with bending of a shaft of an instrument. The reference numeral for each stress profile points at the ideal position based on the information in Table 3, which is at the center of the stress profile. A first portion of the reference numeral is the reference numeral of corresponding channel in FIGS. 14A to 14J and this is followed with a _P to indicate that the reference numeral refers to a position. For example, 1408S0_P is the ideal position for the camera instrument shaft when inserted in channel 1408S0 in entry guide 1408.

FIG. 17 shows that the ideal locations of the camera instrument shaft with respect to channels 1401S0_P to 1410S0_P fall on a straight line, which is the positive portion of the y-axis of the entry guide manipulator coordinate system. An isostress boundary is not determined for the camera instrument shaft, because as described above, the camera instrument is pre-bent and so the shaft is not subjected to bending as in passes through an entry guide.

The stress profiles for the instrument shafts controlled by the positioning element associated with base assembly 432_1 are primarily along the x-axis to the right of the y-axis, e.g., the stress profiles having centers 1401S1_P to 1410S1_P as illustrated in FIG. 17. In FIG. 17, the stress profiles for the instrument shafts controlled by the positioning element associated with base assembly 432_2 are below the x-axis, e.g., the stress profiles having centers 1401S2_P to 1410S3_P, 1406S2_P, and 1408S2_P to 1410S2_P, in this aspect.

The stress profiles for the instrument shafts controlled by the positioning element associated with base assembly 432_3 are not presented in FIG. 17. The reason is that for each (x, y) value defining a boundary of a stress profile the instrument shafts controlled by the positioning element associated with base assembly 432_1, the corresponding value on a boundary of a stress profile of an the instrument shaft controlled by the positioning element associated with base assembly 432_3 is (−x, −y). Therefore, when a first trajectory is determined for the positioning element associated with base assembly 432_1, a second trajectory for the positioning element associated with base assembly 432_3 is the negative of the first trajectory. Accordingly, analysis of the stress data associated with positions 1401S1_P to 1410S1_P is sufficient to determine the same information of the positioning element associated with base assembly 432_3.

The stress regions generated in STRESS REGION process 1503 are used in SELECT POSITIONS process 1504. Initially in process 1504, a decision needs to be made on whether to use a linear trajectory gearbox (FIGS. 10C, 10D) or a circular trajectory gearbox (FIGS. 10A, 10B).

Thus, the endpoints of a preliminary trajectory are defined to limit the overall range of motion required. For the positioning element associated with the camera instrument, the range of motion is from position 1701 to 1702 in the (x, y) coordinate system. For the positioning element associated with the first surgical instrument that is coupled to the floating platform in base assembly 432_1, the range of motion is from position 1703 to 1704 in the (x, y) coordinate system. Finally, the positioning element associated with the second surgical instrument coupled to the floating platform in base assembly 432_2, the range of motion is from position 1705 to 1706 in the (x, y) coordinate system.

After the ranges of motion are defined, the trajectories and the positions that make up the trajectories are selected. For the camera instrument, a linear trajectory is required. Thus, a linear trajectory gearbox is selected for the camera instrument. For the first surgical instrument, the stress profiles in FIG. 17 show that a straight line drawn between point 1703 and 1704 intersects all the stress profiles. Therefore, the stress on the first surgical instrument shaft is within a stress profile for each of the channels for points along the x-axis between points 1703 and 1704. Thus, a linear trajectory gearbox is selected for the first and third surgical instruments.

For the second surgical instrument, a straight line between points 1705 and 1706 does not intersect all of the stress profiles and so a linear trajectory is not acceptable. To determine the circular trajectory, an iterative process is used to find a constant radius arc that includes points 1705 and 1706 and that intersects all the stress profiles. Constant radius arc 1710 that includes points 1705 and 1706 and intersects all the stress profiles is selected as the trajectory for the second surgical instrument.

Next, a set of positions are created on each trajectory for the positioning element. Each selected position is on a boundary or within a stress profile. While the selected positions assure that the stress on the instrument shaft is acceptable, there is the possibility that when adjacent instruments are moved to the selected positions, the instrument housings collide. Thus, the relationships of the instruments housings at the selected positions are analyzed to assure that the positions do not result in any collisions.

At each actual position, corresponding instrument housing is drawn based on the layout of FIG. 16C. To avoid over defining the problem, a subset of entry guides in the family of entry guides is empirically selected. Adjacent surgical instrument housings for each entry guide configuration are paired, and the gap between the housing is measured. If there is a collision, the gap between the housings is set at predetermined gap G, e.g., 0.100 inches (2.54 mm) and the selected positions are adjusted to obtain this spacing. If there is not a collision, the gap between the instrument housing is saved for a final verification of the trajectories. This process is repeated for each entry guide in the subset of entry guides. The predetermined gap is also used to define the offsets for the camera-positioning element. For the positions that are not limited by the clearance with an adjacent instrument housing, positions are selected according to convenient properties, such as being evenly spaced along the trajectory or where instrument shaft stress is minimized.

The square boxes along the x-axis in FIG. 17 represent the positions on the linear trajectory of the first surgical instrument. The positions for a linear trajectory are not as critical because, as described above, the positioning element is not constrained to moving in a single direction. In one aspect, the linear trajectory uses some of the points more than once as the trajectory moves back and forth along the trajectory based on the design of the linear gearbox. The square boxes along arc 1710 in FIG. 17 represent the positions on the circular trajectory of the second surgical instrument.

Figure 18A:
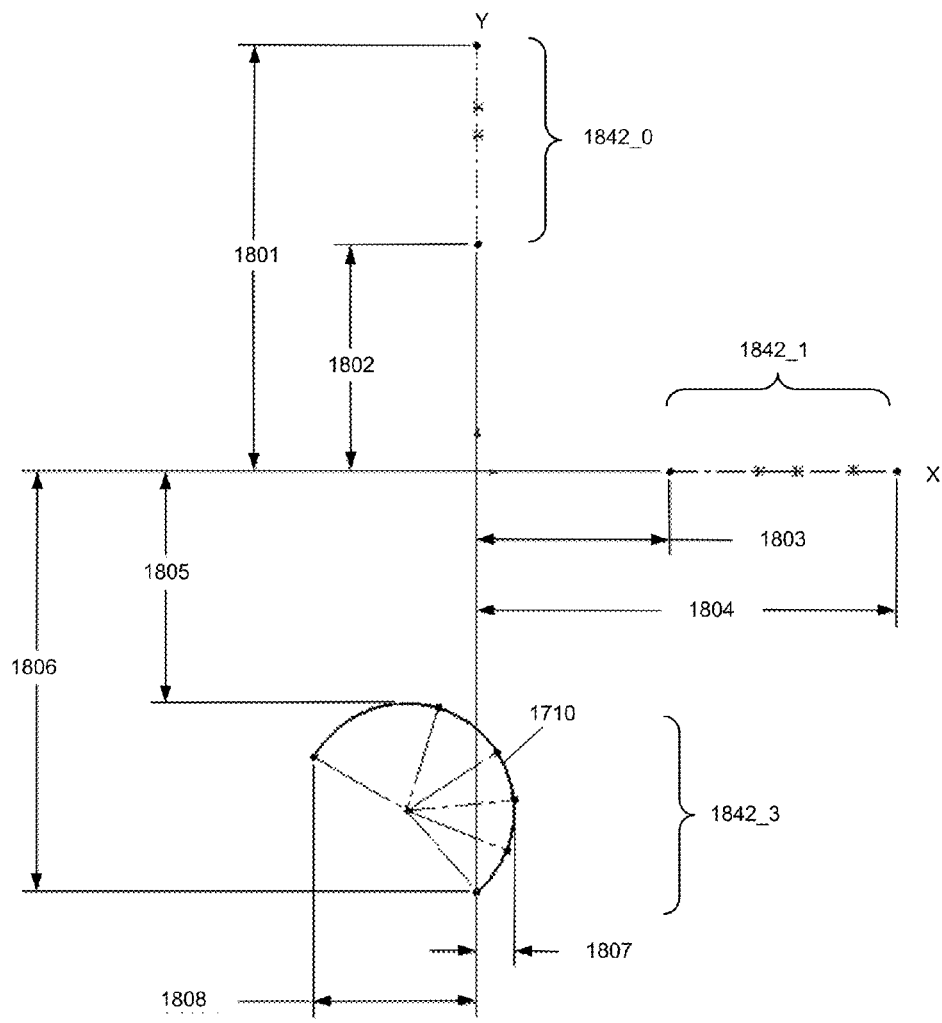
FIG. 18A illustrates the surgical instrument and camera instrument trajectories and ranges of motion of gearboxes in FIG. 9 for the family of entry guides in FIGS. 14A to 14J.

FIG. 18A illustrates the surgical instrument and camera instrument trajectories and ranges of motion of the output pins of gearboxes 1842_0, 1842_1, 1842_2 for the family of entry guides in FIGS. 14A to 14J. The plot is oriented looking down the cannula, with each gearbox position labeled. The trajectory of the output pin of gearbox 1842_3 (not shown) is not drawn because it is taken as the negative of the trajectory and range of motion of gearbox 1842_1. As shown, the trajectory of the output pin of gearbox 1842_3 is circular and the other trajectories of the other three gearboxes are linear. Table 4 give values associated with the reference numbers in FIG. 18 for entry guides 1401 to 1410.

TABLE 4

| Reference No. | Dimension (inches) |
|---|---|
| 1801 | 0.461 (11.69 mm) |
| 1802 | 0.245 (6.21 mm) |
| 1803 | 0.208 (5.07 mm) |
| 1804 | 0.454 (11.51 mm) |
| 1805 | 0.250 (6.34 mm) |
| 1806 | 0.454 (11.51 mm) |
| 1807 | 0.040 (1.01 mm) |
| 1808 | 0.177 (4.49 mm) |

Figure 19A:
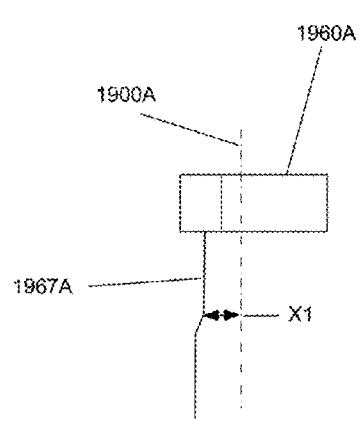
FIGS. 19A and 19B are schematic illustrations of camera instruments having a pre-bent shaft.
Figure 19B:
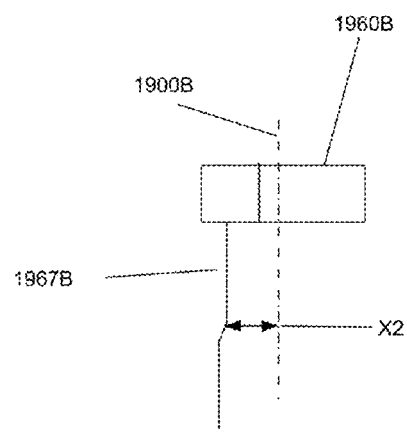

To reduce the range of motion of the camera instrument, in one aspect, two camera instruments are used in the surgical system, e.g., surgical system 200C. The first camera instrument is used with all entry guides except entry guides 1407 and 1408. The second camera instrument is used only for entry guides 1407 and 1408. The difference between the two cameras is the location of the shaft bend. FIGS. 19A and 19B are schematic illustrations of camera instruments 1960A and 1960B. Camera instrument 260_0 is an example of either camera instrument 1960A or camera instrument 1960B.

Lines 1900A and 1900B represent planes 1900A and 1900B, respectively that are perpendicular to the page. Plane 1900A bisects a first pair of drive disks of camera instrument 1960A that provide motion to the distal articulating joints of camera instrument 1960A. The location of the start of the bend in shaft 1967A is defined by the distance from the start of the bend in the shaft to plane 1900A. For the first camera instrument, the distance is X1, e.g., 1.739 inches (44.10 mm). Plane 1900B bisects a first pair of drive disks of camera instrument 1960B that provide motion to the distal articulating joints of camera instrument 1960B. For the second camera instrument, the distance is X2, e.g., 1.833 inches (46.48 mm).

The use of the two camera instruments reduces the range of motion required by the linear gearbox associated with the camera instrument to the range presented in FIG. 18 instead of the range of motion of 0.0 to 0.461 inches (0.0 to 11.69 mm) shown in FIG. 17. In another aspect, only a single camera instrument is used.

The range of motion of the gearboxes for the three surgical instruments is 0.246 inches (6.24 mm) in the radial direction and 0.217 inches (5.50 mm) in the lateral direction. The camera gearbox has a range of motion of 0.216 inches (5.48 mm) in the radial direction. Hence, the combined ranges of motion required by all the instruments are 0.246 inches (6.24 mm) in the radial direction and 0.217 inches (5.50 mm) in the lateral direction.

The order of the entry guides as moved by the positioning system in entry guide manipulator is defined by circular gearbox positions for the second surgical instrument. In Table 5, the relative positions are specified as a function of the output gear angle in the circular gearbox.

TABLE 5

| | Entry Guide Ref. No. | | | | | |
|---|---|---|---|---|---|---|
| | 706 | 703, 704 | 701 | 702, 705 | 707, 708 | 709, 710 |
| Output Gear Angle in Gearbox | 0° | 77° | 117° | 133.9° | 150.8° | 161° |

In the above analysis, the bending stress associated with a shaft of an instrument was determined only for the instrument designed to be inserted in a particular channel of the entry guide. For example, a standard surgical instrument with a smaller diameter shaft was not considered to be inserted in one of the larger diameter channels designed for an advanced surgical instrument.

However, in another aspect, it was assumed that a bushing would be inserted in a larger diameter channel so that a standard surgical instrument could be passed through the channel designed, for example, for an advanced surgical instrument. Thus, the stress analysis was repeated for a set of guide tubes where a standard surgical instrument is allowed to be used with a guide tube channel designed, for example, for an advanced surgical instrument. Also, the analysis assured that instrument collisions were not a problem. Finally, the analysis in addition to the constraints imposed by the different channel locations in the entry guides also specified a draping position for each of the instrument manipulators. In particular, the instrument manipulators were moved apart so that draping was facilitated. The result of this analysis was the second set of gearboxes that are illustrated in FIGS. 11A to 11K.

The analysis of the entry guides in combination with the draping position found that each instrument manipulator, e.g., each surgical device assembly, must be moved to one of seven locations to accommodate the set of entry guides of interest. The first location is the draping location, and the other six locations are based on the combination of entry guide and surgical device assembly being used.

Figure 18B:
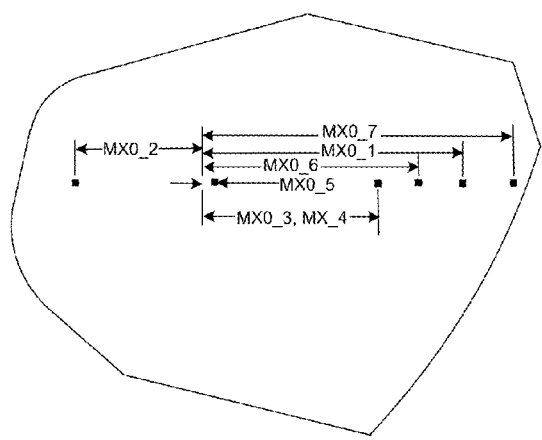
FIG. 18B illustrates the seven locations for the instrument manipulator associated with the gearbox of FIGS. 11A and 11B.
Figure 18C:
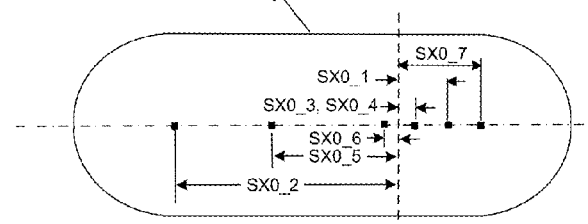
FIG. 18C illustrates the seven locations of the output pin in the slot of FIG. 11B.

FIG. 18B illustrates the seven locations for the instrument manipulator associated with gearbox 942_0_2 (FIGS. 11A and 11B). FIG. 18C illustrates the seven locations of output pin 1149_B in slot 1144_B (FIG. 11B). In FIGS. 18B to 18I, the coordinate systems are relative to the manipulator assembly and not to any world coordinate system. TABLE 6A presents values in inches for each of the dimensions shown in FIG. 18B. TABLE 6B presents values in inches for each of the dimensions shown in FIG. 18C. The numbers in parentheses in TABLES 6A and 6B are in millimeters.

TABLE 6A

| MX0_1 | 0.1880 (4.77) | MY0_1 | 0.0000 (0.00) |
|---|---|---|---|
| MX0_2 | −0.0920 (−2.33) | MY0_2 | 0.0000 (0.00) |
| MX0_3 | 0.1265 (3.21) | MY0_3 | 0.0000 (0.00) |
| MX0_4 | 0.1265 (3.21) | MY0_4 | 0.0000 (0.00) |
| MX0_5 | 0.0091 (0.23) | MY0_5 | 0.0000 (0.00) |
| MX0_6 | 0.1568 (3.98) | MY0_5 | 0.0000 (0.00) |
| MX0_7 | 0.2250 (5.71) | MY0_7 | 0.0000 (0.00) |

TABLE 6B

| SX0_1 | 0.048 (1.22) | SY0_1 | 0.00 (0.00) |
|---|---|---|---|
| SX0_2 | −0.232 (−5.88) | SY0_2 | 0.000 (0.00) |
| SX0_3 | −0.014 (−0.36) | SY0_3 | 0.000 (0.00) |
| SX0_4 | −0.014 (−0.36) | SY0_4 | 0.000 (0.00) |
| SX0_5 | −0.131 (−3.32) | SY0_5 | 0.000 (0.00) |
| SX0_6 | 0.017 (0.43) | SY0_5 | 0.000 (0.00) |
| SX0_7 | 0.085 (2.16) | SY0_7 | 0.000 (0.00) |

Figure 18D:
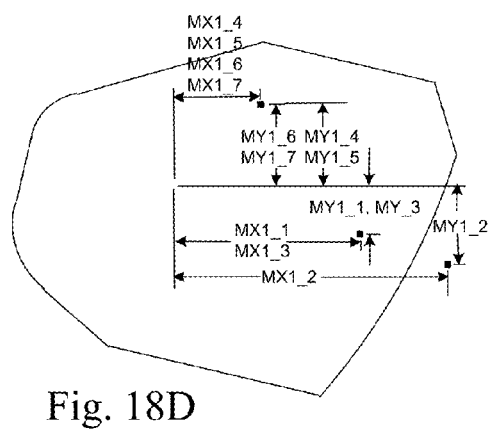
FIG. 18D illustrates the seven locations for the instrument manipulator associated with the gearbox of FIGS. 11C and 11D.
Figure 18E:
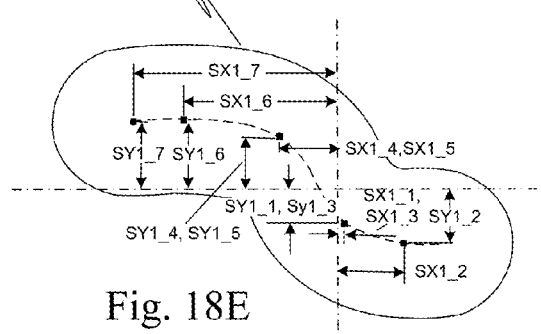
FIG. 18E illustrates the seven locations of the output pin in the slot of FIG. 11D.

FIG. 18D illustrates the seven locations for the instrument manipulator associated with gearbox 942_1_2 (FIGS. 11C and 11D.) FIG. 18E illustrates the seven locations of output pin 1149_D in slot 1144_D (FIG. 11D). TABLE 7A presents values in inches for each of the dimensions shown in FIG. 18D. TABLE 7B presents values in inches for each of the dimensions shown in FIG. 18E. The numbers in parentheses in TABLES 7A and 7B are in millimeters.

TABLE 7A

| | | | |
|---|---|---|---|
| MX1_1 | 0.160 (4.06) | MY1_1 | −0.042 (−1.07) |
| MX1_2 | 0.235 (5.96) | MY1_2 | −0.069 (−1.75) |
| MX1_3 | 0.160 (4.06) | MY1_3 | −0.042 (−1.07) |
| MX1_4 | 0.076 (1.93) | MY1_4 | 0.070 (1.78) |
| MX1_5 | 0.076 (1.93) | MY1_5 | 0.070 (1.78) |
| MX1_6 | 0.076 (1.93) | MY1_5 | 0.069 (1.75) |
| MX1_7 | 0.076 (1.93) | MY1_7 | 0.069 (−1.75) |

TABLE 7B

| | | | |
|---|---|---|---|
| SX1_1 | 0.010 (0.25) | SY1_1 | −0.042 (−1.07) |
| SX1_2 | 0.085 (2.16) | SY1_2 | −0.069 (−1.75) |
| SX1_3 | 0.010 (0.25) | SY1_3 | −0.042 (−1.07) |
| SX1_4 | −0.074 (−1.88) | SY1_4 | 0.070 (1.78) |
| SX1_5 | −0.074 (−1.88) | SY1_5 | 0.070 (1.78) |
| SX1_6 | −0.197 (−5.00) | SY1_5 | 0.091 (2.31) |
| SX1_7 | −0.261 (−6.62) | SY1_7 | 0.089 (2.26) |

FIG. 18F illustrates the seven locations for the instrument manipulator associated with gearbox 942_2_2 (FIGS. 11E to 11H). FIG. 18G illustrates the seven locations of output pin 1149_G in slot 1144_G (FIG. 11G). TABLE 8A presents values in inches for each of the dimensions shown in FIG. 18F. TABLE 8B presents values in inches for each of the dimensions shown in FIG. 18G. The numbers in parentheses in TABLES 8A and 8B are in millimeters.

TABLE 8A

| | | | |
|---|---|---|---|
| MX2_1 | 0.165 (4.18) | MY2_1 | −0.012 (−0.30) |
| MX2_2 | 0.014 (0.36) | MY2_2 | 0.000 (0.00) |
| MX2_3 | 0.024 (0.61) | MY2_3 | 0.000 (0.00) |
| MX2_4 | 0.084 (2.13) | MY2_4 | 0.000 |
| MX2_5 | 0.094 (2.38) | MY2_5 | 0.000 (0.00) |
| MX2_6 | 0.198 (5.02) | MY2_5 | −0.022 (−0.56) |
| MX2_7 | 0.198 (5.02) | MY2_7 | −0.022 (−0.56) |

TABLE 8B

| | | | |
|---|---|---|---|
| SX2_1 | 0.015 (0.38) | SY2_1 | −0.012 (−0.30) |
| SX2_2 | −0.136 (−3.45) | SY2_2 | 0.000 (0.00) |

TABLE 8B-continued

| | | | |
|---|---|---|---|
| SX2_3 | −0.126 (−3.20) | SY2_3 | 0.042 (1.07) |
| SX2_4 | −0.066 (−1.67) | SY2_4 | 0.070 (1.78) |
| SX2_5 | −0.056 (1.42) | SY2_5 | 0.070 (1.78) |
| SX2_6 | 0.048 (1.22) | SY2_5 | −0.022 (−0.56) |
| SX2_7 | 0.048 (1.22) | SY2_7 | −0.022 (−0.56) |

FIG. 18H illustrates the seven locations for the instrument manipulator associated with gearbox 942_3_2 (FIGS. 11I to 11J). FIG. 18I illustrates the seven locations of output pin 1149_J in slot 1144_J (FIG. 11J). TABLE 9A presents values in inches for each of the dimensions shown in FIG. 18D. TABLE 9B presents values in inches for each of the dimensions shown in FIG. 18E. The numbers in parenthesis in TABLES 9A and 9B are in millimeters.

TABLE 9A

| | | | |
|---|---|---|---|
| MX3_1 | 0.160 (4.06) | MY3_1 | 0.042 (1.07) |
| MX3_2 | 0.235 (5.96) | MY3_2 | 0.069 (1.75) |
| MX3_3 | 0.160 (4.06) | MY3_3 | 0.042 (1.07) |
| MX3_4 | 0.076 (1.93) | MY3_4 | −0.070 (−1.78) |
| MX3_5 | 0.076 (1.93) | MY3_5 | −0.070 (−1.78) |
| MX3_6 | −0.047 (−1.19) | MY3_5 | −0.091 (−2.31) |
| MX3_7 | −0.111 (−2.81) | MY3_7 | −0.089 (−2.26) |

TABLE 9B

| | | | |
|---|---|---|---|
| SX3_1 | 0.010 (0.25) | SY3_1 | 0.042 (1.07) |
| SX3_2 | 0.085 (2.16) | SY3_2 | 0.069 (−1.75) |
| SX3_3 | 0.010 (0.25) | SY3_3 | 0.042 (1.07) |
| SX3_4 | −0.074 (−1.88) | SY3_4 | −0.070 (−1.78) |
| SX3_5 | −0.074 (−1.88) | SY3_5 | −0.070 (−1.78) |
| SX3_6 | −0.197 (−5.00) | SY3_5 | −0.091 (−2.31) |
| SX3_7 | −0.261 (−6.62) | SY3_7 | −0.089 (−2.26) |

In one aspect, a control system 2000 (FIG. 20A) of the surgical system includes an instrument manipulator positioning system compatibility module 2010. Control system 2000 also has compatibility and configuration data 2015 that is stored in a memory and a system management module 2025.

Figure 20A:
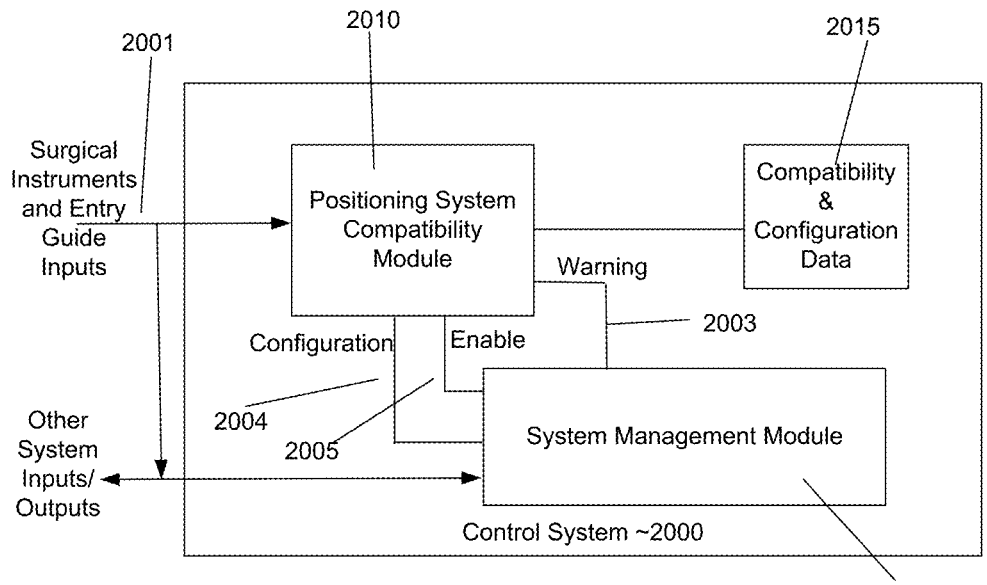
FIG. 20A is a schematic illustration of one aspect of a control system in the surgical system of FIG. 2E.

In FIG. 20A, control system 2000 and system management module 2025 are illustrated as elements in a single location. This is for ease of description and is not intended to be limiting. Typically, control system 2000 and the system management module 2025 are distributed throughout the surgical system and interconnected so that the various components can communicate as necessary. Also, those knowledgeable in the field understand that a module can be implemented in hardware, firmware, stored computer code that is executed on a processor, or any combination of the three.

Figure 20B:
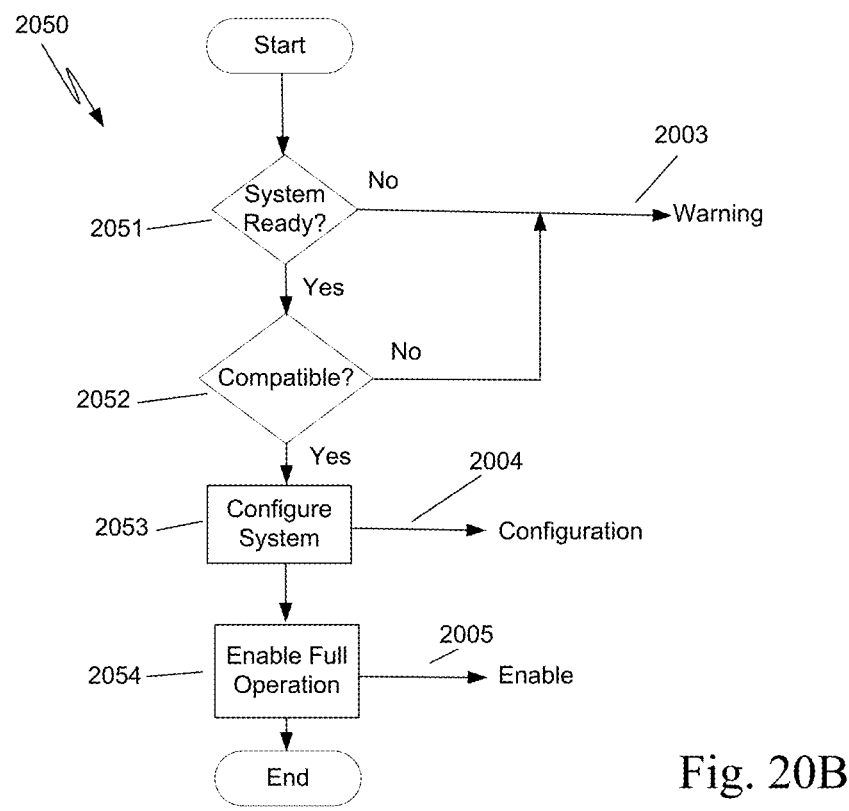
FIG. 20B is a process flow diagram of one aspect of a method performed by the instrument manipulator positioning system compatibility module of FIG. 20A.

In one aspect, instrument manipulator positioning system compatibility module 2010 performs method 2050 (FIG. 20B). Prior to considering method 2050 in further detail, it is helpful to understand some of the surgical instrument and entry guide inputs 2001. When sterile adapter assembly 250 is mounted on manipulator assembly 240 (FIG. 4A) a switch is activated that sends a signal to system management module 2025 and to compatibility and configuration data 2015 indicating mounting of sterile adapter assembly 250. In response to this signal, control system 2000 activates drive motors in manipulator assembly 240 to mate drive disks in manipulator assembly 240 with intermediate disks in sterile adapter assembly 250.

When surgical instrument 260 is mounted in sterile adapter assembly 250, a second switch is activated that sends a signal to system management module 2025 and to compatibility and configuration data 2015 indicating mounting of surgical instrument 260. In response to this signal, control system 2000 activates the drive motors in manipulator assembly 240 to mate the intermediate disks in sterile adapter assembly 250 with driven disks in driven interface assembly 461 of surgical instrument 260. Controls system 2000 also activates the RFID reader 445 in manipulator assembly 240 to read the RFID tag 455 on surgical instrument 260. The identification information read from RFID tag is supplied to system management module 2025 and to compatibility and configuration data 2015.

Thus, as each surgical instrument is mounted on system 210C, a signal indicating the mounting and information about the surgical instrument are provided to SYSTEM READY check process 2051. Also, identification information of cannula 275E and entry guide 270E are supplied to SYSTEM READY check process 2051. In one aspect, RFID tags on cannula 275E and entry guide 270E are scanned by an RFID reader connected to control system 2090 to obtain the identification information. In another aspect, a user enters the identification information of cannula 275E and entry guide 270E via a user interface provided by control system 2000, e.g., a user interface on the surgeon's control console. Also, the identification information could be obtained via color, physical features such as pins on the mount paint, magnetic rings, etc.

If a user tries to use system 200C prior to SYSTEM READY check process 2051 receiving the information from the surgical instruments and from the cannula and entry guide, SYSTEM READY check process 2051 activates a first warning signal 2003 to system management module 2025. In response to first active warning signal 2003, system management module 2025 generates a warning to the user. For example, a message is presented on display screens indicating that one or more components have not been registered with control system 2000 and that system operation is inhibited until successful registration. In addition to the visual message, an audio message or alarm may be generated.

When all the surgical instruments, the cannula, and the entry guide have been registered with control system 2000, SYSTEM READY check process 2051 transfers processing to COMPATIBLE check process 2052. COMPATIBLE check process 2052 retrieves information from stored compatibility and configuration data 2015 that is associated with the entry guide mounted in system 200C. COMPATIBLE check process 2052 first checks that the entry guide is in the family of entry guides associated with the instrument manipulator positioning system in entry guide manipulator 230. If the entry guide is not in the family, check process 2052 sends a second active warning signal 2003 to control system 2000 that in turn notifies the user that the entry guide is not appropriate for use in system 200C.

If the entry guide is in the family, check process 2052 determines whether the mounted surgical instruments and camera instrument are compatible with the mounted entry guide, and if the surgical instruments are compatible whether the surgical instruments are mounted in the correct locations. If either of these checks is not true, check process 2052 sends a third active warning signal 2003 to control system 2000 that in turn notifies the user of the problem with the surgical instrument configuration.

In one aspect, check process 2052 determines whether other elements installed on system 200C, such as, drapes, foot pedal control assemblies, master control assemblies, etc. are compatible based on the entry guide configuration and causes a warning message to be sent if an incompatibility is detected.

When check process 2052 determines that the various elements installed on system 200C are compatible, processing transfers to CONFIGURE SYSTEM process 2053. In one aspect, CONFIGURE SYSTEM process 2053 automatically activates the instrument manipulator positioning system and moves the adjustment disk to the appropriate position so that each of the instrument shafts are positioned for insertion into the entry guide. In another aspect, CONFIGURE SYSTEM process 2053 sends a first active configuration message signal 2004 to system management module 2025. In response to signal 2004, system management module 2025 sends a command to a display module to inform the user to manually move the adjustment disk to the correct position.

In one aspect, CONFIGURE SYSTEM process 2053 also retrieves configuration data from compatibility and configuration data 2015 and sends the data to system management module 2025 to configure system 200C for operation with the entry guide. For example, system management module 2025 uses the configuration data to adjust its user interface for a specific type of surgery given the type of entry guide installed. Module 2025 can use the configuration data to adjust user interface elements, allowable control modes, type and behavior of control modes, design of visible interface elements, audible tones, and any other aspect of the user interface for either the surgeon or patient side assistant, based on the entry guide configuration. Upon completion of CONFIGURE SYSTEM process 2053, ENABLE FULL OPERATION process 2054 sends an active enable signal 2005 to system management module 2025 to indicate that system 200C is properly configured to perform surgery with the entry guide mounted in system 200C.

FIGS. 21A and 21B are illustrations of a side view of base assemblies 2132_0 and 2132_1 mounted to a portion 2130 of entry guide manipulator 230. In one aspect, an insertion assembly with an attached surgical device assembly is connected to a floating platform in each of base assemblies 2132_0 and 2132_1, but the insertion assembly with the attached surgical device assembly is not shown in FIGS. 21A and 21B.

Base assembly 2132_0 is connected to portion 2130 by a hinge assembly 2133_0. A plane including a longitudinal axis of hinge assembly 2133_0 is perpendicular to a plane including the longitudinal axis of entry guide manipulator 230. Similarly, base assembly 2132_1 is connected to portion 2130 by a hinge assembly 2133_1. Each of the other two base assemblies that are not visible in FIG. 21A is similarly connected to portion 2130. In FIG. 21B, base assemblies 2132_0 and 2132_1 have been pivoted to allow access to base assemblies 2132_0 and 2132_1 for maintenance or other actions. Base assemblies 2132_2 and 2132_3 are visible in FIG. 21B.

FIG. 22A is a side view of base assemblies 2232_0 and 2232_1 mounted to a portion 2230 of entry guide manipulator 230. FIGS. 22B and 22C are top views of base assemblies 2232_0, 2232_1, 2232_2, and 2232_2 mounted to portion 2230. In one aspect, an insertion assembly with an attached surgical device assembly is connected to a floating platform in each of base assemblies 2232_0, 2232_1, and 2232_2, but the insertion assembly with the attached surgical device assembly is not shown in FIGS. 22A to 22C.

Base assembly 2232_0 is connected to portion 2230 by a hinge assembly 2233_0. Hinge assembly 2233_0 extends distally from entry guide manipulator 230. Similarly, base assembly 2232_1 is connected to portion 2230 by a hinge assembly 2233_1. Each of the other two base assemblies 2232_2, and 2232_2 is similarly connected to portion 2230 by hinge 2233_2 and hinge 2233_3, respectively. In FIG. 22C, base assembly 2232_1 has been pivoted to allow access to base assembly 2232_1 for maintenance or other actions.

FIGS. 23A and 23B are illustrations of a side view of base assemblies 2332_0 and 2332_1 mounted to a portion 2330 of entry guide manipulator 230. In one aspect, an insertion assembly with an attached surgical device assembly is connected to a floating platform in each of base assemblies 2332_0 and 2332_1, but the insertion assembly with the attached surgical device assembly is not shown in FIGS. 23A and 23B.

Base assembly 2332_0 is connected to portion 2330 by a set of rails. Similarly, base assembly 2332_1 is connected to portion 2330 by a set of rails. Each of the other two base assemblies that are not visible in FIG. 23A is similarly connected to portion 2330. In FIG. 23B, base assembly 2332_1 has been slid out on set of rails 2333_1 to allow access to base assembly 2332_1 for maintenance or other actions. Base assembly 2332_2 is visible in FIG. 23B.

In some of the above examples, the terms "proximal" or "proximally" are used in a general way to describe an object or element which is closer to a manipulator arm base along a kinematic chain of system movement or farther away from a remote center of motion (or a surgical site) along the kinematic chain of system movement. Similarly, the terms "distal" or "distally" are used in a general way to describe an object or element which is farther away from the manipulator arm base along the kinematic chain of system movement or closer to the remote center of motion (or a surgical site) along the kinematic chain of system movement.

As used herein, "first," "second," "third," "fourth," etc. are adjectives used to distinguish between different components or elements. Thus, "first," "second," "third," "fourth," etc. are not intended to imply any ordering of the components or elements, or any particular number of different types of elements, e.g., three elements of the same type can be denoted as first, second, and third elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures were turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:
1. A medical device comprising:
a manipulator system comprising:
a roll system coupled to first and second instrument manipulators, wherein the roll system is configured to roll the first and second instrument manipulators as a group about a longitudinal axis of an entry guide, wherein the first instrument manipulator is couplable to a first instrument, and wherein the second instrument manipulator is couplable to a second instrument; and
an instrument manipulator positioning system coupled to the roll system and coupled to the first and second instrument manipulators, wherein the instrument manipulator positioning system is configured to move at least one of the first and second instrument manipulators to simultaneously align shafts of first and second instruments with different channels in an entry guide.
2. The medical device of claim 1:
wherein the instrument manipulator positioning system comprises an adjustment ring gear; and
wherein the roll system comprises a roll ring gear.
3. The medical device of claim 2, wherein the instrument manipulator positioning system further comprises:
a first gearbox coupled to the first instrument and coupled to the adjustment ring gear; and a second gearbox coupled to the second instrument and coupled to the adjustment ring gear.

4. The medical device of claim 3, wherein the first gearbox comprises:
a gear; and
a pin coupled to the gear,
wherein the pin determines a location of the first instrument.

5. The medical device of claim 4, wherein the pin is mounted on a side surface of the gear, and wherein the pin has one degree of freedom.

6. The medical device of claim 5, wherein the one degree of freedom comprises an arc with a constant radius.

7. The medical device of claim 4:
wherein a side surface of the gear comprises a cam, wherein the pin rides on the cam; and
wherein the pin has two degrees of freedom.

8. The medical device of claim 4, the first gearbox further comprising a range of motion stop.

9. The medical device of claim 1, wherein the first instrument manipulator includes a first plurality of motors, and wherein the second instrument manipulator includes a second plurality of motors.

10. The medical device of claim 1:
wherein the first instrument manipulator includes an instrument mount interface having a plurality of outputs; and
wherein the first instrument further includes a body and a transmission unit, the body housing the transmission unit, and the shaft extending from the body, wherein the transmission unit includes a plurality of inputs configured to be coupled to the plurality of outputs of the instrument mount interface.

11. A medical device comprising:
a manipulator system comprising:
a roll system coupled to first and second instrument manipulators, the roll system comprising a roll ring gear, wherein the roll system is configured to roll the first and second instrument manipulators as a group about a longitudinal axis of an entry guide, wherein the first instrument manipulator is couplable to a first instrument, and wherein the second instrument manipulator is couplable to a second instrument;
an instrument manipulator positioning system coupled to the roll system and coupled to the first and second instrument manipulators, the instrument manipulator positioning system comprising an adjustment ring gear, wherein the instrument manipulator positioning system is configured to move at least one of the first and second instrument manipulators to simultaneously align shafts of first and second instruments with different channels in an entry guide; and
a drive assembly coupled to the roll ring gear and coupled to the adjustment ring gear, wherein the drive assembly is configured to differentially rotate the adjustment ring gear and the roll ring gear to cause the instrument manipulator positioning system to move the or each of the first and second instrument manipulators to simultaneously align shafts of the first and second instruments with the different channels in the entry guide.

12. The medical device of claim 11:
wherein the drive assembly is configured to hold the roll ring gear stationary; and
wherein the drive assembly is configured to turn the adjustment ring gear while the roll ring gear is held stationary.

13. The medical device of claim 11:
wherein the drive assembly is configured to hold the adjustment ring gear stationary; and
wherein the drive assembly is configured to turn the roll ring gear while the adjustment ring gear is held stationary.

14. The medical device of claim 11, wherein the drive assembly comprises:
an instrument manipulator positioning system gear train configured to drive the adjustment ring gear; and
a roll system gear train configured to drive the roll ring gear.

15. The medical device of claim 11, wherein the drive assembly comprises:
a brake configured to selectively maintain one of the adjustment ring gear and the roll ring gear stationary.

16. The medical device of claim 15, wherein the drive assembly comprises:
a drive motor; and
a clutch configured to couple and de-couple the drive motor with the adjustment ring gear.

17. The medical device of claim 11, wherein the drive assembly comprises:
a drive motor; and
a clutch configured to couple and de-couple the drive motor with the adjustment ring gear.

18. The medical device of claim 11, wherein the drive assembly further comprises a manually operated knob coupled to the adjustment ring gear.

* * * * *